(12) United States Patent
Yoshida et al.

(10) Patent No.: US 9,741,934 B2
(45) Date of Patent: Aug. 22, 2017

(54) POLYMER COMPOUND AND LIGHT EMITTING DEVICE USING THE SAME

(71) Applicant: Sumitomo Chemical Company, Limited, Tokyo (JP)

(72) Inventors: Tomoyasu Yoshida, Tsukuba (JP); Mio Shiratori, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/127,847

(22) PCT Filed: Nov. 21, 2014

(86) PCT No.: PCT/JP2014/081668
§ 371 (c)(1),
(2) Date: Sep. 21, 2016

(87) PCT Pub. No.: WO2015/145871
PCT Pub. Date: Oct. 1, 2015

(65) Prior Publication Data
US 2017/0092864 A1  Mar. 30, 2017

(30) Foreign Application Priority Data

Mar. 25, 2014 (JP) ................. 2014-061357

(51) Int. Cl.
*C08G 75/00* (2006.01)
*H01L 51/00* (2006.01)
(Continued)

(52) U.S. Cl.
CPC ........ *H01L 51/0035* (2013.01); *C07C 13/567* (2013.01); *C07C 22/04* (2013.01); *C07C 25/02* (2013.01); *C07C 31/20* (2013.01); *C07C 33/30* (2013.01); *C07C 35/38* (2013.01); *C07F 5/003* (2013.01); *C07F 5/025* (2013.01); *C07F 15/0033* (2013.01); *C08G 61/12* (2013.01); *C08G 61/122* (2013.01); *C08G 61/128* (2013.01); *C09K 11/025* (2013.01); *C09K 11/06* (2013.01); *H01L 51/0039* (2013.01); *H01L 51/0043* (2013.01); *C07C 2102/06* (2013.01); *C07C 2103/18* (2013.01); *C08G 61/10* (2013.01); *C08G 61/126* (2013.01); *C08G 2261/124* (2013.01); *C08G 2261/135* (2013.01); *C08G 2261/312* (2013.01); *C08G 2261/3142* (2013.01); *C08G 2261/3162* (2013.01); *C08G 2261/411* (2013.01); *C08G 2261/512* (2013.01); *C08G 2261/514* (2013.01); *C08G 2261/76* (2013.01); *C08G 2261/95* (2013.01); *C08L 65/00* (2013.01); *C09K 2211/1059* (2013.01); *C09K 2211/185* (2013.01); *H01L 51/5016* (2013.01); *H01L 51/5056* (2013.01); *H01L 51/5072* (2013.01); *H01L 51/5088* (2013.01); *H01L 51/5092* (2013.01)

(58) Field of Classification Search
CPC ........ C08G 2261/3162; C08G 2261/76; C08G 2261/95; C08L 79/02; H01L 51/0039
See application file for complete search history.

(56) References Cited

U.S. PATENT DOCUMENTS

| | | | |
|---|---|---|---|
| 2007/0031699 A1* | 2/2007 | Yamada | C08G 61/00 428/690 |
| 2009/0315453 A1 | 12/2009 | Kobayashi et al. | |
| 2011/0127516 A1 | 6/2011 | Nakatani et al. | |
| 2011/0198573 A1 | 8/2011 | Iida et al. | |

(Continued)

FOREIGN PATENT DOCUMENTS

| | | |
|---|---|---|
| CN | 102212190 A | 10/2011 |
| CN | 102686669 A | 9/2012 |

(Continued)

OTHER PUBLICATIONS

Int'l Search Report dated Feb. 24, 2015 in Int'l Application No. PCT/JP2014/081668.
Int'l Preliminary Report on Patentability dated Sep. 27, 2016 in Int'l Application No. PCT/JP2014/081668.
Office Action issued Apr. 1, 2017 in CN Application No. 201480077285.7.

*Primary Examiner* — Shane Fang
(74) *Attorney, Agent, or Firm* — Panitch Schwarze Belisario & Nadel LLP

(57) ABSTRACT

A polymer compound comprising a constitutional unit having a group represented by the formula (1):

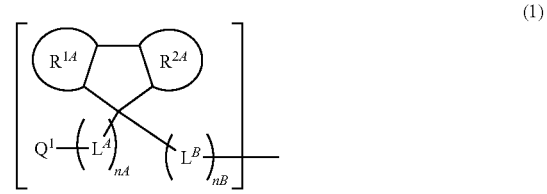

(1)

wherein Ring $A^{1A}$ and Ring $R^{2A}$ represent an aromatic hydrocarbon ring or a heterocyclic ring and these rings each optionally have a substituent, nA represents an integer of 0 to 5, nB represents an integer of 1 to 5, $L^A$ and $L^B$ represent an alkylene group, a cycloalkylene group, an arylene group, a divalent heterocyclic ring group, a group represented by —NR'—, an oxygen atom or a sulfur atom, and R' represents a hydrogen atom, an alkyl group or the like, and $Q^1$ represents a crosslinkable group.

10 Claims, No Drawings

(51) Int. Cl.
*C07F 15/00* (2006.01)
*C07F 5/00* (2006.01)
*C07F 5/02* (2006.01)
*C08G 61/12* (2006.01)
*C07C 13/567* (2006.01)
*C07C 22/04* (2006.01)
*C07C 25/02* (2006.01)
*C07C 31/20* (2006.01)
*C07C 33/30* (2006.01)
*C07C 35/38* (2006.01)
*C09K 11/02* (2006.01)
*C09K 11/06* (2006.01)
*C08G 61/10* (2006.01)
*C08L 65/00* (2006.01)
*H01L 51/50* (2006.01)

(56) References Cited

U.S. PATENT DOCUMENTS

| | | | |
|---|---|---|---|
| 2012/0199825 A1* | 8/2012 | Soga | C07D 213/22 257/40 |
| 2012/0306358 A1 | 12/2012 | Hirano et al. | |
| 2015/0115204 A1 | 4/2015 | Sekine et al. | |

FOREIGN PATENT DOCUMENTS

| | | |
|---|---|---|
| CN | 103339167 A | 10/2013 |
| JP | 2002155131 A | 5/2002 |
| JP | 2007204635 A | 8/2007 |
| JP | 2011149013 A | 8/2011 |
| WO | 2005049689 A2 | 6/2005 |
| WO | 2010018813 A1 | 2/2010 |
| WO | 2012104628 A1 | 8/2012 |
| WO | 2013146806 A1 | 10/2013 |

* cited by examiner

POLYMER COMPOUND AND LIGHT EMITTING DEVICE USING THE SAME

CROSS-REFERENCE TO RELATED APPLICATION

This application is a Section 371 of International Application No. PCT/JP2014/081668, filed Nov. 21, 2014, which was published in the Japanese language on Oct. 1, 2015, under International Publication No. WO 2015/145871 A1, and the disclosure of which is incorporated herein by reference.

TECHNICAL FIELD

The present invention relates to a polymer compound and a light emitting device using the same.

BACKGROUND ART

Light emitting devices such as an organic electroluminescent device can be suitably used for the application of a display and are recently attracting attention, because of high light emission efficiency and low driving voltage. A light emitting device has organic layers such as a light emitting layer and a charge transporting layer. Polymer compounds used for production of a light emitting device are investigated because an organic layer can be formed by application methods typified by an inkjet printing method, by use of the polymer compound.

It is known that a fluorene is useful as a skeleton of a material used in an organic layer of a light emitting device and a polymer compound comprising a constitutional unit derived from a fluorene is particularly useful as a material used in a light emitting layer and a hole transporting layer of a light emitting device. For example, Patent document 1 discloses that a polymer compound comprising a constitutional unit derived from an arylamine and a constitutional unit represented by the following formula (001) derived from a fluorene having a benzocyclobutane structure is used in a hole transporting layer of a light emitting device. Benzocyclobutane functions as a crosslinkable group. Patent document 2 discloses that a polymer compound comprising a constitutional unit derived from an arylamine and a constitutional unit represented by the following formula (002) derived from a fluorene having a styrene structure is used in a hole transporting layer of a light emitting device. Styrene functions as a crosslinkable group. Accordingly, the hole transporting layer which is substantially insoluble in a solvent can be formed by forming a film of the polymer compound by an application method, then, crosslinking benzocyclobutane or styrene by heating and the like. On the hole transporting layer, a light emitting layer and the like can be laminated by an application method.

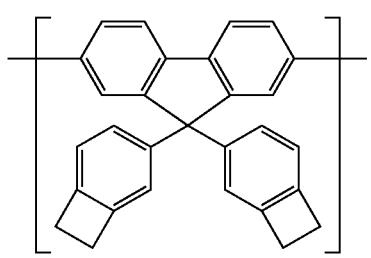

(001)

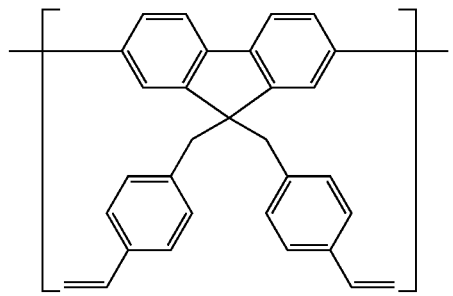

(002)

PRIOR ART DOCUMENT

Patent Document

Patent document 1: JP-A No. 2008-106241
Patent document 2: Japanese Patent Application National Publication No. 2007-528916

SUMMARY OF THE INVENTION

Problems to be Solved by the Invention

A light emitting device produced by using the polymer compound disclosed above comprising a constitutional unit derived from a fluorene, however, had not necessarily sufficient light emission efficiency.

Then, the present invention has an object of providing a polymer compound which is useful for production of a light emitting device excellent in light emission efficiency. Additionally, the present invention has an object of providing a composition comprising the polymer compound and a light emitting device produced by using the polymer compound. The present invention further has an object of providing a compound which is useful for production of the polymer compound.

Means for Solving the Problems

The present invention provides the following [1] to [11].
[1] A polymer compound comprising a constitutional unit having a group represented by the following formula (1):

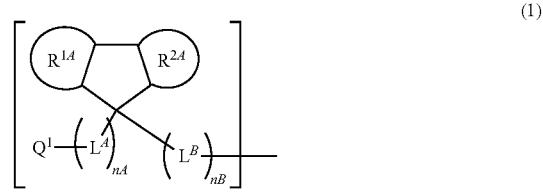

(1)

[wherein,
Ring $R^{1A}$ and Ring $R^{2A}$ each independently represent an aromatic hydrocarbon ring or a heterocyclic ring, and these rings each optionally have a substituent.

nA represents an integer of 0 to 5, and nB represents an integer of 1 to 5.

$L^A$ and $L^B$ each independently represent an alkylene group, a cycloalkylene group, an arylene group, a divalent heterocyclic ring group, a group represented by —NR'—, an oxygen atom or a sulfur atom, and these groups each optionally have a substituent. R' represents a hydrogen atom, an alkyl group, a cycloalkyl group, an aryl group or a monovalent heterocyclic group, and these groups each optionally have a substituent. When a plurality of $L^A$ and $L^B$ are present, they may be the same or different at each occurrence.

$Q^1$ represents a crosslinkable group selected from the following Group A' of crosslinkable group.]

(Group A' of Crosslinkable Group)

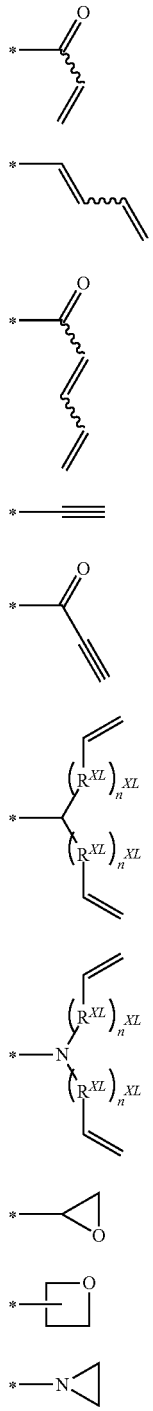

(XL-2)

(XL-3)

(XL-4)

(XL-5)

(XL-6)

(XL-7)

(XL-8)

(XL-9)

(XL-10)

(XL-11)

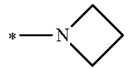

(XL-12)

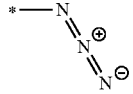

(XL-13)

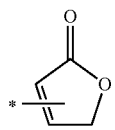

(XL-14)

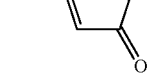

(XL-15)

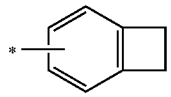

(XL-17)

[wherein, $R^{XL}$ represents a methylene group, an oxygen atom or a sulfur atom, and $n^{XL}$ represents an integer of 0 to 5. When a plurality of $R^{XL}$ are present, they may be the same or different, and when a plurality of $n^{XL}$ are present, they may be the same or different.

* represents a binding position.

These crosslinkable groups each optionally have a substituent.].

[2] The polymer compound according to [1], wherein the constitutional unit having a group represented by the formula (1) is a constitutional unit represented by the following formula (2):

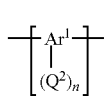

(2)

[wherein, $Ar^1$ represents an aromatic hydrocarbon group or a heterocyclic ring group, and these groups each optionally have a substituent.

n represents an integer of 1 to 4.

$Q^2$ represents a group represented by the formula (1). When a plurality of $Q^2$ are present, they may be the same or different.].

[3] The polymer compound according to [1] or [2], further comprising a constitutional unit represented by the following formula (X):

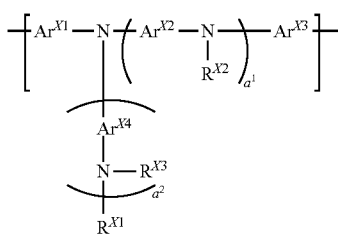 (X)

[wherein, $a^1$ and $a^2$ each independently represent an integer of 0 or more.

$Ar^{X1}$ and $Ar^{X3}$ each independently represent an arylene group or a divalent heterocyclic ring group, and these groups each optionally have a substituent.

$Ar^{X2}$ and $Ar^{X4}$ each independently represent an arylene group, a divalent heterocyclic ring group or a divalent group in which at least one arylene group and at least one divalent heterocyclic ring group are bonded directly to each other, and these groups each optionally have a substituent.

$R^{X1}$, $R^{X2}$ and $R^{X3}$ each independently represent a hydrogen atom, an alkyl group, a cycloalkyl group, an aryl group or a monovalent heterocyclic group, and these groups each optionally have a substituent.].

[4] The polymer compound according to any one of [1] to [3], further comprising a constitutional unit represented by the following formula (Y):

 (Y)

[wherein, $Ar^{Y1}$ represents an arylene group, a divalent heterocyclic ring group or a divalent group in which at least one arylene group and at least one divalent heterocyclic ring group are bonded directly to each other, and these groups each optionally have a substituent.].

[5] The polymer compound according to any one of [1] to [4], wherein Ring $R^{1A}$ and Ring $R^{2A}$ are a benzene ring optionally having a substituent. [6] The polymer compound according to any one of [2] to [5], wherein $Ar^1$ is a group obtained by removing from a benzene ring optionally having a substituent, a fluorene ring optionally having a substituent, a naphthalene ring optionally having a substituent, a phenanthrene ring optionally having a substituent or a dihydrophenanthrene ring optionally having a substituent (2+n) hydrogen atoms linked directly to carbon atoms constituting the ring.

[7] The polymer compound according to any one of [4] to [6], wherein the constitutional unit represented by the formula (Y) is a constitutional unit represented by the following formula (Y-1) or a constitutional unit represented by the following formula (Y-2):

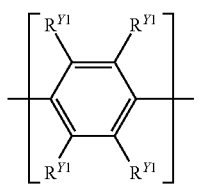 (Y-1)

[wherein, $R^{Y1}$ represents a hydrogen atom, an alkyl group, a cycloalkyl group, an alkoxyl group, a cycloalkoxy group, an aryl group or a monovalent heterocyclic group, and these groups each optionally have a substituent. The plurality of $R^{Y1}$ may be the same or different, and adjacent $R^{Y1}$s may be combined together to form a ring together with the carbon atoms to which they are attached.]

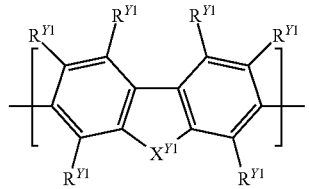 (Y-2)

[wherein, $R^{Y1}$ represents the same meaning as described above. $X^{Y1}$ represents a group represented by $—C(R^{Y2})_2—$, $—C(R^{Y2})=C(R^{Y2})—$ or $—C(R^{Y2})_2)—$. $R^{Y2}$ represents a hydrogen atom, an alkyl group, a cycloalkyl group, an alkoxyl group, a cycloalkoxy group, an aryl group or a monovalent heterocyclic group, and these groups each optionally have a substituent. The plurality of $R^{Y2}$ may be the same or different, and $R^{Y2}$s may be combined together to form a ring together with the carbon atoms to which they are attached.].

[8] The polymer compound according to any one of [2] to [7], wherein the content of the constitutional unit represented by the above-described formula (2) is 3 to 90 mol % with respect to the total content of constitutional units contained in the polymer compound.

[9] A compound represented by the following formula (2M):

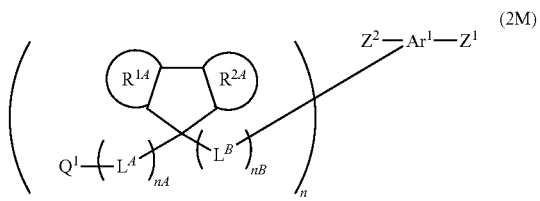 (2M)

[wherein,

Ring $R^{A1}$, $R^{A2}$, nA, nB, $L^A$, $L^B$ and $Q^1$ represent the same meaning as described above.

$Ar^1$ represents an aromatic hydrocarbon group or a heterocyclic ring group, and these groups each optionally have a substituent.

n represents an integer of 1 to 4.

$Z^1$ and $Z^2$ each independently represent a group selected from the following Group A of substituent or Group B of substituent.

<Group A of Substituent>

A chlorine atom, a bromine atom, an iodine atom and a group represented by $—O—S(=O)_2R^{C1}$ (wherein $C^{C1}$ represents an alkyl group, a cycloalkyl group or an aryl group, and these groups each optionally have a substituent.).

<Group B of Substituent>

A group represented by $—B(OR^{C2})_2$ (wherein, $R^{C2}$ represents a hydrogen atom, an alkyl group, a cycloalkyl group or an aryl group, and these groups each optionally have a substituent. The plurality of $R^{C2}$ may be the same or different and may be combined together to form a cyclic structure together with the oxygen atoms to which they are attached.);

a group represented by —BF$_3$Q' (wherein, Q' represents a lithium atom, a sodium atom, a potassium atom, a rubidium atom or a cesium atom.);

a group represented by —MgY' (wherein, Y' represents a chlorine atom, a bromine atom or an iodine atom.);

a group represented by —ZnY" (wherein, Y" represents a chlorine atom, a bromine atom or an iodine atom.); and a group represented by —Sn(R$^{C3}$)$_3$ (wherein R$^{C3}$ represents a hydrogen atom, an alkyl group, a cycloalkyl group or an aryl group, and these groups each optionally have a substituent. The plurality of R$^{C3}$ may be the same or different and may be combined together to form a cyclic structure together with the tin atom to which they are attached.).

[10] A composition comprising the polymer compound according to any one of [1] to [8] and at least one material selected from the group consisting of a hole transporting material, a hole injection material, an electron transporting material, an electron injection material, a light emitting material, an antioxidant and a solvent.

[11] A light emitting device produced by using the polymer compound according to any one of [1] to [8].

Effect of the Invention

The present invention can provide a polymer compound which is useful for production of a light emitting device excellent in light emission efficiency. Additionally, the present invention can provide a composition comprising the polymer compound and a light emitting device obtained by using the polymer compound. The present invention can further provide a compound which is useful for production of the polymer compound.

MODES FOR CARRYING OUT THE INVENTION

Suitable embodiments of the present invention will be illustrated in detail below.

<Explanation of Common Term>

Toxins commonly used in the present specification have the following meanings unless otherwise stated.

Me represents a methyl group, Et represents an ethyl group, Bu represents a butyl group, i-Pr represents an isopropyl group, and t-Bu represents a tert-butyl group.

A hydrogen atom may be a light hydrogen atom or a heavy hydrogen atom.

A solid line representing a bond to a central metal in a formula representing a metal complex denotes a coordinate bond or a covalent bond.

"Polymer compound" denotes a polymer having molecular weight distribution and having a polystyrene-equivalent number average molecular weight of 1×10$^3$ to 1×10$^8$.

"Low molecular weight compound" denotes a compound having no molecular weight distribution and having a molecular weight of 1×10$^4$ or less.

"Constitutional unit" denotes a unit structure found once or more in a polymer compound.

"Alkyl group" may be any of linear or branched. The number of carbon atoms of the linear alkyl group is, not including the number of carbon atoms of a substituent, usually 1 to 50, preferably 3 to 30, more preferably 4 to 20. The number of carbon atoms of the branched alkyl groups is, not including the number of carbon atoms of a substituent, usually 3 to 50, preferably 3 to 30, more preferably 4 to 20.

The alkyl group optionally has a substituent, and examples thereof include a methyl group, an ethyl group, a propyl group, an isopropyl group, a butyl group, an isobutyl group, a tert-butyl group, a pentyl group, an isoamyl group, a 2-ethylbutyl group, a hexyl group, a heptyl group, a octyl group, a 2-ethylhexyl group, a 3-propylheptyl group, a decyl group, a 3-dimethyloctyl group, a 2-ethyloctyl group, a 2-hexyldecyl group and a dodecyl group, and groups obtained by substituting a hydrogen atom in these groups with a cycloalkyl group, an alkoxy group, a cycloalkoxy group, an aryl group, a fluorine atom or the like, and the alkyl group having a substituent includes a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-n-hexylphenyl)propyl group and a 6-ethyloxyhexyl group.

The number of carbon atoms of a cycloalkyl group is, not including the number of carbon atoms of a substituent, usually 3 to 50, preferably 3 to 30, more preferably 4 to 20.

The cycloalkyl group optionally has a substituent, and examples thereof include a cyclohexyl group, a cyclohexylmethyl group and a cyclohexylethyl group.

"Aryl group" denotes an atomic group remaining after removing from an aromatic hydrocarbon one hydrogen atom linked directly to a carbon atom constituting the ring. The number of carbon atoms of the aryl group is, not including the number of carbon atoms of a substituent, usually 6 to 60, preferably 6 to 20, more preferably 6 to 10.

The aryl group optionally has a substituent, and examples thereof include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group, a 4-phenylphenyl group, and groups obtained by substituting a hydrogen atom in these groups with an alkyl group, a cycloalkyl group, an alkoxy group, a cycloalkoxy group, an aryl group, a fluorine atom or the like.

"Alkoxy group" may be any of linear or branched. The number of carbon atoms of the linear alkoxy group is, not including the number of carbon atoms of a substituent, usually 1 to 40, preferably 4 to 10. The number of carbon atoms of the branched alkoxy group is, not including the number of carbon atoms of a substituent, usually 3 to 40, preferably 4 to 10.

The alkoxy group optionally has a substituent, and examples thereof include a methoxy group, an ethoxy group, a propyloxy group, an isopropyloxy group, a butyloxy group, an isobutyloxy group, a tert-butyloxy group, a pentyloxy group, a hexyloxy group, a heptyloxy group, a octyloxy group, a 2-ethylhexyloxy group, a nonyloxy group, a decyloxy group, a 3,7-dimethyloctyloxy group and a lauryloxy group, and groups obtained by substituting a hydrogen atom in these groups with a cycloalkyl group, an alkoxy group, a cycloalkoxy group, an aryl group, a fluorine atom or the like.

The number of carbon atoms of a cycloalkoxy group is, not including the number of carbon atoms of a substituent, usually 3 to 40, preferably 4 to 10.

The cycloalkoxy group optionally has a substituent, and examples thereof include a cyclohexyloxy group.

The number of carbon atoms of "Aryloxy group" is, not including the number of carbon atoms of a substituent, usually 6 to 60, preferably 7 to 48.

The aryloxy group optionally has a substituent, and examples thereof include a phenoxy group, a 1-naphthyloxy group, a 2-naphthyloxy group, a 1-anthracenyloxy group, a 9-anthracenyloxy group, a 1-pyrenyloxy group, and groups obtained by substituting a hydrogen atom in these groups with an alkyl group, a cycloalkyl group, an alkoxy group, a cycloalkoxy group, a fluorine atom or the like.

"p-Valent heterocyclic group" (p represents an integer of 1 or more) denotes an atomic group remaining after removing from a heterocyclic compound p hydrogen atoms among hydrogen atoms directly linked to a carbon atom or a hetero atom constituting the ring. Of p-valent heterocyclic groups, "p-valent aromatic heterocyclic groups" as an atomic group remaining after removing from an aromatic heterocyclic compound p hydrogen atoms among hydrogen atoms directly linked to a carbon atom or a hetero atom constituting the ring are preferable.

"Aromatic heterocyclic compound" denotes a compound in which the heterocyclic ring itself shows aromaticity such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzosilole and dibenzophosphole, and a compound in which an aromatic ring is condensed to the heterocyclic ring even if the heterocyclic ring itself shows no aromaticity such as phenoxazine, phenothiazine, dibenzoborole, dibenzosilole and benzopyran.

The number of carbon atoms of the monovalent heterocyclic group is, not including the number of carbon atoms of a substituent, usually 2 to 60, preferably 4 to 20.

The monovalent heterocyclic group optionally has a substituent, and examples thereof include a thienyl group, a pyrrolyl group, a furyl group, a pyridyl group, a piperidyl group, a quinolyl group, an isoquinolyl group, a pyrimidinyl group, a triazinyl group, and groups obtained by substituting a hydrogen atom in these groups with an alkyl group, a cycloalkyl group, an alkoxy group, a cycloalkoxy group or the like.

"Halogen atom" denotes a fluorine atom, a chlorine atom, a bromine atom, or an iodine atom.

"Amino group" optionally has a substituent, and a substituted amino group is preferable. The substituent which an amino group has is preferably an alkyl group, a cycloalkyl group, an aryl group or a monovalent heterocyclic group.

The substituted amino group includes, for example, a dialkylamino group, a dicycloalkylamino group and a diarylamino group.

The amino group includes, for example, a dimethylamino group, a diethylamino group, a diphenylamino group, a bis(4-methylphenyl)amino group, a bis(4-tert-butylphenyl) amino group and a bis(3,5-di-tert-butylphenyl)amino group.

"Alkenyl group" may be any of linear or branched. The number of carbon atoms of the linear alkenyl group, not including the number of carbon atoms of the substituent, is usually 2 to 30, preferably 3 to 20. The number of carbon atoms of the branched alkenyl group, not including the number of carbon atoms of the substituent, is usually 3 to 30, preferably 4 to 20.

The number of carbon atoms of a cycloalkenyl group, not including the number of carbon atoms of the substituent, is usually 3 to 30, preferably 4 to 20.

The alkenyl group and cycloalkenyl group each optionally have a substituent, and examples thereof include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group, a 7-octenyl group, and these groups having a substituent.

"Alkynyl group" may be any of linear or branched. The number of carbon atoms of the alkynyl group, not including the number of carbon atoms of the substituent, is usually 2 to 20, preferably 3 to 20. The number of carbon atoms of the branched alkynyl group, not including the number of carbon atoms of the substituent, is usually 4 to 30, preferably 4 to 20.

The number of carbon atoms of a cycloalkynyl group, not including the number of carbon atoms of the substituent, is usually 4 to 30, preferably 4 to 20.

The alkynyl group and cycloalkynyl group each optionally have a substituent, and examples thereof include an ethynyl group, a 1-propynyl group, a 2-propynyl group, a 2-butynyl group, a 3-butynyl group, a 3-pentynyl group, a 4-pentynyl group, a 1-hexenyl group, a 5-hexenyl group, and these groups having a substituent.

"Arylene group" denotes an atomic group remaining after removing from an aromatic hydrocarbon two hydrogen atoms linked directly to carbon atoms constituting the ring. The number of carbon atoms of the arylene group is, not including the number of carbon atoms of a substituent, usually 6 to 60, preferably 6 to 30, more preferably 6 to 18.

The arylene group optionally has a substituent, and examples thereof include a phenylene group, a naphthalenediyl group, an anthracenediyl group, a phenanthrenodiyl group, a dihydrophenanthrenediyl group, a naphthacenediyl group, a fluorenediyl group, a pyranediyl group, a perylenediyl group, a chrysenediyl group, and these groups having a substituent, preferably, groups represented by the formulae (A-1) to (A-20). The arylene group includes groups obtained by linking a plurality of these groups.

(A-1)

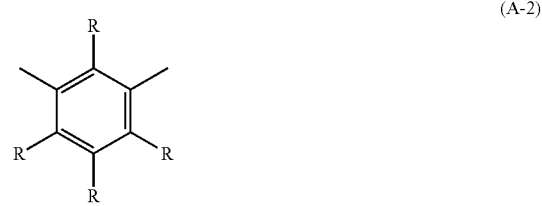

(A-2)

(A-3)

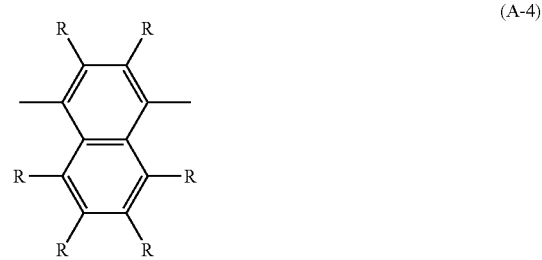

(A-4)

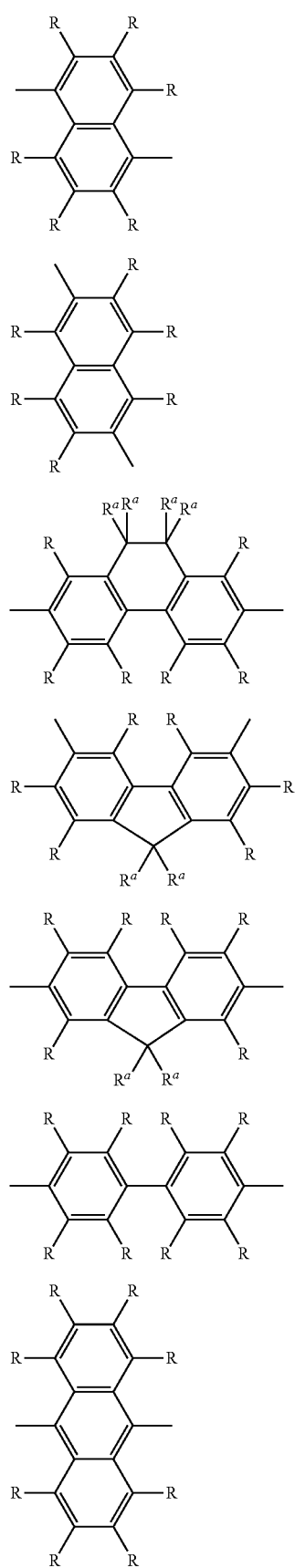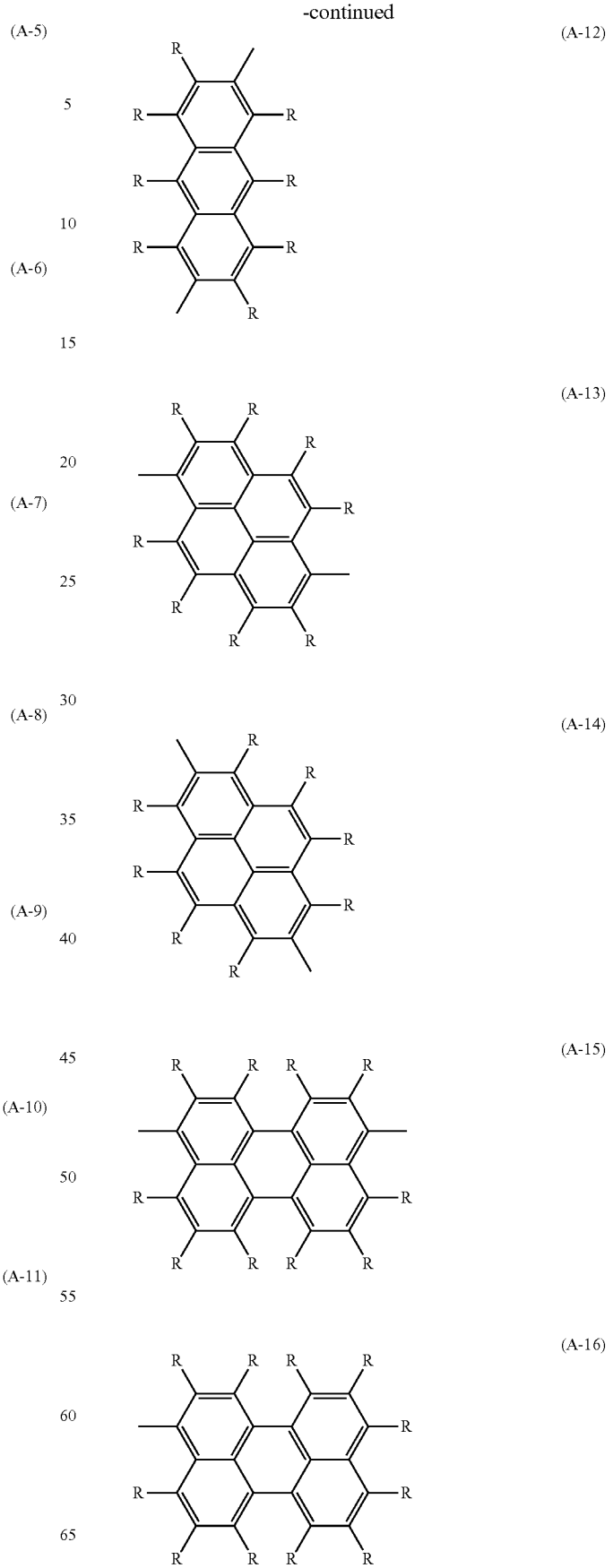

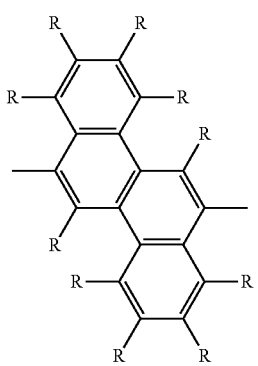
(A-17)

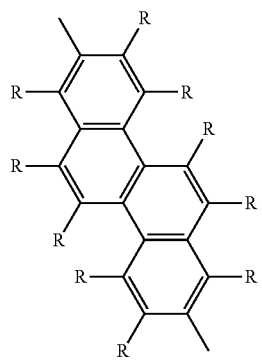
(A-18)

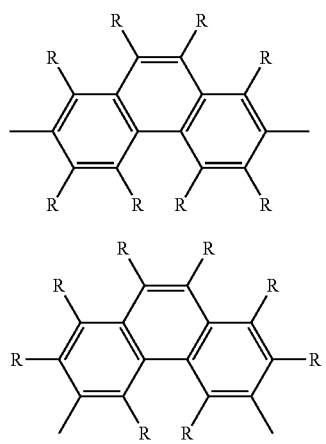
(A-19)

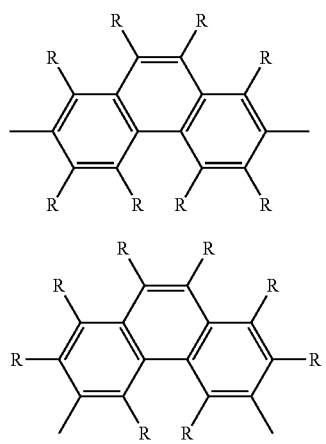
(A-20)

[wherein, R and $R^a$ each independently represent a hydrogen atom, an alkyl group, a cycloalkyl group, an aryl group or a monovalent heterocyclic group. The plurality of R and $R^a$ each may be the same or different, and adjacent $R^a$s may be combined together to form a ring together with the atoms to which they are attached.]

The number of carbon atoms of the divalent heterocyclic group is, not including the number of carbon atoms of a substituent, usually 2 to 60, preferably 3 to 30, more preferably 4 to 15.

The divalent heterocyclic group optionally has a substituent, and examples thereof include divalent groups obtained by removing from pyridine, diazabenzene, triazine, azanaphthalene, diazanaphthalene, carbaxole, dibenzofuran, dibenzothiophene, dibenzosilole, phenoxazine, phenothiazine, acridine, dihydroacridine, furan, thiophene, azole, diazole and triazole two hydrogen atoms among hydrogen atoms linking directly to a carbon atom or a hetero atom constituting the ring, preferably groups represented by the formulae (AA-1) to (AA-34). The divalent heterocyclic group includes groups obtained by linking a plurality of these groups.

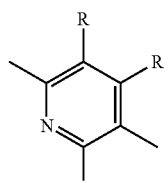
(AA-1)

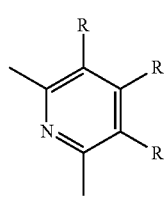
(AA-2)

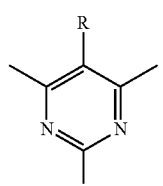
(AA-3)

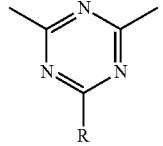
(AA-4)

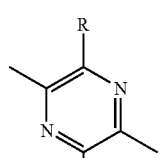
(AA-5)

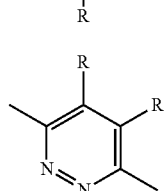
(AA-6)

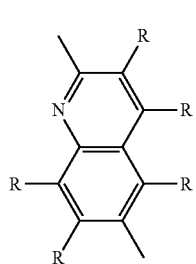
(AA-7)

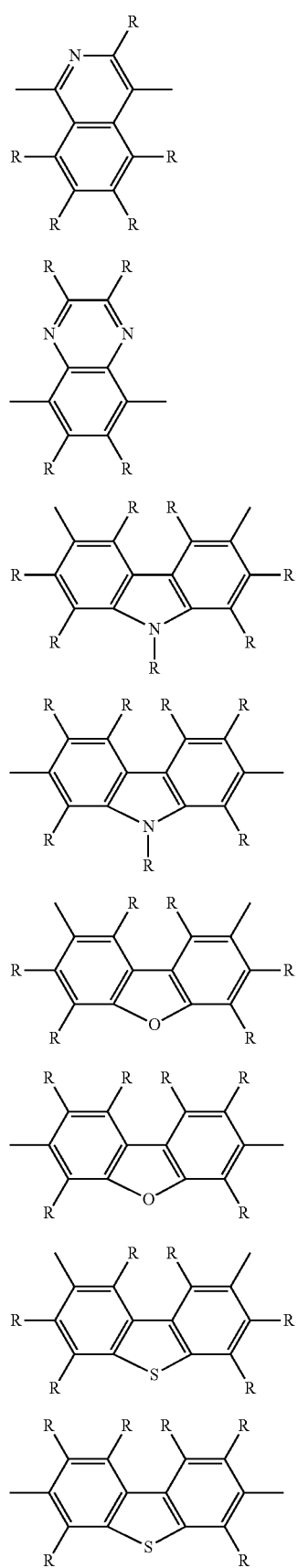
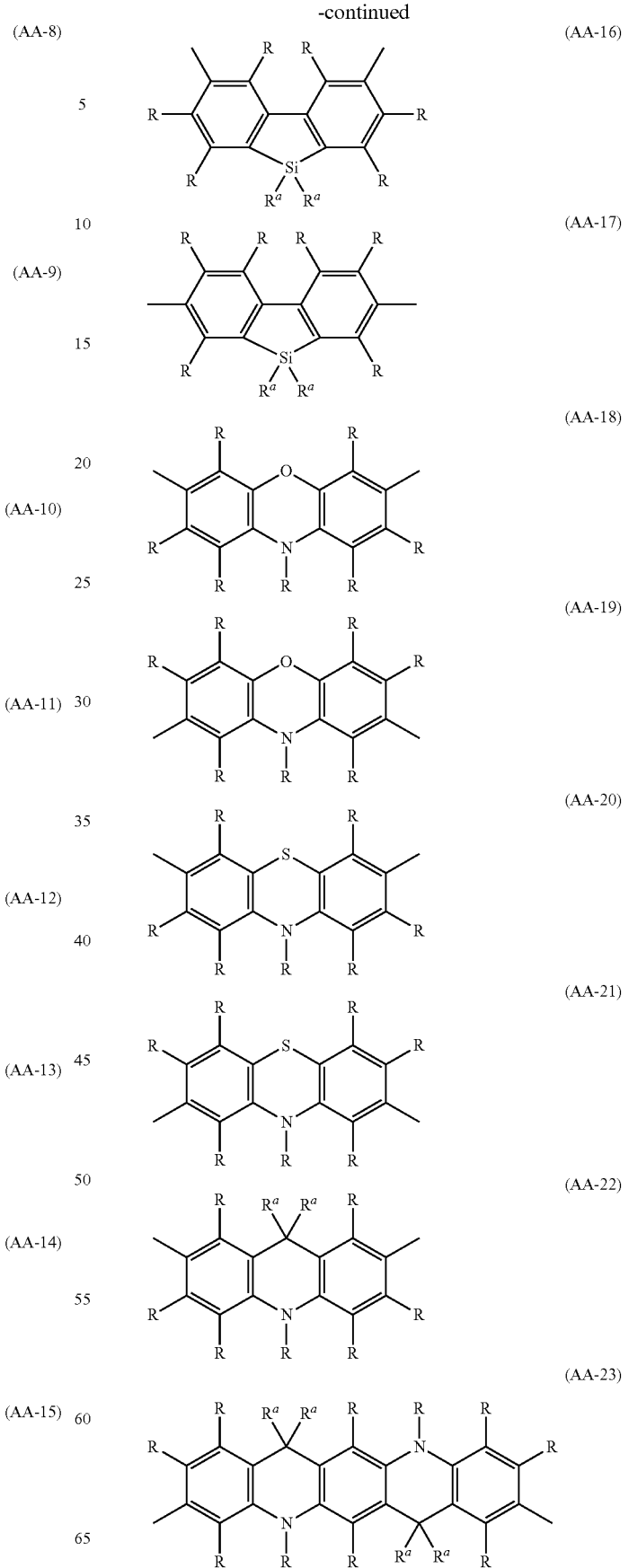

(AA-24)
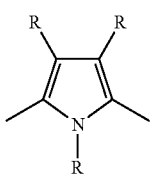

(AA-25)
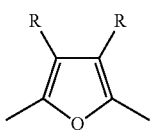

(AA-26)
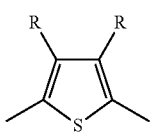

(AA-27)
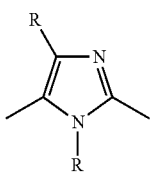

(AA-28)
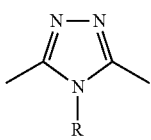

(AA-29)
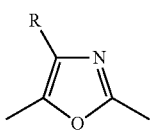

(AA-30)
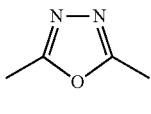

(AA-31)
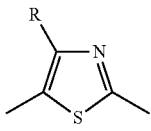

(AA-32)
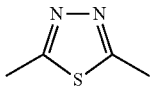

(AA-33)
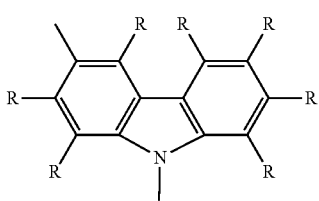

(AA-34)
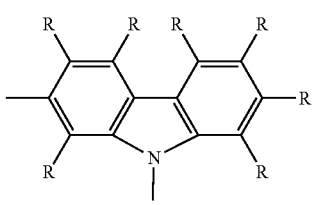

[wherein, R and $R^a$ represent the same meaning as described above.]

"Crosslinkable group" is a group capable of forming a new bond by being subjected to a heating treatment, an ultraviolet irradiation treatment, a radical reaction and the like, and cross-linkable groups are preferably groups represented by the formulae (XL-1) to (XL-17) of Group A of crosslinkable group.

(Group A of Crosslinkable Group)

(XL-1)

(XL-2)
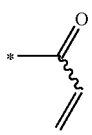

(XL-3)
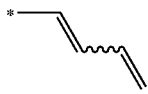

(XL-4)

(XL-5)

(XL-6)
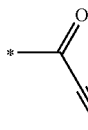

(XL-7)
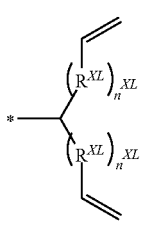

-continued

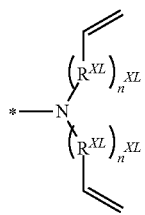 (XL-8)

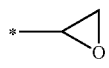 (XL-9)

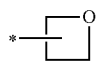 (XL-10)

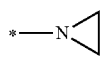 (XL-11)

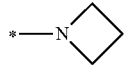 (XL-12)

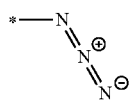 (XL-13)

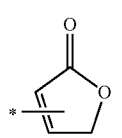 (XL-14)

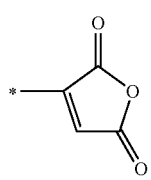 (XL-15)

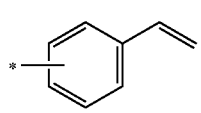 (XL-16)

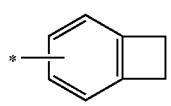 (XL-17)

[wherein, $R^{XL}$ represents a methylene group, an oxygen atom or a sulfur atom, and $n^{XL}$ represents an integer of 0 to 5. When a plurality of $R^{XL}$ are present, they may be the same or different, and when a plurality of $n^{XL}$ are present, they may be the same or different.

\* represents a binding position.

These crosslinkable groups each optionally have a substituent.].

"Substituent" represents a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group or a cycloalkynyl group. The substituent may be a crosslinkable group.

<Polymer Compound>
[Group Represented by Formula (1)]

The polymer compound of the present invention comprises a constitutional unit having a group represented by the formula (1).

Ring $R^{1A}$ and Ring $R^{2A}$ are preferably an aromatic hydrocarbon ring optionally having a substituent, because a light emitting device produced by using the polymer compound of the present invention is more excellent in light emission efficiency.

The aromatic hydrocarbon ring represented by Ring $R^{1A}$ and Ring $R^{2A}$ is preferably a 6-membered aromatic hydrocarbon ring, more preferably a benzene ring, a naphthalene ring or a fluorene ring, further preferably a benzene ring, and these rings each optionally have a substituent.

The heterocyclic ring represented by Ring $R^{1A}$ and Ring $R^{2A}$ is preferably a 5-membered or 6-membered aromatic heterocyclic ring, more preferably a thiophene ring, a furan ring, a pyrrole ring, a dibenzothiophene ring, a dibenzofuran ring, a carbazole ring, a pyridine ring or a pyrimidine ring, further preferably a thiophene ring, a carbazole ring or a pyridine ring, and these rings each optionally have a substituent.

The substituent which the ring represented by Ring $R^{1A}$ and Ring $R^{2A}$ optionally has is preferably an alkyl group, a cycloalkyl group or an aryl group.

Ring $R^{1A}$ and Ring $R^{2A}$ are preferably the same ring, because production of the polymer compound of the present invention is easy.

The content of the constitutional unit having a group represented by the formula (1) is preferably 3 to 90 mol %, more preferably 3 to 70 mol %, further preferably 3 to 50 mol % with respect to the total content of constitutional units contained in the polymer compound.

Ring $R^{1A}$ and Ring $R^{2A}$ are particularly preferably a benzene ring optionally having a substituent.

nA is preferably an integer of 0 to 3, more preferably 0 or 1, further preferably 0, because a light emitting device produced by using the polymer compound of the present invention is more excellent in light emission efficiency.

nB is preferably an integer of 1 to 3, more preferably 1 or 2, further preferably 1, because a light emitting device produced by using the polymer compound of the present invention is more excellent in light emission efficiency.

$L^A$ and $L^B$ are preferably an alkylene group, a cycloalkylene group, an arylene group or a divalent heterocyclic ring group, more preferably an alkylene group or an arylene group, further preferably an alkylene group, and these groups each optionally have a substituent, because a light emitting device produced by using the polymer compound of the present invention is more excellent in light emission efficiency.

The number of carbon atoms of the alkylene group represented by $L^A$ and $L^B$ is usually 1 to 10, preferably 1 to 8, more preferably 1 to 6, not including the number of carbon atoms of a substituent. The number of carbon atoms of the cycloalkylene group represented by $L^A$ and $L^B$ is usually 3 to 10, not including the number of carbon atoms of a substituent.

The alkylene group and the cycloalkylene group each optionally have a substituent and include, for example, a methylene group, an ethylene group, a propylene group, a butylene group, a hexylene group, a cyclohexylene group and an octylene group.

The arylene group represented by $L^A$ and $L^B$ optionally has a substituent and includes, for example, an o-phenylene group, a m-phenylene group and a p-phenylene group.

The substituent which the group represented by $L^A$ and $L^B$ optionally has is preferably an alkyl group, a cycloalkyl group or an aryl group.

When a plurality of $L^A$ are present, they may be the same or different, and it is preferable that they are the same group or atom because production of the polymer compound of the present invention is easy.

When a plurality of $L^B$ are present, they may be the same or different, and it is preferable that they are the same group or atom because production of the polymer compound of the present invention is easy.

When a plurality of $L^A$ are present, two or more $L^A$s may be a group represented by —NR'—, and it is preferable that groups represented by —NR'— are not adjacent.

When a plurality of $L^B$ are present, two or more $L^B$s may be a group represented by —NR'—, and it is preferable that groups represented by —NR'— are not adjacent.

When a plurality of $L^A$ are present, two or more $L^A$s may be an oxygen atom or a sulfur atom, and it is preferable that these atoms are not adjacent.

When a plurality of $L^B$ are present, two or more $L^B$s may be an oxygen atom or a sulfur atom, and it is preferable that these atoms are not adjacent.

$Q^1$ is usually a crosslinkable group selected from Group A of crosslinkable group, and is preferably a crosslinkable group selected from Group A' of crosslinkable group, more preferably a crosslinkable group represented by the formula (XL-1), the formula (XL-3), the formula (XL-5), the formula (XL-7), the formula (XL-16) or the formula (XL17), further preferably a crosslinkable group represented by the formula (XL-3), the formula (XL-5), the formula (XL-7) or the formula (XL-17), particularly preferably a crosslinkable group represented by the formula (XL-17), because the crosslinkability of the polymer compound of the present invention is excellent.

The group represented by the formula (1) includes, for example, groups represented by the formula (1-1) to the formula (1-22), and is preferably a constitutional unit represented by the formula (1-1) to the formula (1-14) or the formula (1-19) to the formula (1-21), more preferably a group represented by the formula (1-1) to the formula (1-6), the formula (1-19) or the formula (1-20).

TABLE 1

| formula | $R^{1A}$, $R^{2A}$ core | $Q^1$ | $(L^A)_{nA}$ | $(L^B)_{nB}$ |
|---|---|---|---|---|
| (1-1) | fluorene | benzocyclobutene | none | $*-(CH_2)_3-*$ |
| (1-2) | fluorene | benzocyclobutene | none | $*-CH_2-C(Me)_2-CH_2-*$ |
| (1-3) | fluorene | benzocyclobutene | 1,4-phenylene | $*-(CH_2)_6-*$ |
| (1-4) | fluorene | benzocyclobutene | 1,3-phenylene | $*-(CH_2)_6-*$ |
| (1-5) | fluorene | benzocyclobutene | 4,4'-biphenylene | $*-(CH_2)_6-*$ |

TABLE 1-continued
| formula | (R1A, R2A ring) | Q1 | (LA)nA | (LB)nB |
|---|---|---|---|---|
| (1-6) | 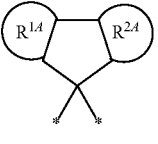 | 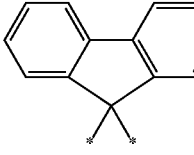 | 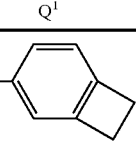 | 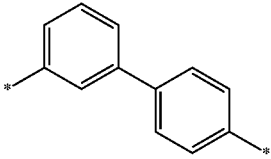 |
| (1-7) | 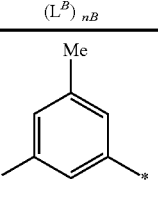 | 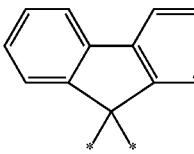 | *—(CH$_2$)$_4$—* |  |
| (1-8) | 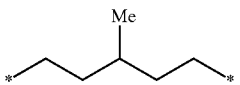 | 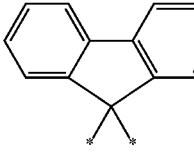 | none | 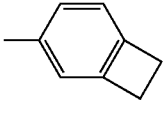 |
| (1-9) | 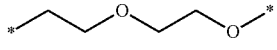 | 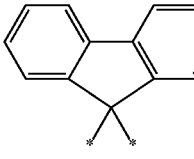 | none | 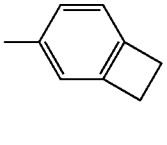 |
| (1-10) | 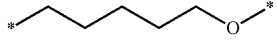 | 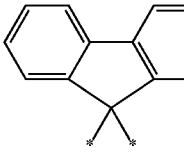 | 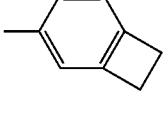 | *—(CH$_2$)$_3$—* |
TABLE 2
| formula | (R1A, R2A ring) | Q1 | (LA)nA | (LB)nB |
|---|---|---|---|---|
| (1-11) | 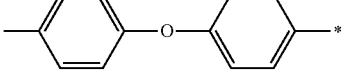 | 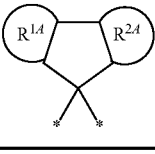 | 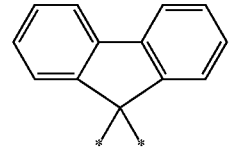 | 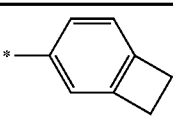 |
| (1-12) | 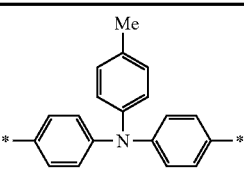 | 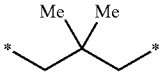 | *—(CH$_2$)$_2$—* | *—(CH$_2$)$_3$—* |

TABLE 2-continued
| formula | 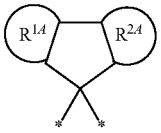 | Q¹ | $(L^A)_{nA}$ | $(L^B)_{nB}$ |
|---|---|---|---|---|
| (1-13) | 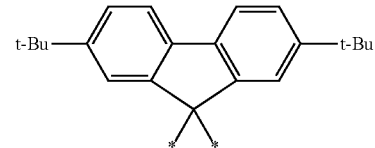 | 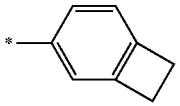 | none | *—(CH$_2$)$_6$—* |
| (1-14) | 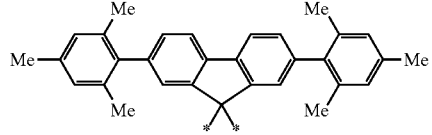 | 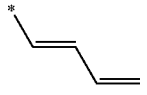 | *—(CH$_2$)$_2$—* | *—(CH$_2$)$_3$—* |
| (1-15) | 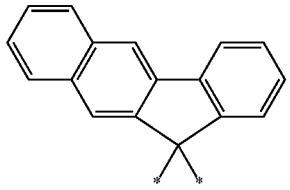 |  | *—(CH$_2$)$_4$—* | *—(CH$_2$)$_3$—* |
| (1-16) | 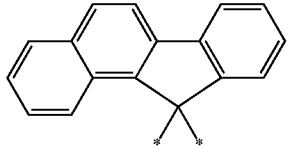 | 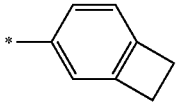 | none | 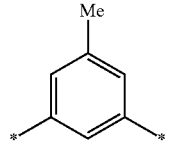 |
| (1-17) | 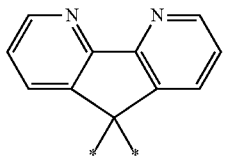 | 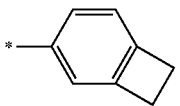 | 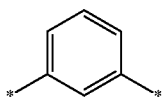 | 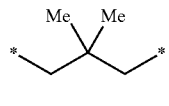 |
| (1-18) | 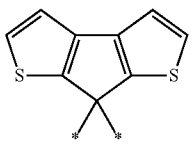 | 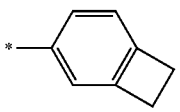 | none | *—(CH$_2$)$_4$—* |
TABLE 3
| formula | 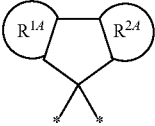 | Q¹ | $(L^A)_{nA}$ | $(L^B)_{nB}$ |
|---|---|---|---|---|
| (1-19) | 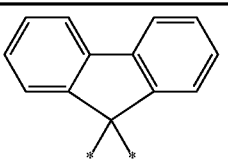 | 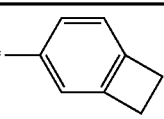 | none | *—(CH$_2$)$_6$—* |

TABLE 3-continued

| formula | 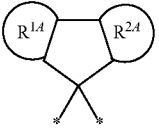 | $Q^1$ | $(L^A)_{nA}$ | $(L^B)_{nB}$ |
|---|---|---|---|---|
| (1-20) | 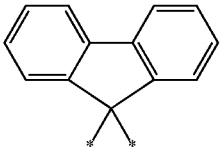 | 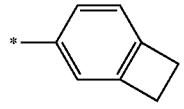 | 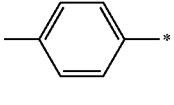 | *—(CH$_2$)$_{\overline{3}}$—* |
| (1-21) | 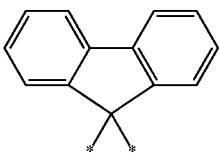 | 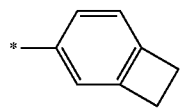 | *—(CH$_2$)$_{\overline{4}}$—* | 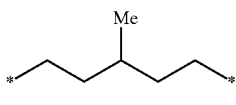 |
| (1-22) | 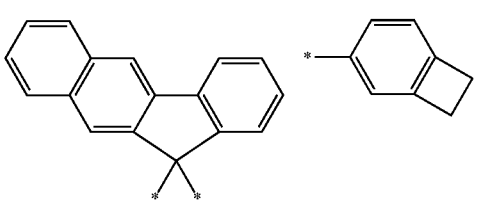 | 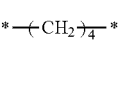 | *—(CH$_2$)$_{\overline{4}}$—* | *—(CH$_2$)$_{\overline{3}}$—* |

[wherein, * represents a binding position.]

The constitutional unit having a group represented by the formula (1) is preferably a constitutional unit represented by the formula (2) described later, and may also be a constitutional unit represented by the following formula.

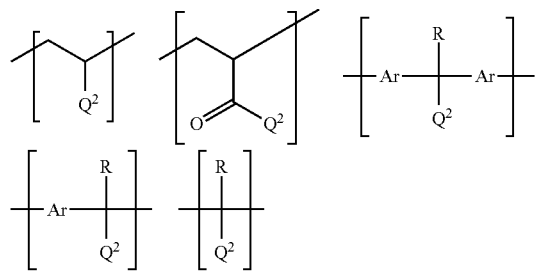

[wherein, $Q^2$ represents a group represented by the formula (1). Ar represents the same meaning as that of the formula $Ar^{X1}$, and R represents the same meaning as above.]

The constitutional unit having a group represented by the formula (1) may be contained only singly, or two or more of the constitutional units may be contained, in the polymer compound.

[Constitutional Unit Represented by the Formula (2)]

The constitutional unit having a group represented by the formula (1) is preferably a constitutional unit represented by the formula (2), because the light emitting device of the present invention is more excellent in light emission efficiency.

$Ar^1$ is preferably an aromatic hydrocarbon group optionally having a substituent, because a light emitting device produced by using the polymer compound of the present invention is more excellent in light emission efficiency.

The number of carbon atoms of the aromatic hydrocarbon group represented by $Ar^1$ is usually 6 to 60, preferably 6 to 30, more preferably 6 to 18, not including the number of carbon atoms of a substituent.

The arylene group portion obtained by removing n substituents of the aromatic hydrocarbon group represented by $Ar^1$ is preferably a group represented by the formula (A-1) to the formula (A-20), more preferably a group represented by the formula (A-1), the formula (A-2), the formula (A-6) to the formula (A-10), the formula (A-19) or the formula (A-20), further preferably a group represented by the formula (A-1), the formula (A-2) or the formula (A-9), and these groups each optionally have a substituent.

The number of carbon atoms of the heterocyclic ring group represented by $Ar^1$ is usually 6 to 60, preferably 6 to 30, more preferably 6 to 18, not including the number of carbon atoms of a substituent.

The divalent heterocyclic ring group portion obtained by removing n substituents of the heterocyclic ring group represented by $Ar^1$ is preferably a group represented by the formula (AA-1) to the formula (AA-34).

$Ar^1$ is preferably a group obtained by removing from a benzene ring optionally having a substituent, a fluorene ring optionally having a substituent, a naphthalene ring optionally having a substituent, a phenanthrene ring optionally having a substituent or a dihydrophenanthrene ring optionally having a substituent (2+n) hydrogen atoms linked directly to carbon atoms constituting the ring, more preferably a group obtained by removing from a benzene ring optionally having a substituent, a fluorene ring optionally having a substituent, a naphthalene ring optionally having a substituent, a phenanthrene ring optionally having a substituent or a dihydrophenanthrene ring optionally having a substituent (2+n) hydrogen atoms linked directly to carbon atoms constituting the ring, further preferably a group obtained by removing from a benzene ring optionally having a substituent (2+n) hydrogen atoms linked directly to carbon atoms constituting the ring, because a light emitting device produced by using the polymer compound of the present invention is excellent in light emission efficiency.

The aromatic hydrocarbon group and the heterocyclic ring group represented by $Ar^1$ each optionally have a substituent, and the substituent includes an alkyl group, a cycloalkyl group, an alkoxyl group, a cycloalkoxy group, an aryl group, an aryloxy group, a halogen atom, a monovalent heterocyclic group and a cyano group.

n is preferably 1 or 2, because synthesis of the polymer compound of the present invention is easy and because a light emitting device produced by using the polymer compound of the present invention is more excellent in light emission efficiency.

$Q^2$ represents a group represented by the formula (1). When a plurality of $Q^2$ are present, they may be the same or different, and it is preferable that they are the same group because production of the polymer compound of the present invention is easy.

The content of the constitutional unit represented by the formula (2) is preferably 3 to 90 mol %, more preferably 3 to 70 mol %, further preferably 3 to 50 mol % with respect to the total content of constitutional units contained in the polymer compound, because the polymer compound of the present invention is excellent in stability.

The constitutional unit represented by the formula (2) includes, for example, constitutional units represented by the formula (2-1) to the formula (2-20), and is preferably a constitutional unit represented by the formula (2-1) to the formula (2-9) or the formula (2-13) to the formula (2-18), more preferably a constitutional unit represented by the formula (2-1) to the formula (2-3) or the formula (2-13) to the formula (2-17), further preferably a constitutional unit represented by the formula (2-1) or the formula (2-13) to the formula (2-17).

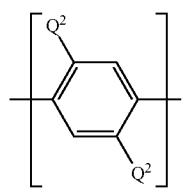

(2-1)

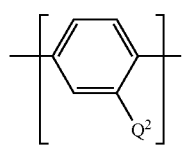

(2-2)

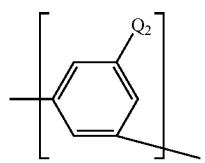

(2-3)

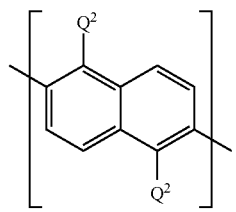

(2-4)

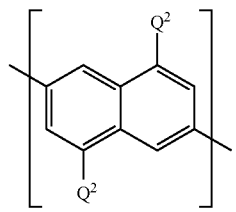

(2-5)

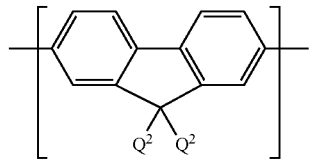

(2-6)

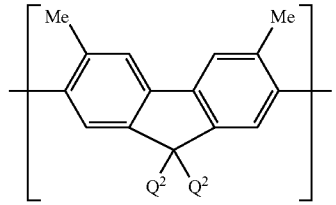

(2-7)

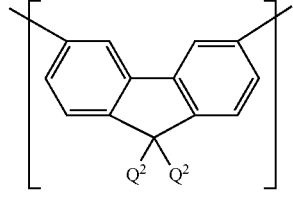

(2-8)

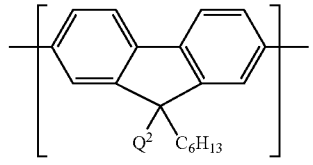

(2-9)

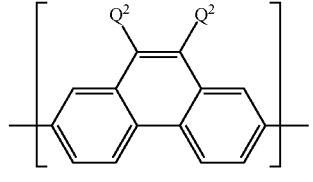

(2-10)

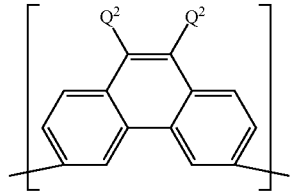

(2-11)

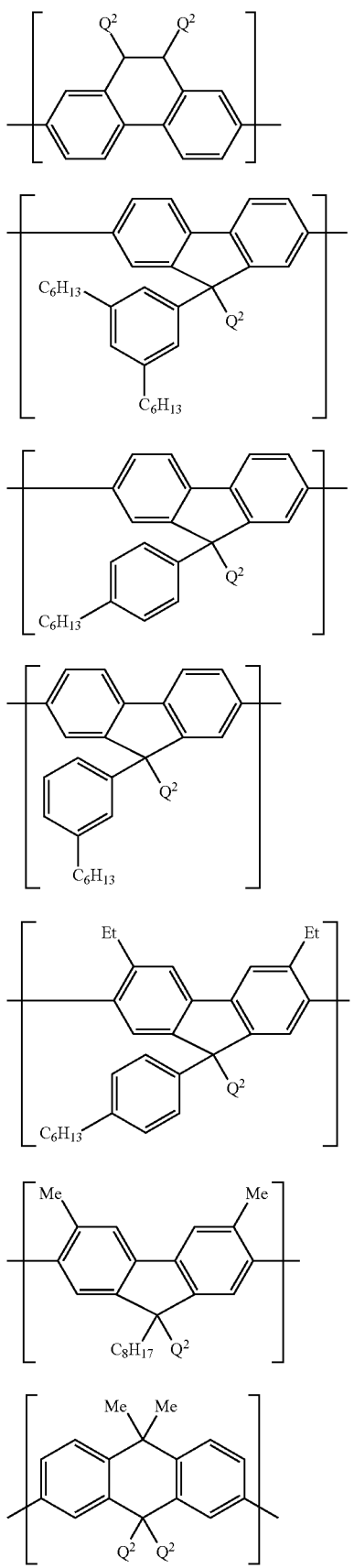

(2-12)
(2-13)
(2-14)
(2-15)
(2-16)
(2-17)
(2-18)

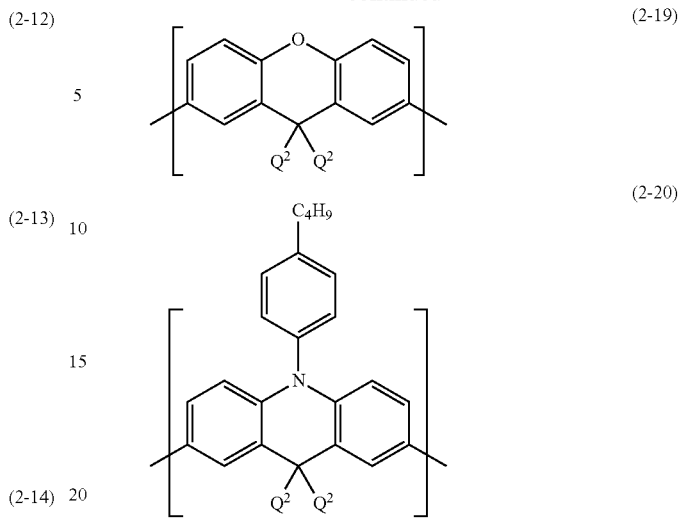

(2-19)
(2-20)

[wherein, $Q^2$ represents the same meaning as described above.]

The constitutional unit represented by the formula (2) may be contained only singly or two or more of the constitutional units may be contained in the polymer compound.

[Other Constitutional Unit]

It is preferable that the polymer compound of the present invention further comprises a constitutional unit represented by the formula (X), because hole transportability is excellent.

$a^{X1}$ is preferably an integer of 0 to 2 (2 or less), more preferably because the luminance life of a light emitting device produced by using the polymer compound of the present invention is excellent.

$a^{X2}$ is preferably an integer of 0 to 2 (2 or less), more preferably 0, because the luminance life of a light emitting device produced by using the polymer compound of the present invention is excellent.

$R^{X1}$, $R^{X2}$ and $R^{X3}$ are preferably an alkyl group, a cycloalkyl group, an aryl group or a monovalent heterocyclic group, more preferably an aryl group, and these groups each optionally have a substituent.

The arylene group represented by $Ar^{X1}$ and $Ar^{X3}$ is more preferably a group represented by the formula (A-1) or the formula (A-9), further preferably a group represented by the formula (A-1), and these groups each optionally have a substituent.

The divalent heterocyclic group represented by $Ar^{X1}$ and $Ar^{X3}$ is more preferably a group represented by the formula (AA-1), the formula (AA-2) or the formula (AA-7) to (AA-26), and these groups each optionally have a substituent.

$Ar^{X1}$ and $Ar^{X3}$ are preferably an arylene group optionally having a substituent.

The arylene group represented by $Ar^{X2}$ and $Ar^{X4}$ is more preferably a group represented toy the formula (A-1), the formula (A-6), the formula (A-7), the formulae (A-9) to (A-11) or the formula (A-19), and these groups each optionally have a substituent.

The more preferable range of the divalent heterocyclic group represented by $Ar^{X2}$ and $Ar^{X4}$ is the same as the more preferable range of the divalent heterocyclic group represented by $Ar^{X1}$ and $Ar^{X3}$.

The more preferable range and the further preferable range of the arylene group and the divalent heterocyclic group in the divalent group in which at least one arylene group and at least one divalent heterocyclic group are bonded directly to each other represented by $Ar^{X2}$ and $Ar^{X4}$ are the same as the more preferable range and the further preferable range of the arylene group and the divalent heterocyclic group represented by $Ar^{X1}$ and $Ar^{X3}$, respectively.

The divalent group in which at least one arylene group and at least one divalent heterocyclic group are bonded directly to each other represented by $Ar^{X2}$ and $Ar^{X4}$ includes, for example, groups represented by the following formulae, and they each optionally have a substituent.

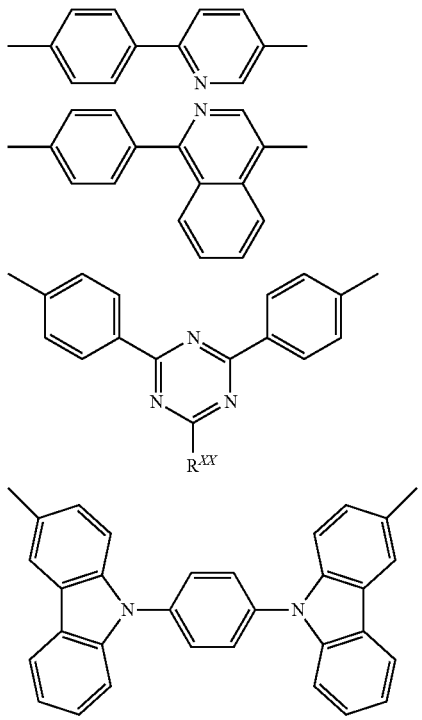

[wherein, $R^{XX}$ represents a hydrogen atom, an alkyl group, a cycloalkyl group, an aryl group or a monovalent heterocyclic group, and these groups each optionally have a substituent.]

$R^{XX}$ is preferably an alkyl group, a cycloalkyl group or an aryl group, and these groups each optionally have a substituent.

$Ar^{X2}$ and $Ar^{X4}$ are preferably an arylene group optionally having a substituent.

The substituent which the group represented by $Ar^{X1}$ to $Ar^{X4}$ and $R^{X1}$ to $R^{X3}$ to optionally has is preferably an alkyl group, a cycloalkyl group or an aryl group, and these groups each optionally further have a substituent.

The constitutional unit represented by the formula (X) is preferably a constitutional unit represented by the formula (X-1) to (X-7), more preferably a constitutional unit represented by the formula (X-3) to (X-7), further preferably a constitutional unit represented by the formula (X-3) to (X-6).

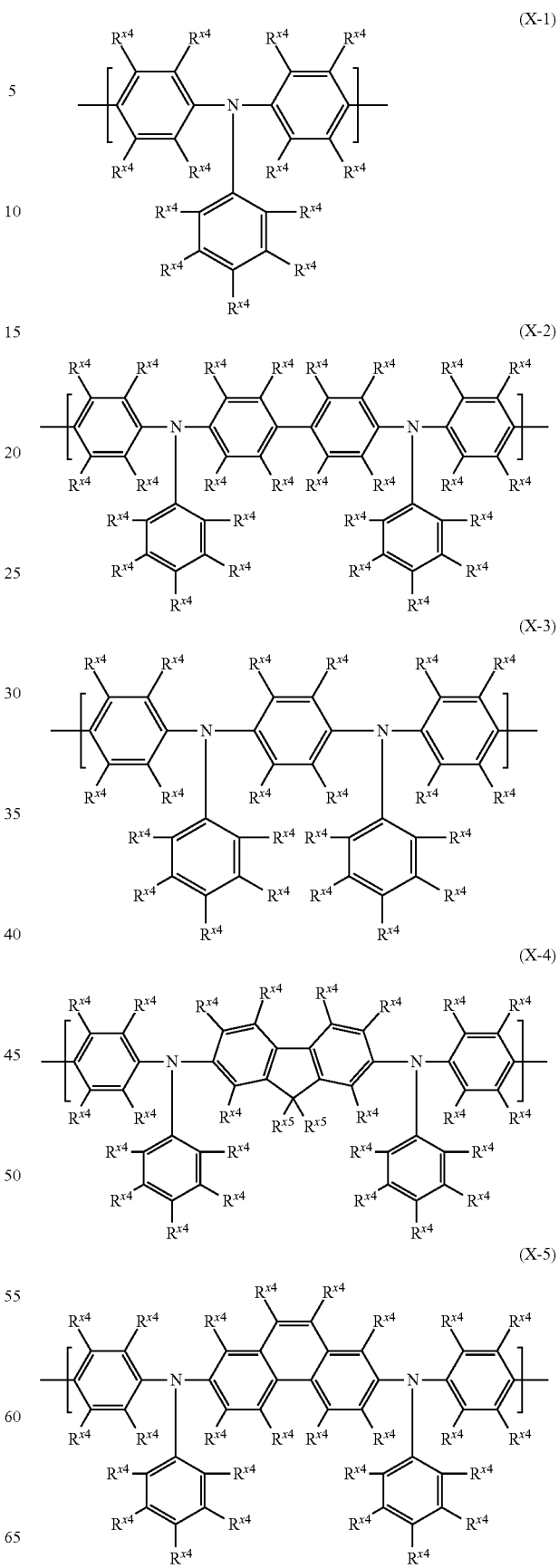

(X-6)

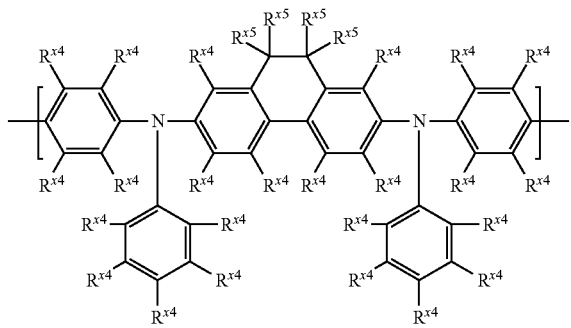

(X-7)

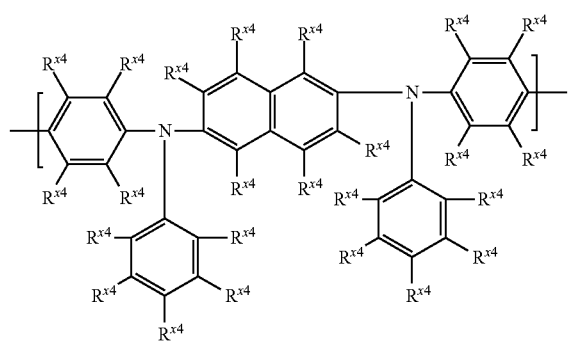

[wherein, $R^{X4}$ and $R^{X5}$ each independently represent a hydrogen atom, an alkyl group, a cycloalkyl group, an alkoxy group, a cycloalkoxy group, an aryl group, an aryloxy groups a halogen atom, a monovalent heterocyclic group or a cyano group and these groups each optionally have a substituent. The plurality of $R^{X4}$ may be the same or different. The plurality of $R^{X5}$ may be the same or different, and adjacent groups $R^{X5}$ may be combined together to form a ring together with the carbon atoms to which they are attached.]

The content of the constitutional unit represented by the formula (X) is preferably 0.1 to 90 mol %, more preferably 1 to 70 mol %, further preferably 5 to 50 mol % with respect to the total content of constitutional units contained in the polymer compound, because hole transportability is excellent.

The constitutional unit represented by the formula (X) includes, for example, constitutional units represented by the formulae (X1-1) to (X1-19), preferably constitutional units represented by the formulae (X1-6) to (X1-14).

(X1-1)

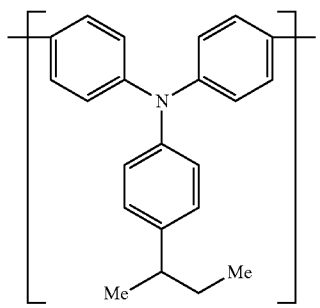

(X1-2)

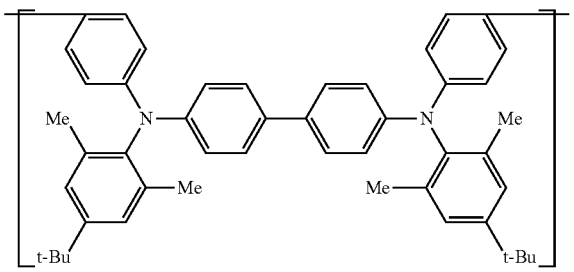

(X1-3)

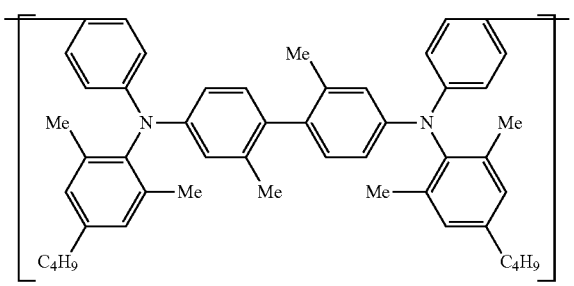

(X1-4)

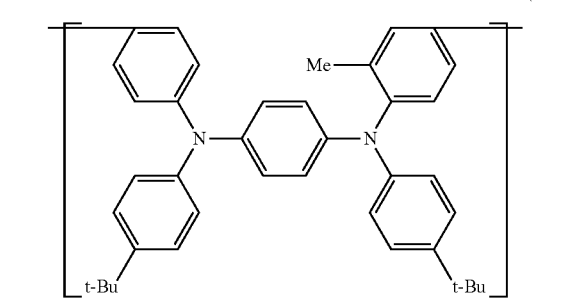

(X1-5)

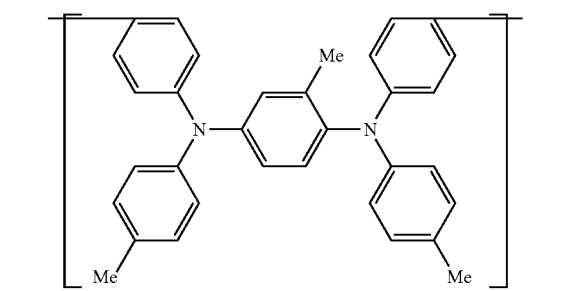

(X1-6)

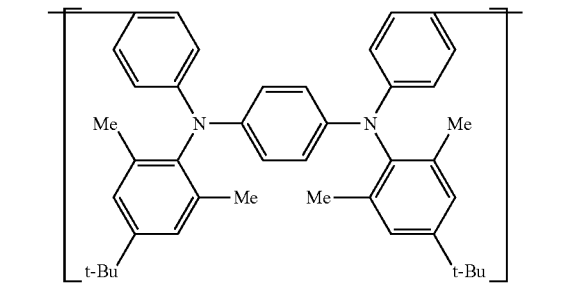

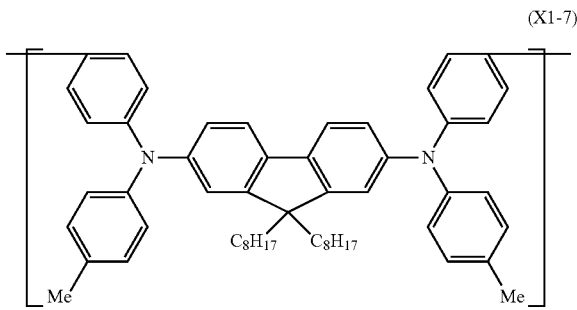
(X1-7)
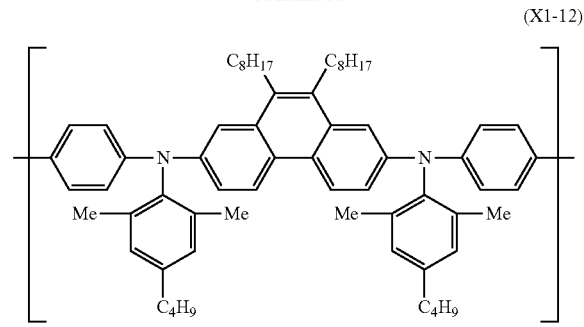
(X1-12)
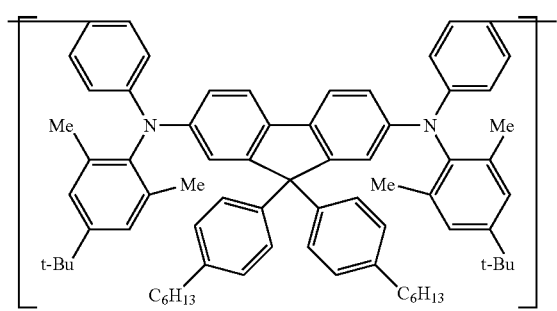
(X1-8)
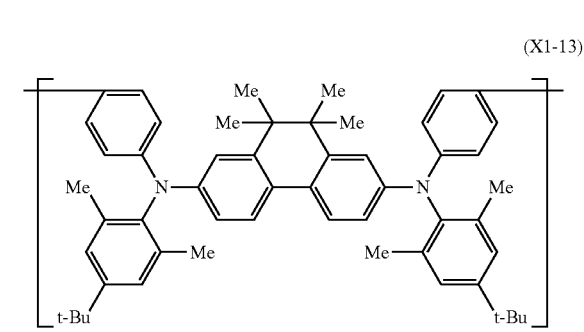
(X1-13)
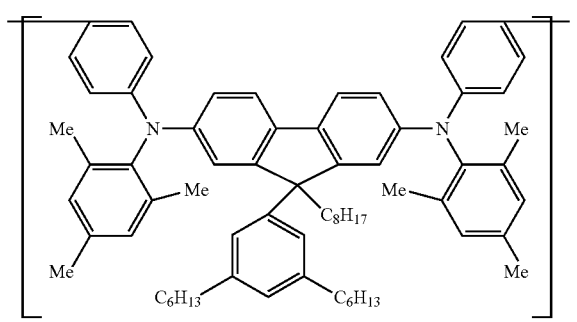
(X1-9)
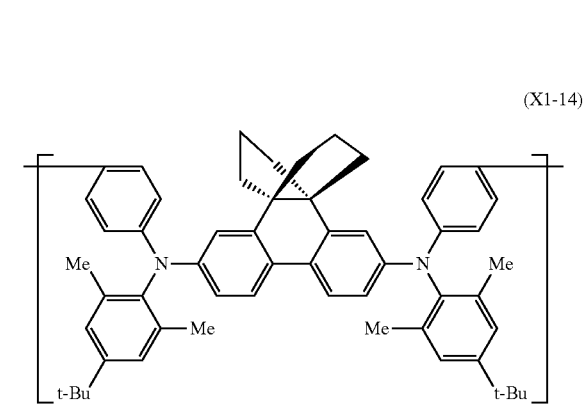
(X1-14)
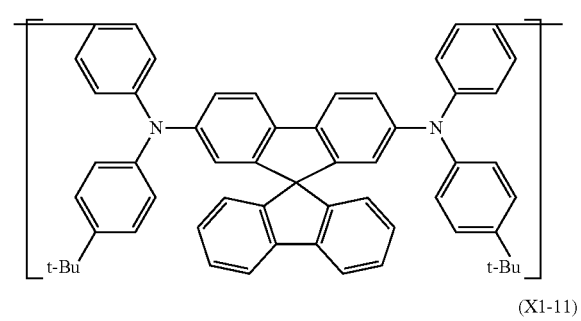
(X1-10)
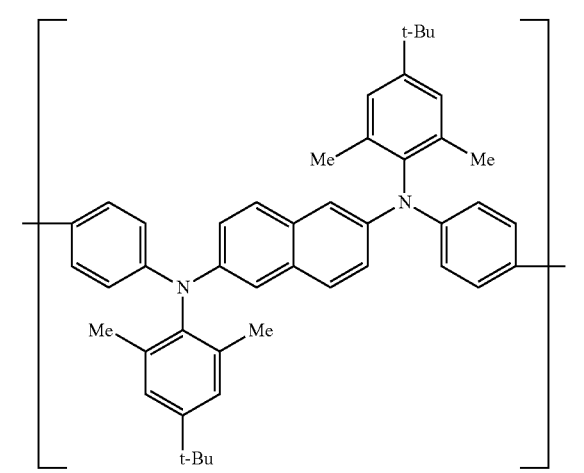
(X1-15)
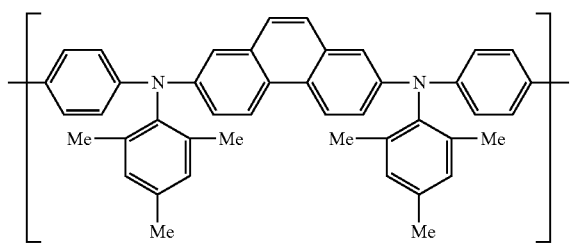
(X1-11)

-continued

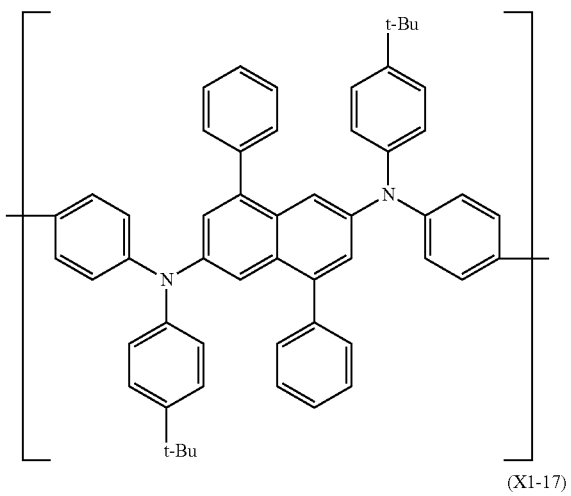
(X1-16)

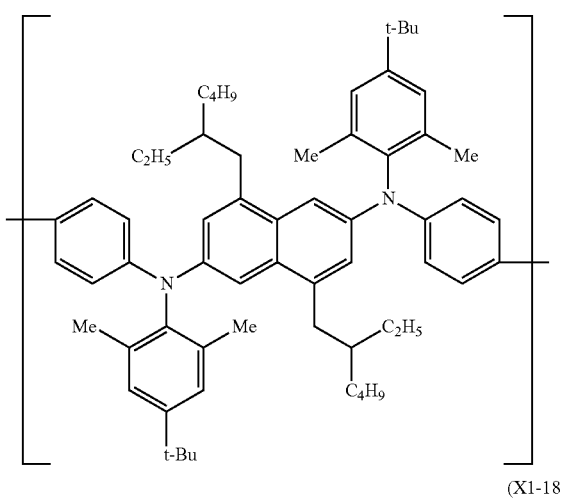
(X1-17)

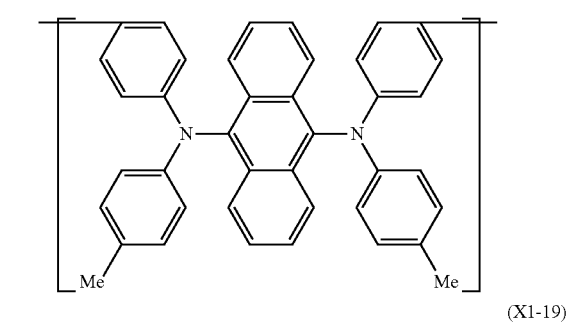
(X1-18)

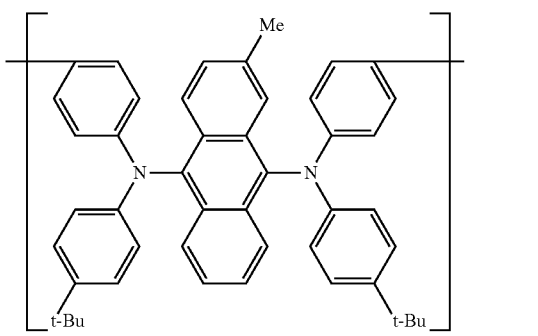
(X1-19)

The constitutional unit represented by the formula (X) may be contained only singly or two or more units thereof may be contained in the polymer compound of the present invention.

It is preferable that the polymer compound of the present invention further comprises a constitutional unit represented by the formula (Y), because the luminance life of a light emitting device produced by using the polymer compound of the present invention is excellent.

It is preferable that the polymer compound of the present invention further comprises a constitutional unit represented by the formula (X) and a constitutional unit represented by the formula (Y), because the light emission efficiency of a light emitting device produced by using the polymer compound of the present invention is excellent.

The arylene group represented by $Ar^{Y1}$ is more preferably a group represented by the formula (A-1), the formula (A-6), the formula (A-7), the formula (A-9) to (A-11), the formula (A-13) or the formula (A-19), further preferably a group represented by the formula (A-1), the formula (A-7), the formula (A-9) or the formula (A-19), and these groups each optionally have a substituent.

The divalent heterocyclic group represented by $Ar^{Y1}$ is more preferably a group represented by the formula (AA-4), the formula (AA-10), the formula (AA-13), the formula (AA-15), the formula (AA-18) or the formula (AA-20), further preferably a group represented by the formula (AA-4), the formula (AA-10), the formula (AA-18) or the formula (AA-20), and these groups each optionally have a substituent.

The more preferable range and the further preferable range of the arylene group and the divalent heterocyclic group in the divalent group in which at least one arylene group and at least one divalent heterocyclic group are bonded directly to each other represented by $Ar^{Y1}$ are the same as the more preferable range and the further preferable range of the arylene group and the divalent heterocyclic group represented by $Ar^{Y1}$ described above, respectively.

The divalent group in which at least one arylene group and at least one divalent heterocyclic group are bonded directly to each other represented by $Ar^{Y1}$ includes the same groups as the divalent group in which at least one arylene group and at least one divalent heterocyclic group are bonded directly to each other represented by $Ar^{X2}$ and $Ar^{X4}$ in the formula (X).

The substituent which the group represented by $Ar^{Y1}$ optionally has is preferably an alkyl group, a cycloalkyl group or an aryl group, and these groups each optionally further have a substituent.

The constitutional unit represented by the formula (Y) includes, for example, constitutional units represented by the formulae (Y-1) to (Y-7), and from the standpoint of the luminance life of a light emitting device produced by using the polymer compound of the present invention preferable is a constitutional unit represented by the formula (Y-1) or (Y-2), from the standpoint of electron transportability preferable is a constitutional unit represented by the formula (Y-3) or (Y-4), and from the standpoint of hole transportability preferable are constitutional units represented by the formulae (Y-5) to (Y-7).

$R^{Y1}$ is preferably a hydrogen atom, an alkyl group, a cycloalkyl group or an aryl group, and these groups each optionally have a substituent.

The constitutional unit represented fey the formula (Y-1) is preferably a constitutional unit represented by the formula (Y-1').

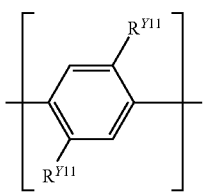

(Y-1')

[wherein, $R^{Y11}$ represents an alkyl group, a cycloalkyl group, an alkoxy group, a cycloalkoxy group, an aryl group or a monovalent heterocyclic group, and these groups each optionally have a substituent. The plurality of $R^{Y1}$ may be the same or different.]

$R^{Y11}$ is preferably an alkyl group, a cycloalkyl group or an aryl group, more preferably an alkyl group or a cycloalkyl group, and these groups each optionally have a substituent.

$R^{Y2}$ is preferably an alkyl group, a cycloalkyl group, an aryl group or a monovalent heterocyclic group, more preferably an alkyl group a cycloalkyl group or an aryl group, and these groups each optionally have a substituent.

Regarding the combination of two $R^{Y2}$s in the group represented by —C($R^{Y2}$)$_2$— in $X^{Y1}$, it is preferable that the both are an alkyl group or a cycloalkyl group, the both are an aryl group, the both are a monovalent heterocyclic group, or one is an alkyl group or a cycloalkyl group and the other is an aryl group or a monovalent heterocyclic group, it is more preferable that one is an alkyl group or cycloalkyl group and the other is an aryl group, and these groups each optionally have a substituent. The two groups $R^{Y2}$ may be combined together to form a ring together with the atoms to which they are attached, and when the groups $R^{Y2}$ form a ring, the group represented by —C($R^{Y2}$)$_2$— is preferably a group represented by the formula (Y-A1) to (Y-A5), more preferably a group represented by the formula (Y-A4), and these groups each optionally have a substituent.

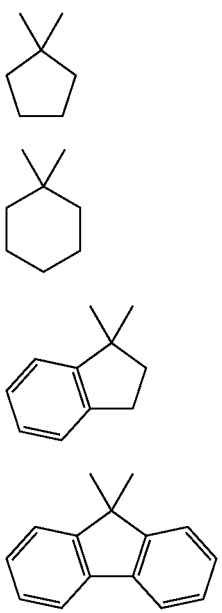

(Y-A1)

(Y-A2)

(Y-A3)

(Y-A4)

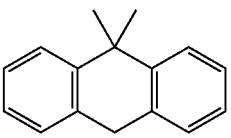

(Y-A5)

Regarding the combination of two $R^{Y2}$s in the group represented by —C($R^{Y2}$)=C($R^{Y2}$)— in $X^{Y1}$, it is preferable that the both are an alkyl group or cycloalkyl group, or one is an alkyl group or a cycloalkyl group and the other is an aryl group, and these groups each optionally have a substituent.

Four $R^{Y2}$s in the group represented by —C($R^{Y2}$)$_2$—C($R^{Y2}$)$_2$— in $X^{Y1}$ are preferably an alkyl group or a cycloalkyl group optionally having a substituent. The plurality of $R^{Y2}$ may be combined together to from a ring together with the atoms to which they are attached, and when the groups $R^{Y2}$ form a ring, the group represented by —C($R^{Y2}$)$_2$—C($R^{Y2}$)$_2$— is preferably a group represented by the formula (Y-B1) to (Y-B5), more preferably a group represented by the formula (Y-B3), and these groups each optionally have a substituent.

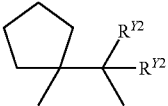

(Y-B1)

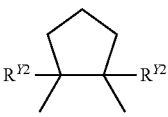

(Y-B2)

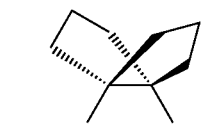

(Y-B3)

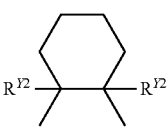

(Y-B4)

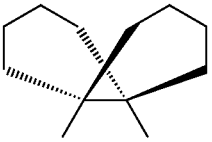

(Y-B5)

[wherein, $R^{Y2}$ represents the same meaning as described above.]

It is preferable that the constitutional unit represented by the formula (Y-2) is a constitutional unit represented by the formula (Y-2'),

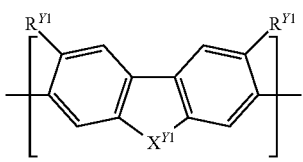
(Y-2′)

[wherein, $R^{Y1}$ and $X^{Y1}$ represent the same meaning as described above.]

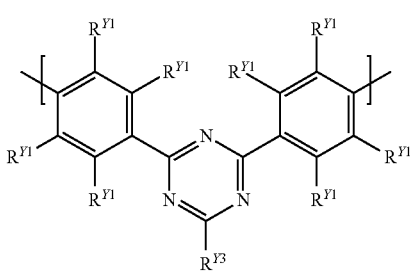
(Y-3)

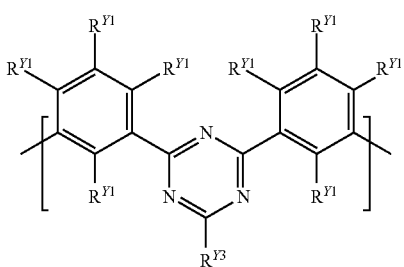
(Y-4)

[wherein, $R^{Y1}$ represents the same meaning as described above. $R^{Y3}$ represents a hydrogen atom, an alkyl group, a cycloalkyl group, an alkoxy group, a cycloalkoxy group, an aryl group or a monovalent heterocyclic group, and these groups each optionally have a substituent.]

$R^{Y3}$ is preferably an alkyl group, a cycloalkyl group, an alkoxy group, a cycloalkoxy group, an aryl group or a monovalent heterocyclic group, more preferably an aryl group, and these groups each optionally have a substituent.

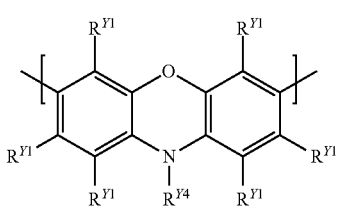
(Y-5)

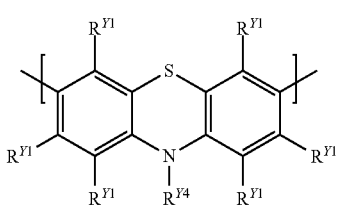
(Y-6)

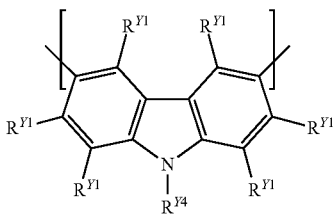
(Y-7)

[wherein, $R^{Y1}$ represents the same meaning as described above. $R^{Y4}$ represents a hydrogen atom, an alkyl group, a cycloalkyl group, an alkoxy group, a cycloalkoxy group, an aryl group or a monovalent heterocyclic group, and these groups each optionally have a substituent.]

$R^{Y4}$ is preferably an alkyl group, a cycloalkyl group, an alkoxy group, a cycloalkoxy group, an aryl group or a monovalent heterocyclic group, more preferably an aryl group, and these groups each optionally have a substituent.

The constitutional unit represented by the formula (Y) includes, for example, constitutional units represented by the formulae (Y-11) to (Y-55).

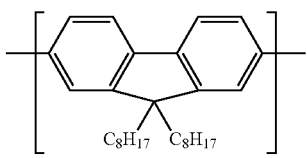
(Y-11)

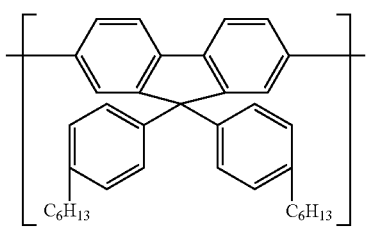
(Y-12)

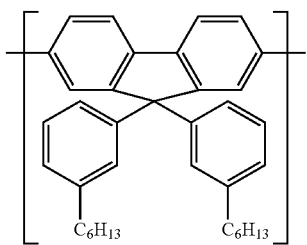
(Y-13)

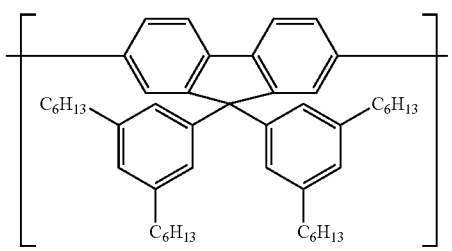
(Y-14)

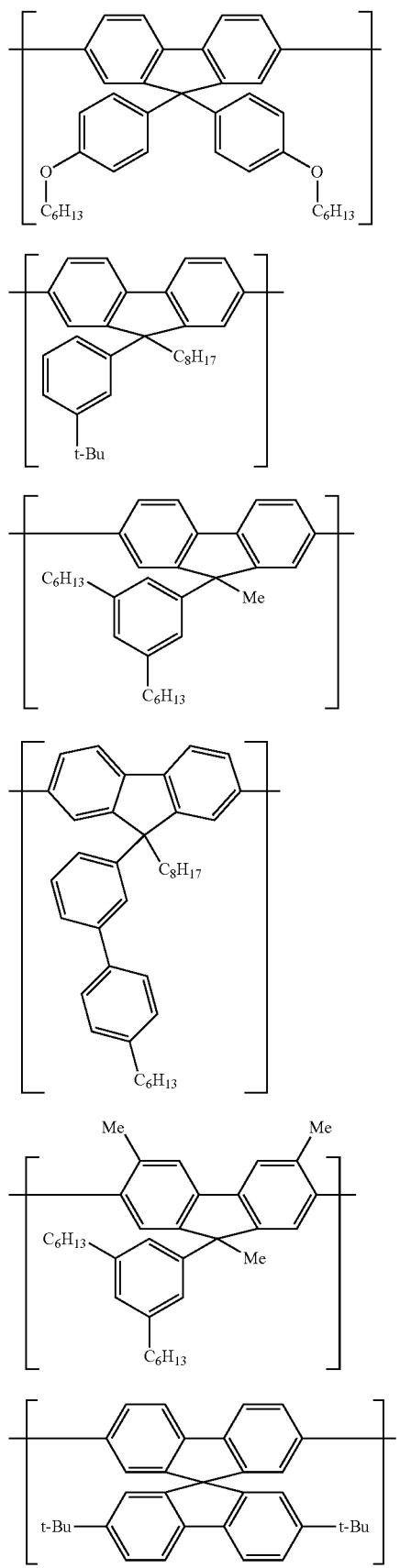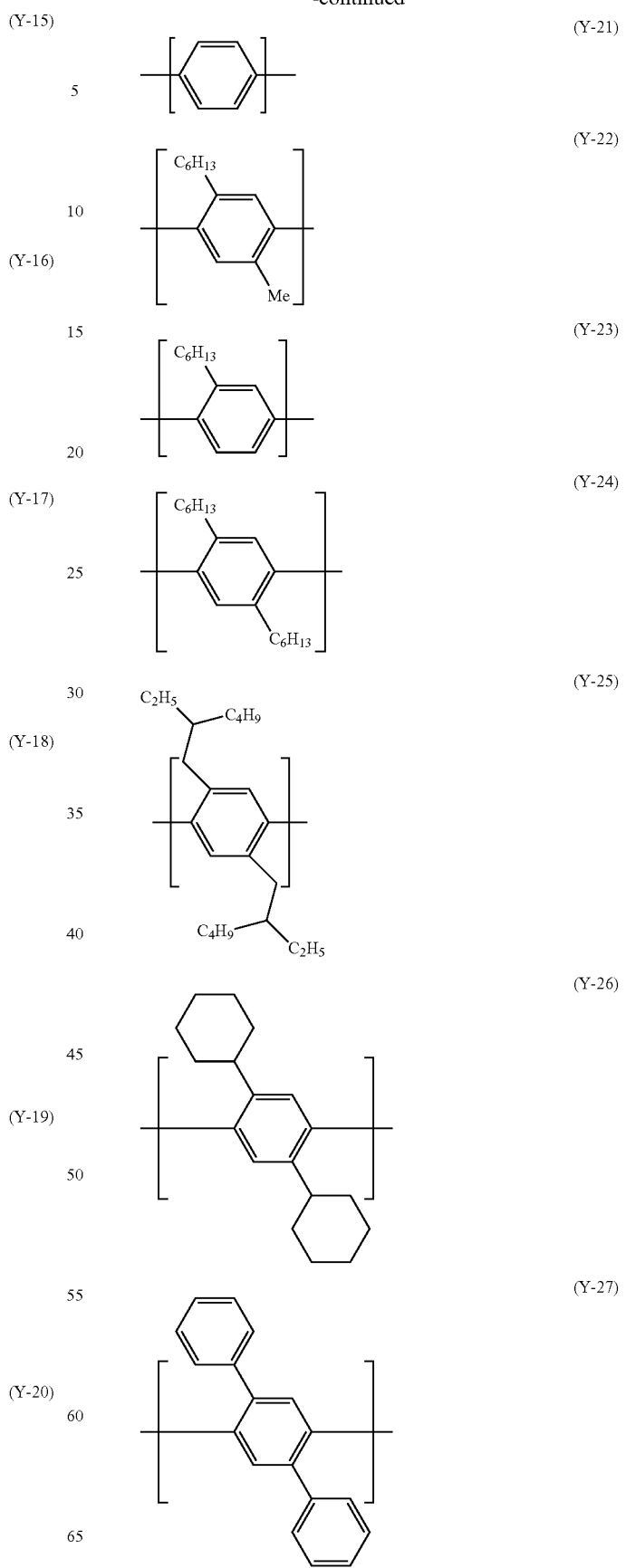

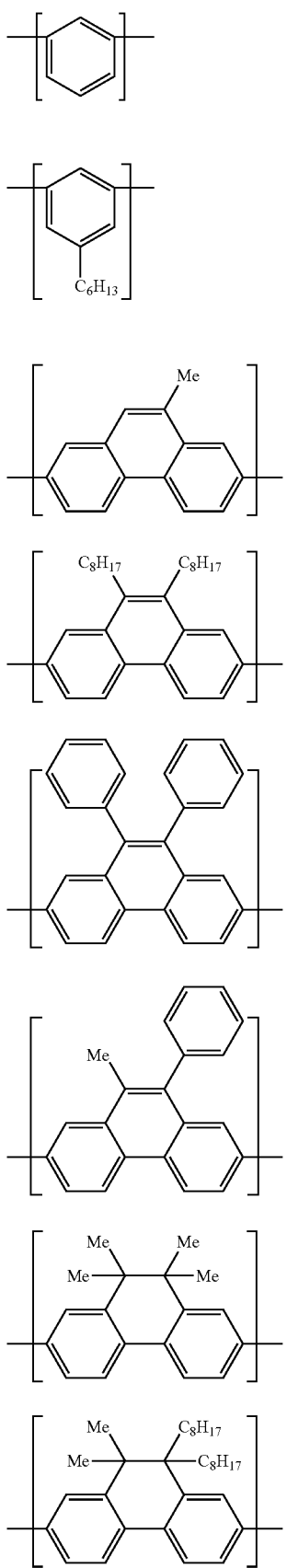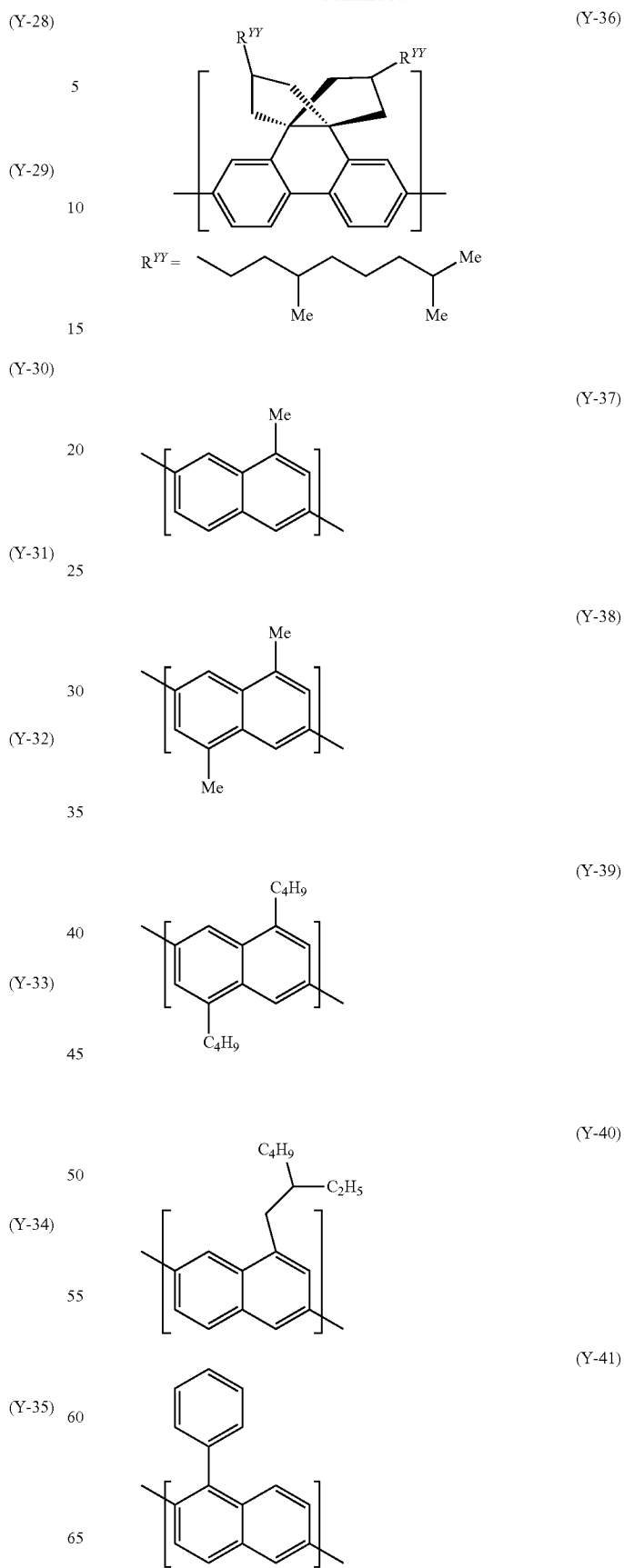

(Y-42) 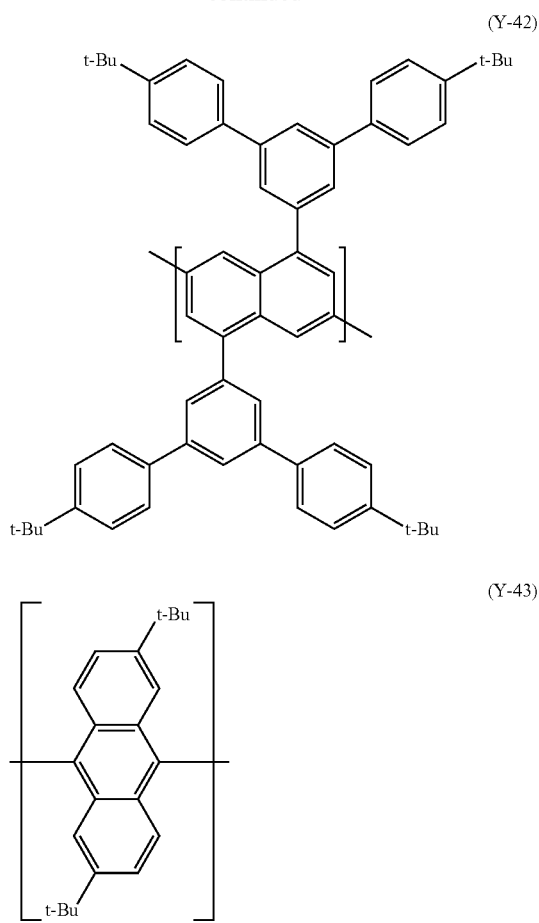
(Y-43) 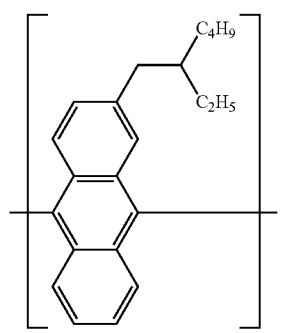
(Y-44) 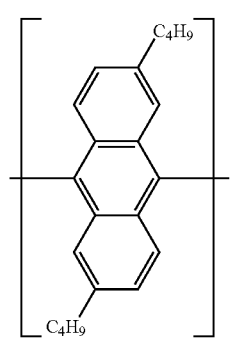
(Y-45)
(Y-46) 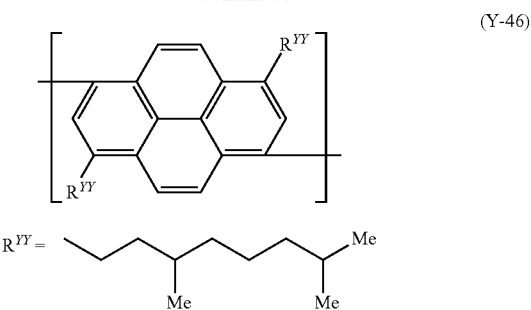
(Y-47) 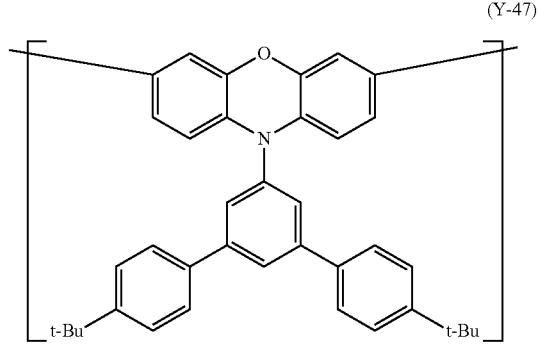
(Y-48) 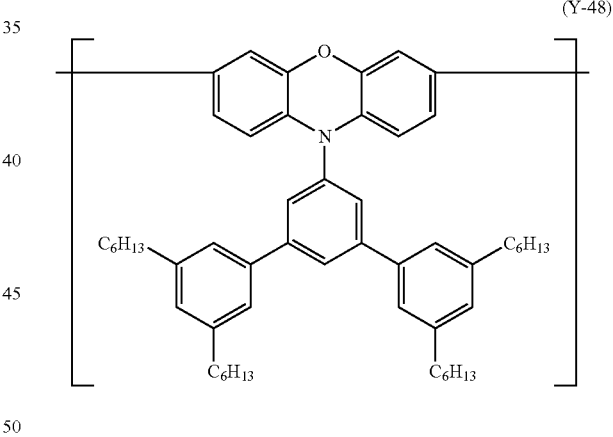
(Y-49) 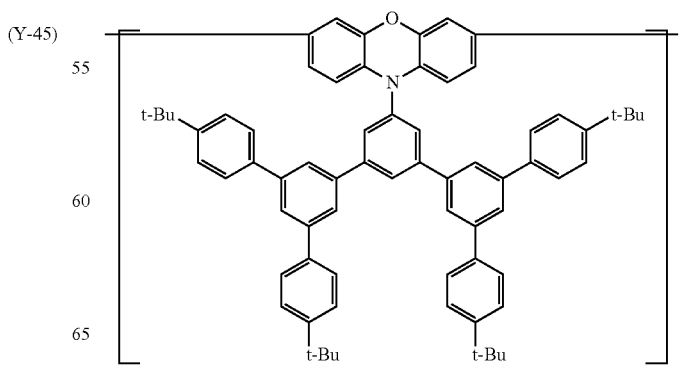

(Y-50)

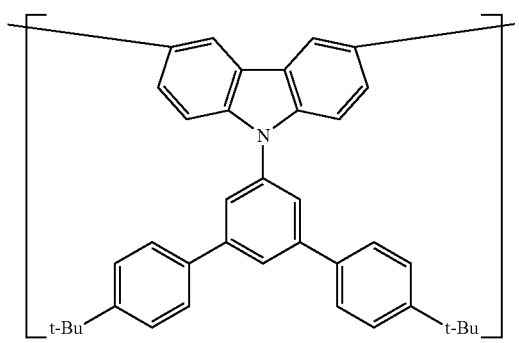

(Y-51)

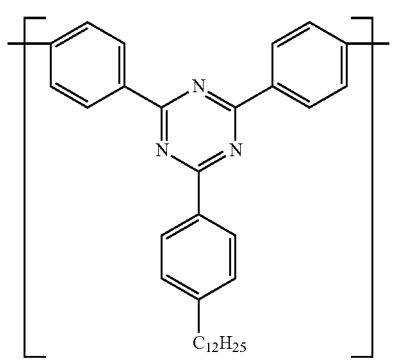

(Y-52)

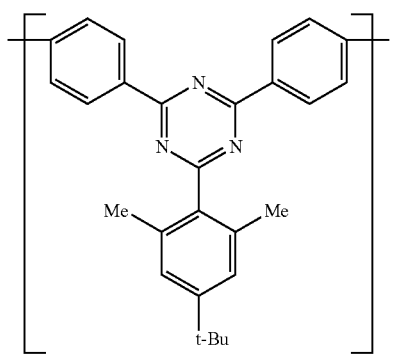

(Y-53)

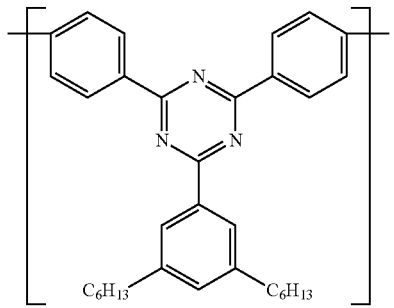

(Y-54)

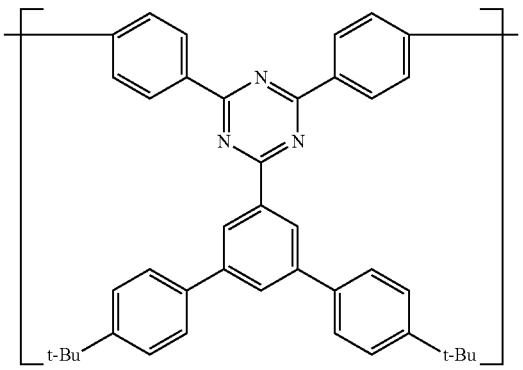

(Y-55)

The content of the constitutional unit represented by the formula (Y) in which $Ar^{Y1}$ is an arylene group is preferably 0.5 to 80 mol %, more preferably 30 to 60 mol % with respect to the total content of constitutional units contained in the polymer compound, because the luminance life of a light emitting device produced by using the polymer compound of the present invention is excellent.

The content of the constitutional unit represented by the formula (Y) in which $Ar^{Y1}$ is a divalent heterocyclic group or a divalent group in which at least one arylene group and at least one divalent heterocyclic group are bonded directly to each other is preferably 0.5 to 30 mol %, more preferably 3 to 40 mol % with respect to the total content of constitutional units contained in the polymer compound, because the charge transportability of a light emitting device produced by using the polymer compound of the present invention is excellent.

The constitutional unit represented by the formula (Y) may be contained only singly or two or more units thereof may be contained in the polymer compound.

It is preferable that the polymer compound of the present invention further comprises at least one constitutional unit selected from the group consisting of a constitutional unit represented by the formula (3) and a constitutional unit represented by the formula (3'), because crosslinkability is excellent.

[Constitutional Unit Represented by the Formula (3)]

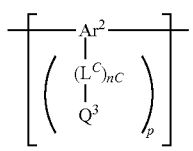

[wherein, nC represents an integer of 0 to 5, and p represents an integer of 1 or 2.

$Ar^2$ represents an aromatic hydrocarbon group or a heterocyclic ring group, and these groups each optionally have a substituent.

$L^C$ represents an ethylene group, a cycloalkylene group, an arylene group, a divalent heterocyclic ring group, a group represented by —NR'—, an oxygen atom or a sulfur atom, and these groups each optionally have a substituent, R' represents a hydrogen atom, an alkyl group, a cycloalkyl group, an aryl group or a monovalent heterocyclic group, and these groups each optionally have a substituent. When a plurality of $L^C$ are present, they may be the same or different.

$Q^3$ represents a crosslinkable group selected from Group A of crosslinkable group. When a plurality of $Q^3$ are present, they may be the same or different.].

nC is preferably 0 or 1, more preferably 0, because the light emitting device of the present invention is more excellent in light emission efficiency.

p is preferably 1 or 2, more preferably 2, because the light emitting device of the present invention is more excellent in light emission efficiency.

$Ar^2$ is preferably an aromatic hydrocarbon group optionally having a substituent, because the light emitting device of the present invention is more excellent in light emission efficiency.

The number of carbon atoms of the aromatic hydrocarbon group represented by $Ar^2$ is usually 6 to 60, preferably 6 to 30, more preferably 6 to 18, not including the number of carbon atoms of a substituent.

The arylene group portion obtained by removing p substituents of the aromatic hydrocarbon group represented by $Ar^2$ is preferably a group represented by the formula (A-1) to the formula (A-20), more preferably a group represented by the formula (A-1), the formula (A-2), the formula (A-6) to the formula (A-10), the formula (A-19) or the formula (A-20), further preferably a group represented by the formula (A-1), the formula (A-2), the formula (A-7), the formula (A-9) or the formula (A-19), and these groups each optionally have a substituent.

The number of carbon atoms of the heterocyclic ring group represented by $Ar^2$ is usually 6 to 60, preferably 6 to 30, more preferably 6 to 18, not including the number of carbon atoms of a substituent.

The divalent heterocyclic ring group portion obtained by removing p substituents of the heterocyclic ring group represented by $Ar^2$ is preferably a group represented by the formula (AA-1) to the formula (AA-34).

The aromatic hydrocarbon group and the heterocyclic ring group represented by $Ar^2$ each optionally have a substituent, and the substituent includes an alkyl group, a cycloalkyl group, an alkoxyl group, a cycloalkoxy group, an aryl group, an aryloxy group, a halogen atom, a monovalent heterocyclic group and a cyano group.

The number of carbon atoms of the alkylene group represented by $L^C$ is usually 1 to 10, preferably 1 to 5, more preferably 1 to 3, not including the number of carbon atoms of a substituent. The number of carbon atoms of the cycloalkylene group represented by $L^C$ is usually 3 to 10, not including the number of carbon atoms of a substituent.

The alkylene group and the cycloalkylene group each optionally have a substituent, and include, for example, a methylene group, an ethylene group, a propylene group, a butylene group, a hexylene group, a cyclohexylene group and an octylene group.

The alkylene group and the cycloalkylene group represented by $L^C$ each optionally have a substituent. The substituent which the alkylene group and the cycloalkylene group optionally have includes, for example, an alkyl group, a cycloalkyl group, an alkoxyl group, a cycloalkoxy group, a halogen atom and a cyano group.

The arylene group represented by $L^C$ optionally has a substituent. The arylene group includes o-phenylene, m-phenylene and p-phenylene. The substituent which the aryl group optionally has includes, for example, an alkyl group, a cycloalkyl group, an alkoxyl group, a cycloalkoxy group, an aryl group, an aryloxy group, a monovalent heterocyclic group, a halogen atom, a cyano group and a crosslinkable group selected from Group A of crosslinkable group.

$L^C$ is preferably a phenylene group or an alkylene group and these groups each optionally have a substituent, because production of the polymer compound of the present invention is easy.

The crosslinkable group represented by $Q^3$ is preferably a crosslinkable group represented by the formula (XL-1), (XL-3), (XL-5) or (XL-7), more preferably a crosslinkable group represented by the formula (XL-1), because the polymer compound of the present invention is excellent in crosslinkability.

The content of the constitutional unit represented by the formula (3) is preferably 0.5 to 50 mol %, more preferably 3 to 30 mol %, further preferably 3 to 20 mol % with respect to the total content of constitutional units contained in the polymer compound, because the polymer compound of the present invention is excellent in stability and crosslinkability.

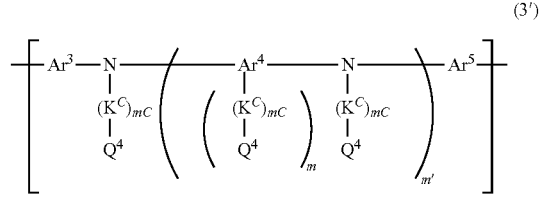

[wherein, mC represents an integer of 0 to 5, m represents an integer of 1 to 4, and m' represents 0 or 1. When a plurality of mC are present, they may be the same or different.

$Ar^4$ represents an aromatic hydrocarbon group, a heterocyclic ring group or a group in which at least one aromatic hydrocarbon ring and at least one heterocyclic ring are bonded directly to each other, and these groups each optionally have a substituent.

$Ar^3$ and $Ar^5$ each independently represent an arylene group or a divalent heterocyclic ring group, and these groups each optionally have a substituent.

Ar³, Ar⁴ and Ar⁵ each may be bonded to a group other than these groups linked to the nitrogen atom to which these groups are attached directly or via an oxygen atom or a sulfur atom, thereby forming a ring.

$K^C$ represents an alkylene group, a cycloalkylene group, an arylene group, a divalent heterocyclic ring group, a group represented by —NR'—, an oxygen atom or a sulfur atom, and these groups each optionally have a substituent. R' represents a hydrogen atom, an alkyl group, a cycloalkyl group, an aryl group or a monovalent heterocyclic group, and these groups each optionally have a substituent. When a plurality of $K^C$ are present, they may be the same or different.

$Q^4$ represents a crosslinkable group selected from Group A of crosslinkable group, a hydrogen atom, an alkyl group, a cycloalkyl group, an aryl group or a monovalent heterocyclic group, and these groups each optionally have a substituent. At least one $Q^4$ is a crosslinkable group selected from Group A of crosslinkable group.].

mC is preferably 0 or 1, more preferably 0, because the light emitting device of the present invention is more excellent in light emission efficiency.

m is preferably 2, because the light emitting device of the present invention is more excellent in light emission efficiency.

m' is preferably 0, because synthesis of the polymer compound of the present invention is easy and because the light emitting device of the present invention is more excellent in light emission efficiency.

Ar⁴ is preferably an aromatic hydrocarbon group, because the light emitting device of the present invention is more excellent in light emission efficiency.

The definition and examples of the arylene group portion obtained by removing m substituents of the aromatic hydrocarbon group represented by Ar⁴ are the same as the definition and examples of the arylene group represented by $Ar^{X2}$ in the formula (X) described above.

The definition and examples of the divalent heterocyclic ring group portion obtained by removing m substituents of the heterocyclic ring group represented by Ar⁴ are the same as the definition and examples of the divalent heterocyclic ring group portion represented by $Ar^{X2}$ in the formula (X) described above.

The definition and examples of the divalent group obtained by removing m substituents of the group in which at least one aromatic hydrocarbon ring and at least one heterocyclic ring are bonded directly to each other represented by Ar⁵ are the same as the definition and examples of the divalent group in which at least one arylene group and at least one divalent heterocyclic ring group are bonded directly to each other represented by $Ar^{X2}$ in the formula (X) described above.

Ar³ and Ar⁵ are preferably an arylene group, because the light emitting device of the present invention is more excellent in light emission efficiency.

The definition and examples of the arylene group represented by Ar³ and Ar⁵ are the same as the definition and examples of the arylene group represented by $Ar^{X1}$ and $Ar^{X3}$ in the formula (X) described above.

The definition and examples of the divalent heterocyclic ring group represented by Ar³ and Ar⁵ are the same as the definition and examples of the divalent heterocyclic ring group represented by $Ar^{X1}$ and $Ar^{X3}$ in the formula (X) described above.

The group represented by Ar³, Ar⁴ and Ar⁵ optionally has a substituent, and the substituent includes an alkyl group, a cycloalkyl group, an alkoxyl group, a cycloalkoxy group, an aryl group, an aryloxy group, a halogen atom, a monovalent heterocyclic group and a cyano group.

The definition and examples of the alkylene group, the cycloalkylene group, the arylene group and the divalent heterocyclic ring group represented by $K^C$ are the same as the definition and examples of the alkylene group, the cycloalkylene group, the arylene group and the divalent heterocyclic ring group represented by $L^C$, respectively, $K^C$ is preferably a phenylene group or a methylene group, because synthesis of the polymer compound of the present invention is easy.

The crosslinkable group represented by $Q^4$ is preferably a crosslinkable group represented by the formula (XL-1), the formula (XL-3), the formula (XL-5), the formula (XL-7), the formula (XL-16) or the formula (XL-17), more preferably a crosslinkable group represented by the formula (XL-17), because the polymer compound of the present invention is excellent in crosslinkability.

The content of the constitutional unit represented by the formula (3') is preferably 0.5 to 50 mol %, more preferably 3 to 30 mol %, further preferably 3 to 20 mol % with respect to the total content of constitutional units contained in the polymer compound, because the polymer compound of the present invention is excellent in stability and crosslinkability.

The constitutional unit represented by the formula (3) and the constitutional unit represented by the formula (3') each may be contained only singly or two or more of the constitutional units may be contained in the polymer compound.

The constitutional unit represented by the formula (3) includes, for example, constitutional units represented by the formula (3-1) to the formula (3-20), and the constitutional unit represented by the formula (3') includes, for example, constitutional units represented by the formula (3'-1) to the formula (3'-13). Of them, constitutional units represented by the formula (3-1) to the formula (3-7), the formula (3-11), the formula (3-12) or the formula (3-15) to the formula (3-20) are preferable, and constitutional units represented by the formula (3-1) to the formula (3-4), the formula (3-7), the formula (3-11), the formula (3-12), the formula (3-15) or the formula (3-17) are more preferable, and constitutional units represented by the formula (3-1) to the formula (3-4), the formula (3-11) or the formula (3-15) are further preferable, because the polymer compound of the present invention is excellent in crosslinkability.

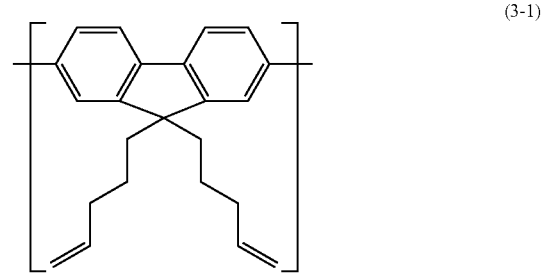

(3-1)

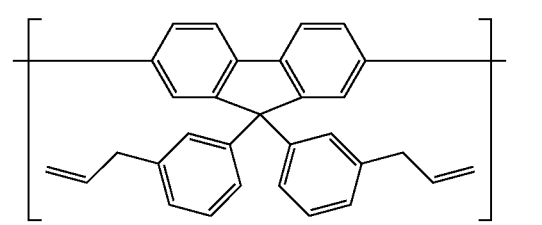

(3-2)

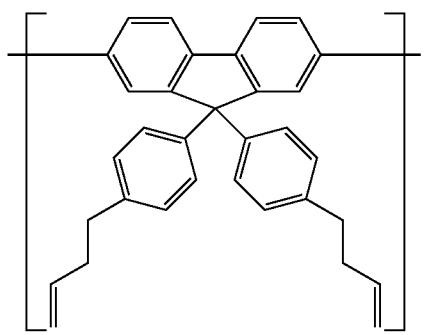
(3-3)
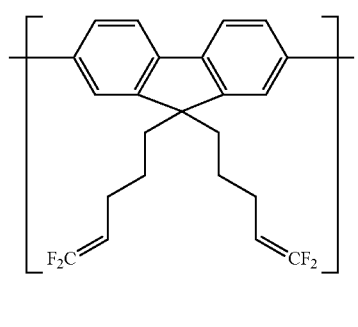
(3-7)
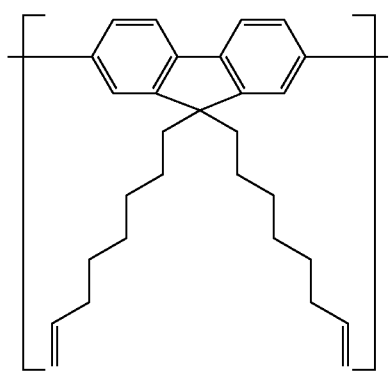
(3-4)
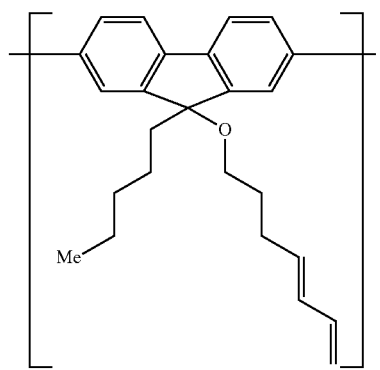
(3-8)
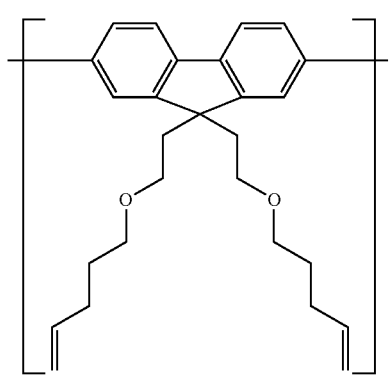
(3-5)
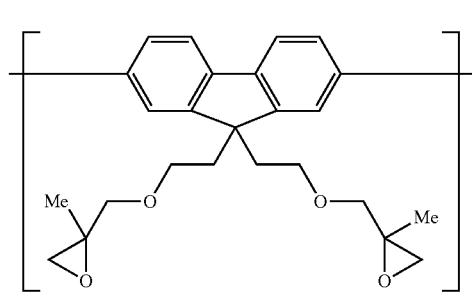
(3-9)
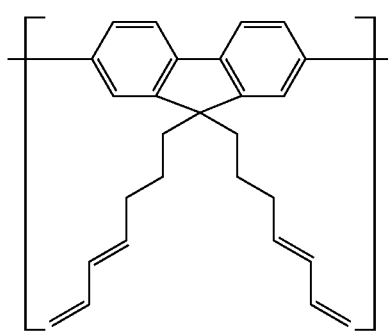
(3-6)
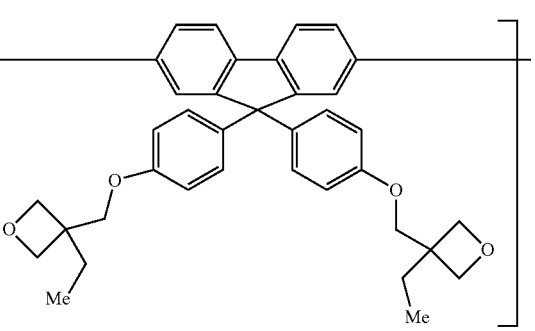
(3-10)

(3-11) 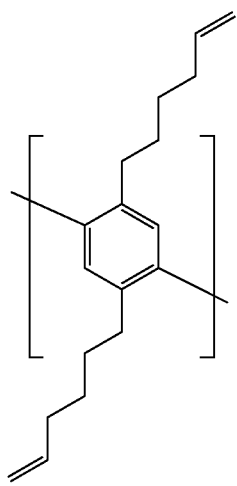
(3-12) 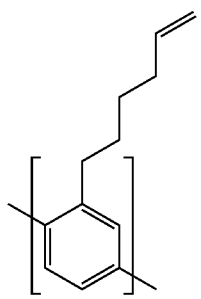
(3-13) 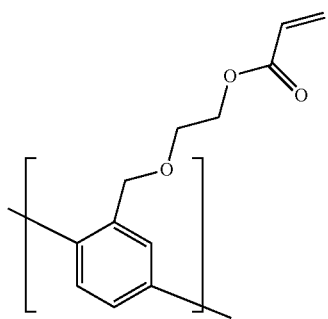
(3-14) 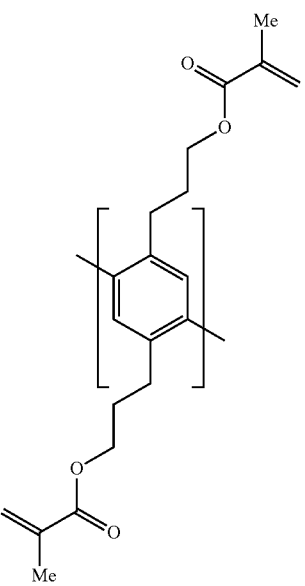
(3-15) 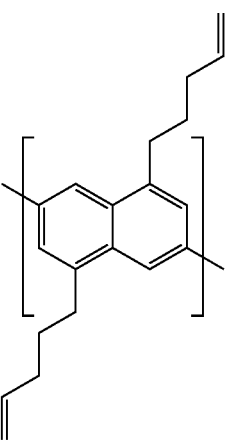
(3-16) 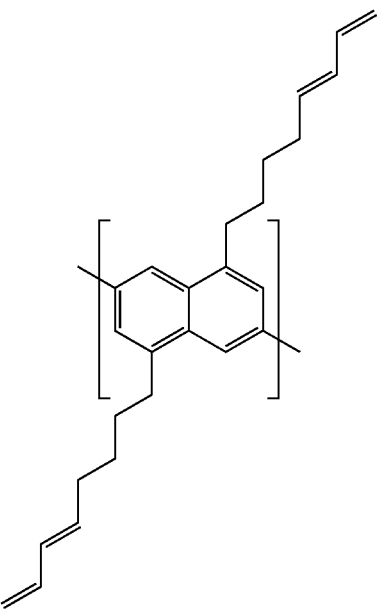

-continued
(3-17)
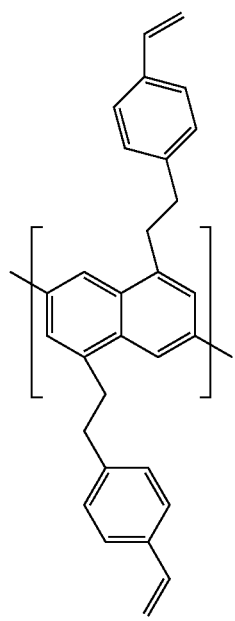
(3-18)
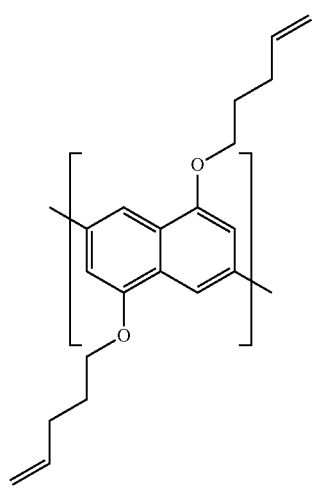
(3-19)
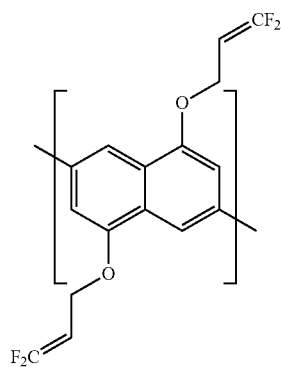
-continued
(3-20)
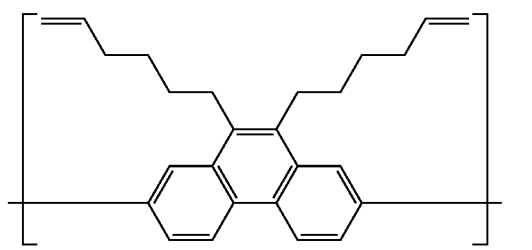
(3'-1)
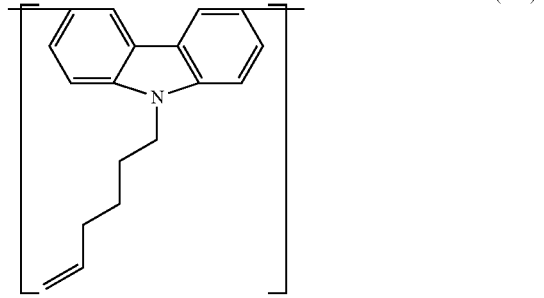
(3'-2)
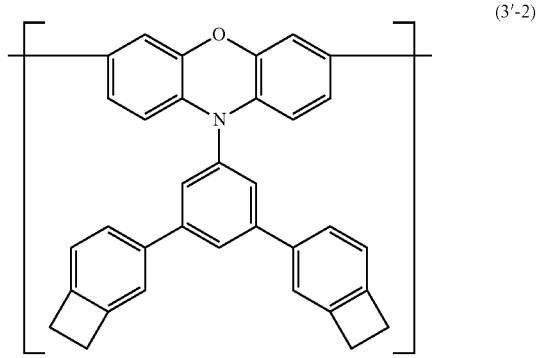
(3'-3)
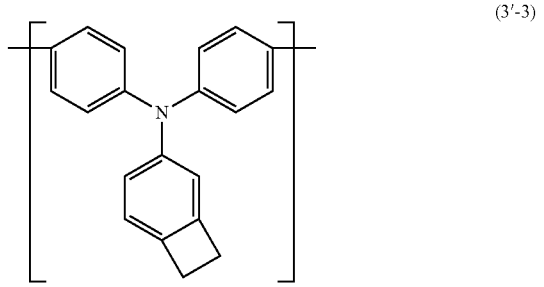
(3'-4)
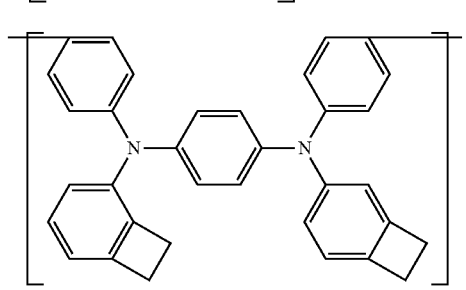

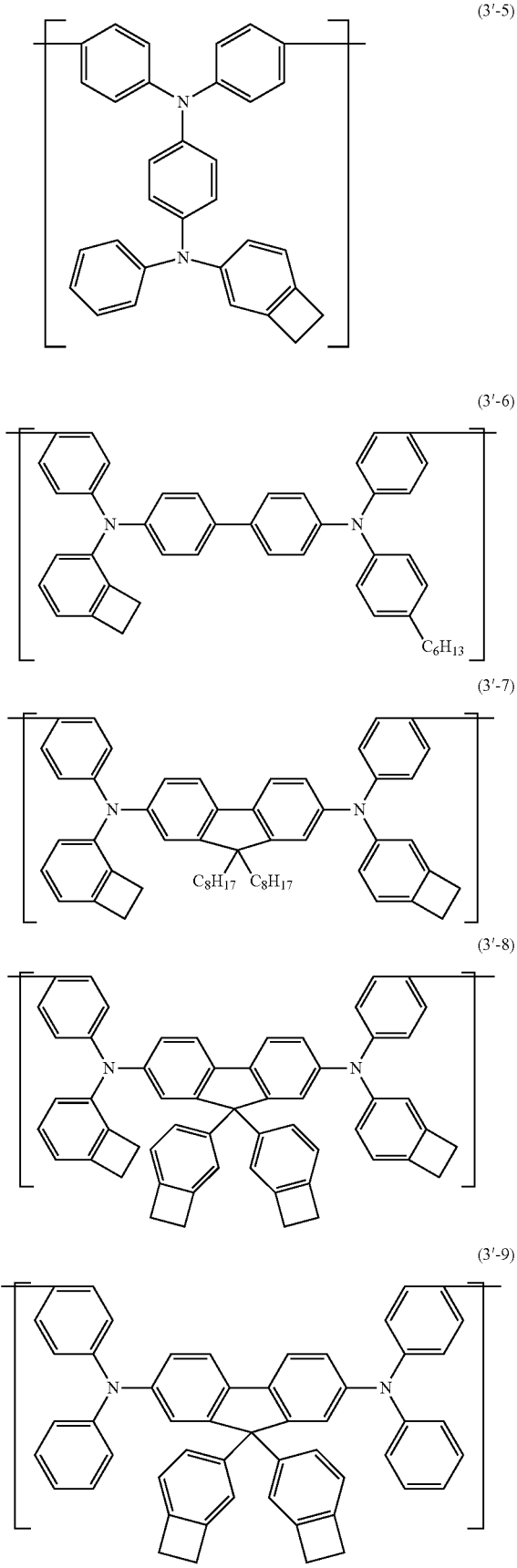

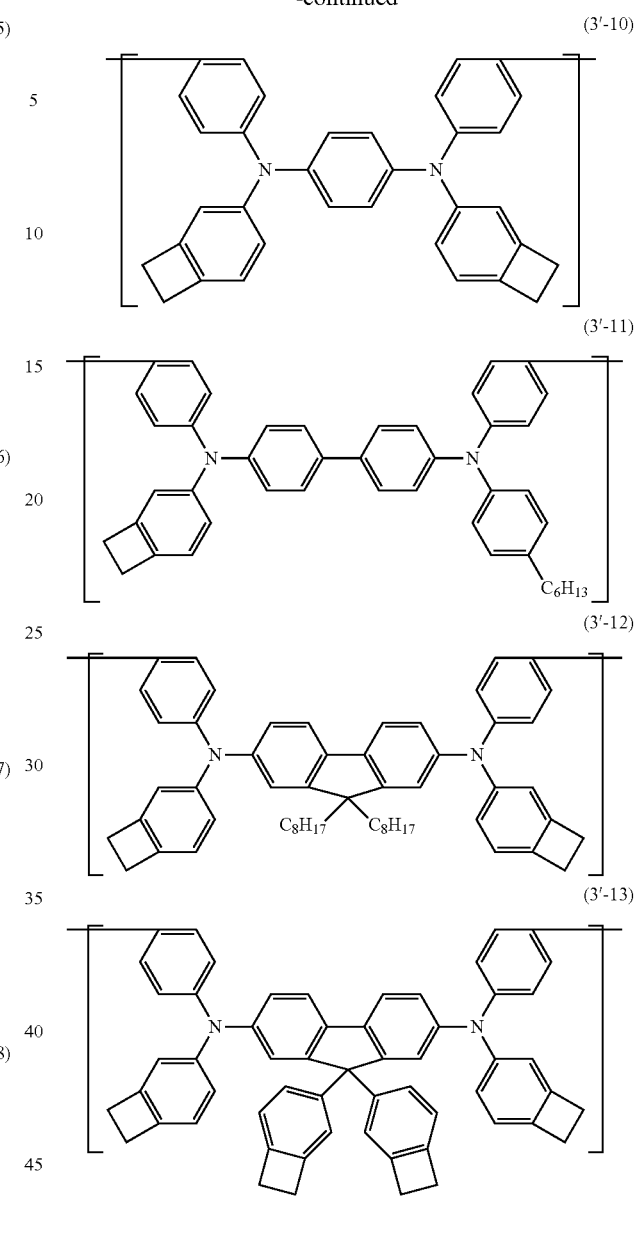

The polymer compound of the present invention includes, for example, polymer compounds P-1 to P-10 shown in Table 4. "other constitutional unit" denotes a constitutional unit other than constitutional units represented by the formula (2), the formula (X), the formula (Y), the formula (3) and the formula (3').

TABLE 4

| | molar ratio of constitutional unit | | | | | |
|---|---|---|---|---|---|---|
| Polymer compound | formula (2) q | formula (X) r | formula (Y) s | formula (3) t | formula (3') u | others v |
| P-1 | 0.1 to 99.9 | 0.1 to 99.9 | 0 | 0 | 0 | 0 to 30 |
| P-2 | 0.1 to 99.9 | 0 | 0 | 0 | 0.1 to 99.9 | 0 to 30 |
| P-3 | 0.1 to 99.8 | 0.1 to 99.8 | 0.1 to 99.8 | 0 | 0 | 0 to 30 |

TABLE 4-continued

| Polymer compound | molar ratio of constitutional unit | | | | | |
|---|---|---|---|---|---|---|
| | formula (2) q | formula (X) r | formula (Y) s | formula (3) t | formula (3') u | others v |
| P-4 | 0.1 to 99.8 | 0.1 to 99.8 | 0 | 0.1 to 99.8 | 0 | 0 to 30 |
| P-5 | 0.1 to 99.8 | 0 | 0.1 to 99.8 | 0 | 0.1 to 99.8 | 0 to 30 |
| P-6 | 0.1 to 99.8 | 0 | 0 | 0.1 to 99.8 | 0.1 to 99.8 | 0 to 30 |
| P-7 | 0.1 to 99.8 | 0.10 to 99.8 | 0 | 0 | 0.1 to 99.8 | 0 to 30 |
| P-8 | 0.1 to 99.7 | 0.1 to 99.7 | 0.1 to 99.7 | 0.1 to 99.7 | 0 | 0 to 30 |
| P-9 | 0.1 to 99.7 | 0 | 0.1 to 99.7 | 0.1 to 99.7 | 0.1 to 99.7 | 0 to 30 |
| P-10 | 0.1 to 99.6 | 0.1 to 99.6 | 0.1 to 99.6 | 0.1 to 99.6 | 0.1 to 99.6 | 0 to 30 |

[in the table, q, r, s, t, u and v represent the mole fraction of each constitutional unit, q+r+s+t+u+v=100 and, 70≤q+r+s+t+v≤100.].

The examples and preferable ranges of constitutional units represented by the formula (2), the formula (X), the formula (Y), the formula (3) and the formula (3') in polymer compounds P-1 to P-10 are as described above.

An end group of the polymer compound of the present invention is preferably a stable group, because if a polymerization active group remains intact at the end, when the polymer compound is used for fabrication of a light emitting device, the light emitting property or luminance life possibly becomes lower. This end group is preferably a group having a conjugated bond to the main chain, and includes groups bonding to an aryl group or a monovalent heterocyclic group via a carbon-carbon bond.

The polymer compound of the present invention may be any of a block copolymer, a random copolymer, an alternative copolymer and a graft copolymer, and may also be other embodiment, and a copolymer produced by copolymerizing a several raw material monomers is preferable.

<Production Method of Polymer Compound>

Next, the production method of the polymer compound of the present invention will be illustrated.

The polymer compound of the present invention can be produced, for example, by condensation-polymerizing a compound represented by the formula (2M), or condensation-polymerizing a compound represented by the formula (2M), a compound represented by the formula (M-1) and/or a compound represented by the formula (M-2) and other compounds (for example, a compound represented by the formula (M-3) and/or the formula (3')). In the present specification, compounds used for production of the polymer compound of the present invention are collectively called "raw material monomer" in some cases.

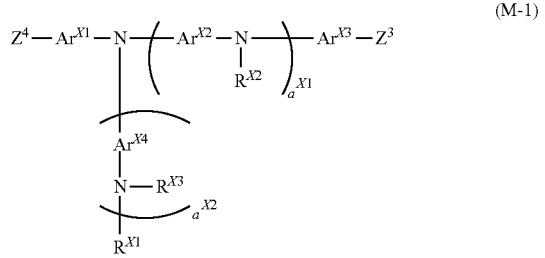

(M-1)

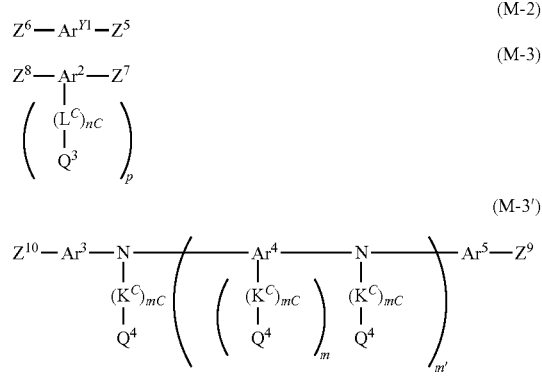

[wherein, $a^{X1}$, $a^{X2}$, $Ar^{X1}$ to $Ar^{X4}$, $R^{X1}$ to $R^{X3}$, $Ar^{Y1}$, nC, p, $L^C$, $Q^3$, $Ar^2$, $Ar^3$, $Ar^4$, $Ar^5$, $K^C$, $Q^4$, m, m' and mC represent the same meaning as described above.

$Z^3$ to $Z^{10}$ each independently represent a group selected from the group consisting of Group A of substituent and Group B of substituent.].

For example, when $Z^1$, $Z^2$, $Z^5$ and $Z^6$ and are a group selected from Group A of substituent, $Z^3$, $Z^4$, $Z^7$, $Z^8$, $Z^9$ and $Z^{10}$ and are selected from Group B of substituent.

For example, when $Z^1$, $Z^2$, $Z^5$ and $Z^6$ are a group selected from Group B of substituent, $Z^3$, $Z^4$, $Z^7$, $Z^8$, $Z^9$ and $Z^{10}$ are selected from Group A of substituent.

<Group A of Substituent>

A chlorine atom, a bromine atom, an iodine atom and a group represented by —O—S(=O)$_2$R$^{C1}$ (wherein, R$^{C1}$ represents an alkyl group, a cycloalkyl group or an aryl group, and these groups each optionally have a substituent.).

<Group B of Substituent>

A group represented by —B(OR$^{C2}$)$_2$ (wherein, R$^{C2}$ represents a hydrogen atom, an alkyl group, a cycloalkyl group or an aryl group, and these groups each optionally have a substituent. The plurality of R$^{C2}$ may be the same or different and may be combined together to form a cyclic structure together with the oxygen atoms to which they are attached.);

a group represented by —BF$_3$Q' (wherein, Q' represents a lithium atom, a sodium atom, a potassium atom, a rubidium atom or a cesium atom.);

a group represented by —MgY' (wherein, Y' represents a chlorine atom, a bromine atom or an iodine atom.);

a group represented by —ZnY" (wherein, Y" represents a chlorine atom, a bromine atom or an iodine atom.); and a group represented by —Sn(R$^{C3}$)$_3$ (wherein, R$^{C3}$ represents a hydrogen atom, an alkyl group, a cycloalkyl group or an aryl group, and these groups each optionally have a substituent. The plurality of R$^{C3}$ may be the same or different and may be combined together to form a cyclic structure together with the tin atom to which they are attached.).

As the group represented by —B(OR$^{C2}$)$_2$, groups represented by the following formulae are exemplified.

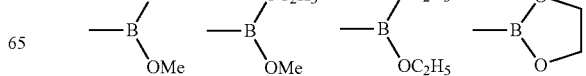

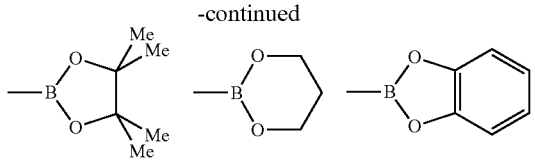

The compound having a group selected from Group A of substituent and the compound having a group selected from Group B of substituent undergo condensation polymerization by a known coupling reaction, thereby giving mutual bonding of carbon atoms linking the group selected from Group A of substituent and the group selected from Group B of substituent. Therefore, when a compound having two groups selected from Group A of substituent and a compound having two groups selected from Group B of substituent are subjected to a known coupling reaction, a condensed polymer of these compounds can be produced by condensation polymerization.

The condensation polymerization is carried out usually in the presence of a catalyst, a base and a solvent, and if necessary, a phase transfer catalyst may coexist.

The catalyst includes, for example, transition metal complexes such as palladium complexes such as dichlorobis(triphenylphosphine)palladium, dichlorobis(tris-o-methoxyphenylphosphine)palladium, palladium[tetrakis(triphenylphosphine)], [tris(dibenzylideneacetone)]dipalladium and palladium acetate, nickel complexes such as nickel[tetrakis(triphenylphosphine)], [1,3-bis(diphenylphosphino)propane]dichloronickel and [bis(1,4-cyclooctadiene)]nickel; these transition metal complexes further having a ligand such as triphenylphosphine, tri-o-tolylphosphine, tri-tert-butylphosphine, tricyclohexylphosphine, diphenylphosphinopropane and bipyridyl. The catalysts may be used singly or in combination.

The use amount of the catalyst is usually 0.00001 to 3 molar equivalents in terms of the amount of a transition metal with respect to the sum of the molar numbers of raw material monomers.

The base and the phase transfer catalyst include, for example, inorganic bases such as sodium carbonate, potassium carbonate, cesium carbonate, potassium fluoride, cesium fluoride and tripotassium phosphate; organic bases such as tetrabutylammonium fluoride and tetrabutylammonium hydroxide; and phase transfer catalysts such as tetrabutylammonium chloride and tetrabutylammonium bromide. The bases and the phase transfer catalysts each may be used singly or in combination.

The use amounts of the base and the phase transfer catalyst are each usually 0.001 to 100 molar equivalents with respect to the total molar number of raw material monomers.

The solvent includes, for example, organic solvents such as toluene, xylene, mesitylene, tetrahydrofuran, 1,4-dioxane, dimethoxyethane, N,N-dimethylacetamide and N,N-dimethylformamide; and water. The solvent may be used singly or two or more solvents may be used in combination.

The use amount of the solvent is usually 10 to 100000 parts by weight with respect to 100 parts by weight of the total amount of raw material monomers.

The reaction temperature of condensation polymerization is usually −100 to 200° C. The reaction time is usually 1 hour or longer.

The post treatment of the polymerization reaction is conducted by known methods, such as a method of removing water-soluble impurities by liquid separation and a method in which the reaction solution resulting from the polymerization reaction is added to a lower alcohol such as methanol and a precipitate deposited is collected by filtration and dried, that are applied individually or in combination. When the polymer compound has a low purity, the polymer host can be purified by a usual method, such as recrystallization, reprecipitation, continuous extraction by a Soxhlet extractor and column chromatography.

[Compound Represented by the Formula (2M)]

The compound of the present invention is a compound represented by the formula (2M) and it can be suitably used in the production method of the polymer compound of the present invention described above.

It is preferable that $Z^1$ and $Z^2$ are the same group because production of the compound of the present invention is easy.

[Production Method of Compound Represented by the Formula (2M)]

The compound represented by the formula (2M) can be produced, for example, by a method described in Schemes 1 to 5 described below.

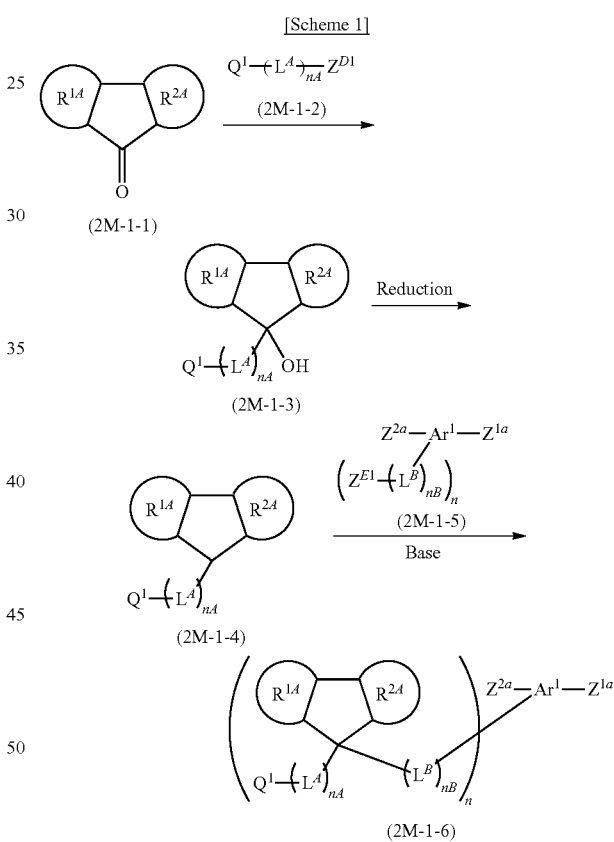

In Scheme 1

$R^{1A}$, $R^{2A}$, $Q^1$, $L^A$, nA, $Ar^1$, $L^B$, nB and n represent the same meaning as described above.

$Z^{D1}$ represents an alkali metal atom or a group represented by $-M^{10}Z^{1H}$. $M^{10}$ represents a magnesium atom or a zinc atom, and $Z^{1H}$ represents a halogen atom.

$Z^{E1}$ represents a group selected from Group A of substituent.

$Z^{1a}$ and $Z^{2a}$ each independently represent a hydrogen atom or a group selected from Group A of substituent.

The alkali metal atom represented by $Z^{D1}$ includes a lithium atom and a potassium atom.

The halogen atom represented by $Z^{1H}$ includes a chlorine atom, a bromine atom or an iodine atom.

In Scheme 1, first, a compound represented by the formula (2M-1-1) and a compound represented by the formula (2M-1-2) are subjected to a nucleophilic addition reaction, thereby synthesizing a compound represented by the formula (2M-1-3). Next, the compound represented by the formula (2M-1-3) is subjected to a known reaction such as a hydrogenation reaction and a reduction reaction using triethylsilane to convert a hydroxyl group into a hydrogen atom, thereby synthesizing a compound represented by the formula (2M-1-4). Next, in the presence of a base, a compound represented by the formula (2M-1-5) and the compound represented by the formula (2M-1-4) can be subjected to a nucleophilic substitution reaction, thereby synthesizing a compound represented by the formula (2M-1-6).

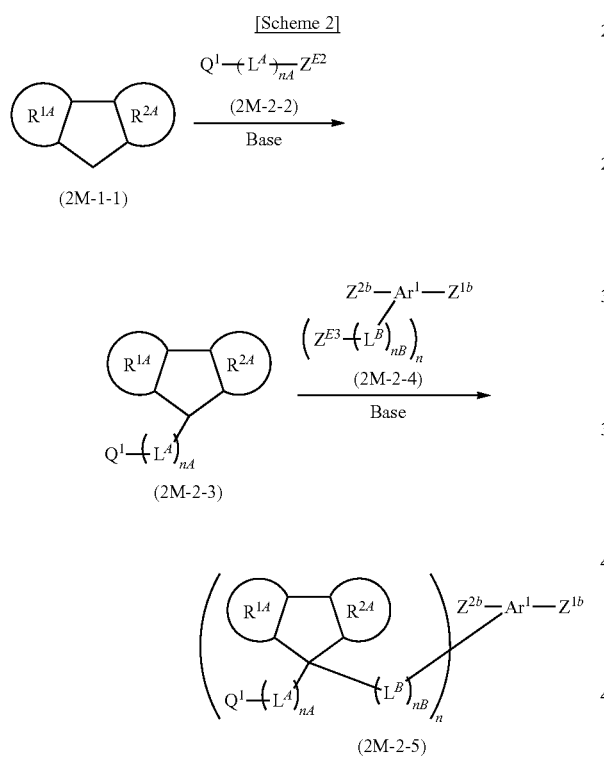

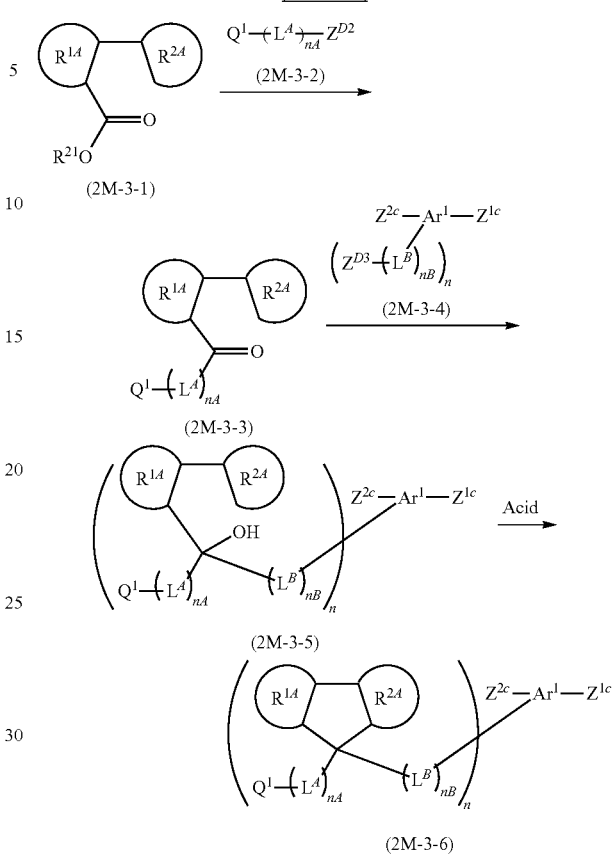

In Scheme 2, $R^{1A}$, $R^{2A}$, $Q^1$, $L^A$, nA, $Ar^1$, $L^B$, nB and n represent the same meaning as described above.

$Z^{E2}$ and $Z^{E3}$ each independently represent a group selected from Group A of substituent.

$Z^{1b}$ and $Z^{2b}$ each independently represent a hydrogen atom or a group selected from Group A of substituent.

In Scheme 2, first, in the presence of a base, a compound represented by the formula (2M-2-1) and a compound represented by the formula (2M-2-2) are subjected to a nucleophilic substitution reaction, thereby synthesizing a compound represented by the formula (2M-2-3). Next, in the presence of a base, a compound represented by the formula (2M-2-4) and the compound represented by the formula (2M-2-3) can be subjected to a nucleophilic substitution reaction, thereby synthesizing a compound represented by the formula (2M-2-5).

In Scheme 3, $R^{1A}$, $R^{2A}$, $Q^1$, $L^A$, nA, $Ar^1$, $L^B$, nB and n represent the same meaning as described above.

$R^{Z1}$ represents an alkyl group or a cycloalkyl group, and this group optionally has a substituent.

$Z^{D2}$ and $Z^{D3}$ each independently represent an alkali metal atom or a group represented by $-M^{11}Z^{2H}$. $M^{11}$ represents a magnesium atom or a zinc atom, and $Z^{2H}$ represents a halogen atom.

$Z^{1c}$ and $Z^{2c}$ each independently represent a hydrogen atom or a group selected from Group A of substituent.

The alkali metal atom represented by $Z^{D2}$ and $Z^{D3}$ includes a lithium atom and a potassium atom.

The halogen atom represented by $Z^{2H}$ includes a chlorine atom, a bromine atom or an iodine atom.

In Scheme 3, first, a compound represented by the formula (2M-3-1) and a compound represented by the formula (2M-3-2) are subjected to a nucleophilic substitution reaction, thereby synthesizing a compound represented by the formula (2M-3-3). Next, the compound represented by the formula (2M-3-3) and a compound represented by the formula (2M-3-4) are subjected to a nucleophilic addition reaction, thereby synthesizing a compound represented by the formula (2M-3-5). Next, the compound represented by the formula (2M-3-5) can be subjected to a ring-closing reaction according to a known reaction such as generation of cations in the presence of an acid to cause intramolecular ring-closing and the like, thereby synthesizing a compound represented by the formula (2H-3-6).

[Scheme 4]

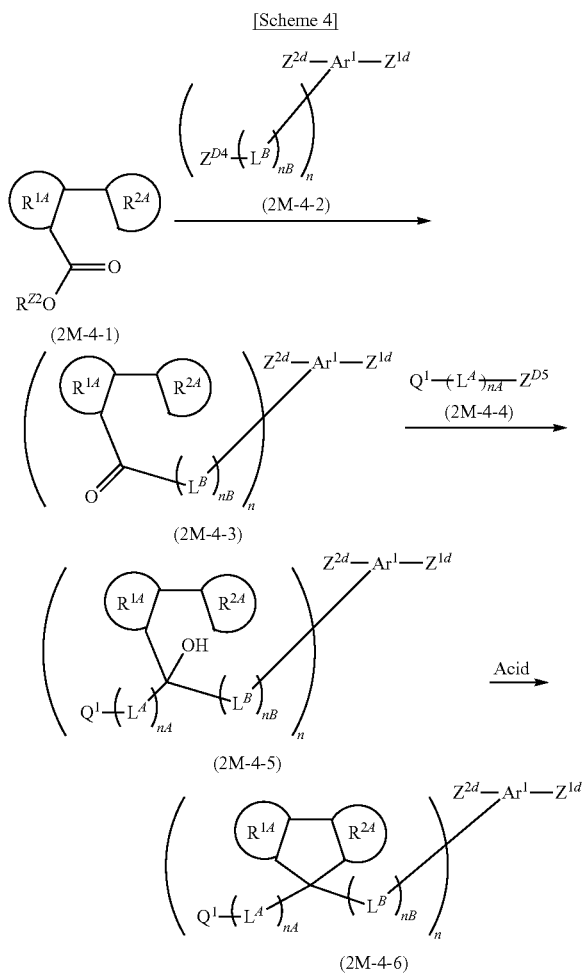

[Scheme 5]

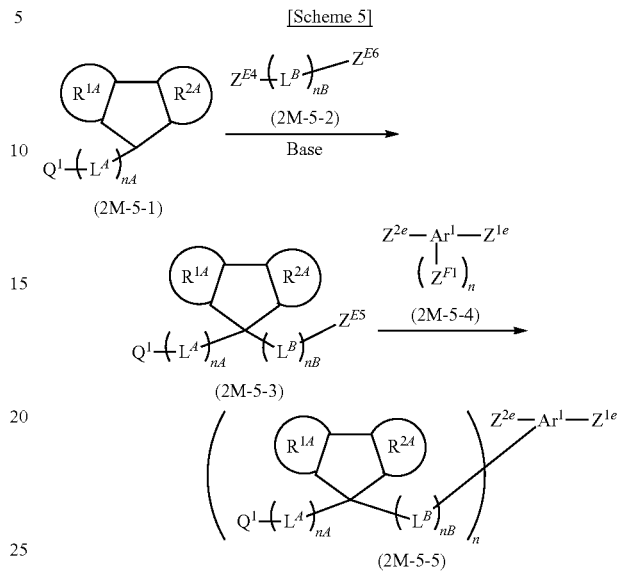

In Scheme 4,
$R^{1A}$, $R^{2A}$, $Q^1$, $L^A$, nA, $Ar^1$, $L^B$, nB and n represent the same meaning as described above.

$R^{Z2}$ represents an alkyl group or a cycloalkyl group, and this group optionally has a substituent.

$Z^{D4}$ and $Z^{D5}$ each independently represent an alkali metal atom or a group represented by $-M^{12}Z^{3H}$. $M^{12}$ represents a magnesium atom or a sine atom, and $Z^{3H}$ represents a halogen atom.

$Z^{1d}$ and $Z^{2d}$ each independently represent a hydrogen atom or a group selected from Group A of substituent.

The alkali metal atom represented by $Z^{D4}$ and $Z^{D5}$ includes a lithium atom and a potassium atom.

The halogen atom represented by $Z^{3H}$ includes a chlorine atom, a bromine atom or an iodine atom.

In Scheme 4, first, a compound represented by the formula (2M-4-1) and a compound represented by the formula (2M-4-2) are subjected to a nucleophilic substitution reaction, thereby synthesizing a compound represented by the formula (2M-4-3). Next, the compound represented by the formula (2M-4-3) and a compound represented by the formula (2M-4-4) are subjected to a nucleophilic addition reaction, thereby synthesizing a compound represented by the formula (2M-4-5). Next, the compound represented by the formula (2M-4-5) can be subjected to a ring-closing reaction according to a known reaction such as generation of cations in the presence of an acid to cause intramolecular ring-closing and the like, thereby synthesizing a compound represented by the formula (2M-4-6).

In Scheme 5,
$R^{1A}$, $R^{2A}$, $Q^1$, $L^A$, nA, $Ar^1$, $L^B$, nB and n represent the same meaning as described above.

$Z^{E4}$ and $Z^{E5}$ each independently represent a group selected from Group A of substituent.

$Z^{F1}$ represents a group selected from Group A of substituent or a group selected from Group B of substituent.

$Z^{1c}$ and $Z^{2c}$ each independently represent a hydrogen atom or a group selected from Group A of substituent.

In Scheme 5, first, a compound represented by the formula (2M-5-1) and a compound represented by the formula (2M-5-2) are subjected to a nucleophilic substitution reaction in the presence of a base, thereby synthesizing a compound represented by the formula (2M-5-3). Next, the compound represented by the formula (2M-5-3) and a compound represented by the formula (2M-5-4) can be reacted according to a known reaction such as an alkylation reaction, a cross-coupling reaction typified by the Suzuki reaction and the like, thereby synthesizing a compound represented by the formula (2M-5-5)

The compound represented by the formula (2M-5-1) can be synthesized by the same method as for the compound represented by the formula (2M-1-4) and the compound represented by the formula (2M-2-3).

In the compound represented by the formula (2M-1-6) in which $Z^{1n}$ and $Z^{2n}$ are a hydrogen atom, the compound represented by the formula (2M-2-5) in which $Z^{1b}$ and $Z^{2b}$ are a hydrogen atom, the compound represented by the formula (2M-3-6) in which $Z^{1c}$ and $Z^{2c}$ are a hydrogen atom, the compound represented by the formula 2M-4-6) in which $Z^{1d}$ and $Z^{2d}$ are a hydrogen atom and the compound represented by the formula (2M-5-5) in which $Z^{1e}$ and $Z^{2e}$ are a hydrogen atom, the hydrogen atom can be converted into a group selected from Group A of substituent by a reaction such as a bromination reaction and the like.

In the compound represented by the formula (2M-1-6) in which it $Z^{1a}$ and $Z^{2a}$ are a group selected from Group A of substituent, the compound represented by the formula (2M-2-5) in which $Z^{1b}$ and $Z^{2b}$ are a group selected from Group A of substituent, the compound represented by the formula (2M-3-6) in which $Z^{1c}$ and $Z^{2c}$ are a group selected from Group A of substituent, the compound represented by the formula (2M-4-6) in which $Z^{1d}$ and $Z^{2d}$ are a group selected from Group A of substituent and the compound represented by the formula (2M-5-5) in which $Z^{1e}$ and $Z^{2e}$ are a group selected from Group A of substituent, the group selected from Group A of substituent can be converted into a group selected from Group B of substituent by a known reaction such as boronate esterification using bispinacolatodiboron or 2-alkoxy-4,4,5,5-tetramethyl-1,3,2-dioxaborolane, and the like.

<Composition>

The composition of the present invention comprises at least one material selected from the group consisting of a hole transporting material, a hole injection material, an electron transporting material, an electron injection material, a light emitting material, an antioxidant and a solvent and the polymer compound of the present invention.

The composition comprising the polymer compound of the present invention and a solvent (hereinafter, referred to as "ink" in some cases) is suitable for fabrication of a light emitting device using a printing method such as an inkjet printing method and a nozzle printing method.

The viscosity of the ink may be adjusted depending on the kind of the printing method, and when a solution goes through a discharge apparatus such as in an inkjet printing method, the viscosity is preferably in the range of 1 to 20 mPa·s at 25° C. for preventing curved aviation and clogging in discharging.

As the solvent contained in the ink, those capable of dissolving or uniformly dispersing solid components in the ink are preferable. The solvent includes, for example, chlorine-based solvents such as 1,2-dichloroethane, 1,1,2-trichloroethane, chloroboenzene and o-dichlorobenzene; ether solvents such as tetrahydrofuran, dioxane, anisole and 4-methylanisole; aromatic hydrocarbon solvents such as toluene, xylene, mesitylene, ethylbenzene, n-hexylbenzene and cyclohexylbenzene; aliphatic hydrocarbon solvents such as cyclohexane, methylcyclohexane, n-pentane, n-hexane, n-heptane, n-octane, n-nonane, n-decane, n-dodecane and bicyclohexyl; ketone solvents such as acetone, methylethylketone, cyclohexanone and acetophenone; ester solvents such as ethyl acetate, butyl acetate, ethylcellosolve acetate, methyl benzoate and phenyl acetate; poly-hydric alcohols such as ethylene glycol, glycerin and 1,2-hexanediol and derivatives thereof; alcohol solvents such as isopropanol and cyclohexanol; sulfoxide solvents such as dimethyl sulfoxide; and amide solvents such as N-methyl-2-pyrrolidone and N,N-dimethylformamide. These solvents may be used singly or two or more of them may be used in combination.

In the ink, the compounding amount of the solvent is usually 1000 to 100000 parts by weight, preferably 2000 to 20000 parts by weight with respect to 100 parts by weight of the polymer compound of the present invention.

[Hole Transporting Material]

The hole transporting material is classified into low molecular weight compounds and polymer compounds, and polymer compounds are preferable, polymer compounds having a crosslinkable group are more preferable.

The polymer compound includes, for example, polyvinylcarbazole and derivatives thereof; polyarylene having an aromatic amine structure in the side chain or main chain and derivatives thereof. The polymer compound may also be a compound in which an electron accepting portion is linked. The electron accepting portion includes, for example, fullerene, tetrafluorotetracyanoquinodimethane, tetracyanoethylene and trinitrofluorenone, preferably fullerene.

In the composition of the present invention, the compounding amount of the hole transporting material is usually 1 to 400 parts by weight, preferably 5 to 150 parts by weight with respect to 100 parts by weight of the polymer compound of the present invention.

The hole transporting material may be used singly or two or more hole transporting materials may be used in combination.

[Electron Transporting Material]

The electron transporting material is classified into low molecular weight compounds and polymer compounds. The electron transporting material optionally has a crosslinkable group.

The low molecular weight compound includes, for example, a metal complex having 8-hydroxyquinoline as a ligand, oxadiazole, anthraquinodimethane, benzoquinone, naphthoquinone, anthraquinone, tetracyanoanthraguinodimethane, fluorenone, diphenyldicyanoethylene, diphenoquinone and derivatives thereof.

The polymer compound includes, for example, polyphenylene, polyfluorene and derivatives thereof. These polymer compounds may be doped with a metal.

In the composition of the present invention, the compounding amount of the electron transporting material is usually 1 to 400 parts by weight, preferably 5 to 150 parts by weight with respect to 100 parts by weight of the polymer compound of the present invention.

The electron transporting material may be used singly or two or more electron transporting materials may be used in combination.

[Hole Injection Material and Electron Injection Material]

The hole injection material and the electron injection material are each classified into low molecular weight compounds and polymer compounds. The hole injection material and the electron injection material each optionally has a crosslinkable group.

The low molecular weight compound includes, for example, metal phthalocyanines such as copper phthalocyanine; carbon; oxides of metals such as molybdenum and tungsten; metal fluorides such as lithium fluoride, sodium fluoride, cesium fluoride and potassium fluoride.

The polymer compound includes, for example, polyaniline, polythiophene, polypyrrole, polyphenylenevinylene, polythienylenevinylene, polyquinoline and polyquinoxaline, and derivatives thereof; electrically conductive polymers such as a polymer comprising an aromatic amine structure in the main chain or side chain.

In the composition of the present invention, the compounding amounts of the hole injection material and the electron injection material are each usually 1 to 400 parts by weight, preferably 5 to 150 parts by weight with respect to 100 parts by weight of the polymer compound of the present invention.

The hole injection material and the electron injection material may each be used singly or two or more of them may be used in combination.

[Ion Dope]

When the hole injection material or the electron injection material comprises an electrically conductive polymer, the electric conductivity of the electrically conductive polymer is preferably $1 \times 10^{-5}$ S/cm to $1 \times 10^3$ S/cm. For adjusting the electric conductivity of the electrically conductive polymer within such a range, the electrically conductive polymer can be doped with a suitable amount of ions.

The kind of the ion to be doped is an anion for a hole injection material and a cation for an electron injection material. The anion includes, for example, a polystyrenesulfonate ion, an alkylbenzenesulfonate ion and a camphorsulfonate ion. The cation includes, for example, a lithium ion, a sodium ion, a potassium ion and a tetrabutylammonium ion.

The ion to be doped may be used singly or two or more ions to be doped may be used.

The light emitting material may comprise a low molecular weight compound and a polymer compound, and preferably, comprises a triplet light emitting complex and a polymer compound.

As the triplet light emitting complex, iridium complexes represented by the formulas Ir-1 to Ir-5 are preferable.

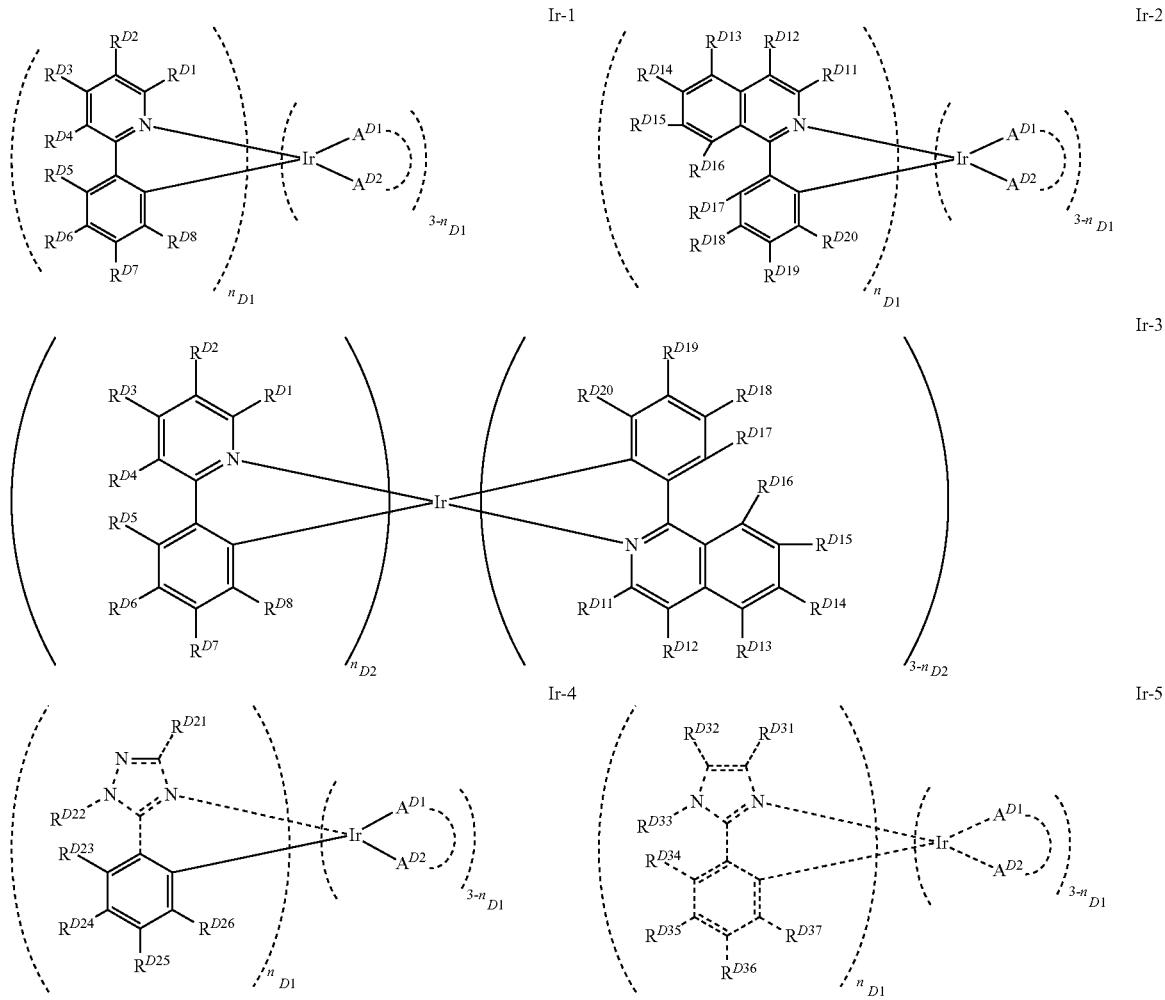

[Light Emitting Material]

The light emitting material is classified into low molecular weight compounds and polymer compounds. The light emitting material optionally has a crosslinkable group.

The low molecular weight compound includes, for example, naphthalene and derivatives thereof, anthracene and derivatives thereof, perylene and derivatives thereof, and, triplet light emitting complexes having iridium, platinum or europium as the central metal.

The polymer compound includes, for example, polymer compounds comprising a phenylene group, a naphthalenediyl group, an anthracenediyl group, a fluorenediyl group, a phenanthrenediyl group, dihydrophenanthrenediyl group, a group represented by the formula (X), a carbazolediyl group, a phenoxazinediyl group, a phenothiazinediyl group, a pyrenediyl group and the like.

[Wherein, $R^{D1}$ to $R^{D8}$, $R^{D11}$ to $R^{D20}$, $R^{D21}$ to $R^{D26}$ and $R^{D31}$ to $R^{D37}$ each independently represent a hydrogen atom, an alkyl group, a cycloalkyl group, an alkoxy group, a cycloalkoxy group, an aryl group, an aryloxy group, a monovalent heterocyclic group or a halogen atom, and these groups each optionally have a substituent. When a plurality of to $R^{D1}$ to $R^{D8}$, $R^{D11}$ to $R^{D20}$, $R^{D21}$ to $R^{D26}$ and $R^{D31}$ to $R^{D37}$ are present, they may be the same or different at each occurrence.

-$A^{D1}$-$A^{D2}$- represents an anionic bidentate ligand, and $A^{D1}$ and $A^{D2}$ each independently represent a carbon atom, an oxygen atom or a nitrogen atom linking to an iridium atom, and these atoms each may be an atom consisting a ring. When a plurality of -$A^{D1}$-$A^{D2}$- are present, they may be the same or different.

$n_{D1}$ represents 1, 2 or 3, and $n_{D2}$ represents 1 or 2.]

In the triplet light emitting complex represented by the Ir-1, at least one of $R^{D1}$ to $R^{D8}$ is preferably a group represented by the formula (D-A).

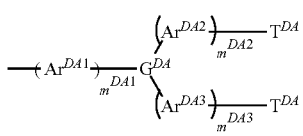
(D-A)

[wherein, $m^{DA1}$, $m^{DA2}$ and $m^{DA3}$ each independently represent an integer of 0 or more.

$G^{DA}$ represents a nitrogen atom, an aromatic hydrocarbon group or a heterocyclic group, and these groups each optionally have a substituent.

$Ar^{DA1}$, $Ar^{DA2}$ and $Ar^{DA3}$ each independently represent an arylene group or a divalent heterocyclic group, and these groups each optionally have a substituent. When a plurality of $Ar^{DA1}$, $Ar^{DA2}$ and $Ar^{DA3}$ are present, they may be the same or different at each occurrence.

$T^{DA}$ represents an aryl group or a monovalent heterocyclic group, and these groups each optionally have a substituent. The plurality of $T^{DA}$ may be the same or different.]

$m^{DA1}$, $m^{DA2}$ and $m^{DA3}$ usually an integer of 10 or less, preferably an integer of 5 or less, more preferably 0 or 1. It is preferable that $m^{DA1}$, $m^{DA2}$ and $m^{DA3}$ are the same integer.

$G^{DA}$ is preferably a group represented by the formula (GDA-11) to (GDA-15), and these groups each optionally have a substituent.

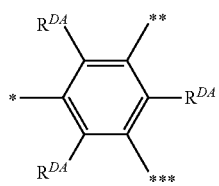
(GDA-11)

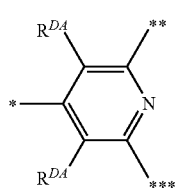
(GDA-12)

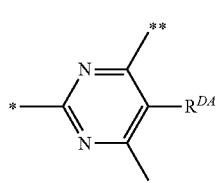
(GDA-13)

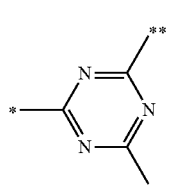
(GDA-14)

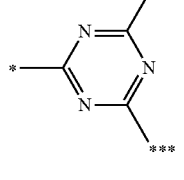
(GDA-15)

[wherein,

*,  and * each represent a linkage to $Ar^{DA1}$, $Ar^{DA2}$ and $Ar^{DA3}$.

$R^{DA}$ represents a hydrogen atom, an alkyl group, a cycloalkyl group, an alkoxy group, a cycloalkoxy group, an aryl group or a monovalent heterocyclic group, and these groups each optionally further have a substituent. When a plurality $R^{DA}$ are present, they may be the same or different.]

$R^{DA}$ is preferably a hydrogen atom, an alkyl group, a cycloalkyl group, an alkoxy group or a cycloalkoxy group, more preferably a hydrogen atom, an alkyl group or cycloalkyl group, and these groups each optionally have a substituent.

$Ar^{DA1}$, $Ar^{DA2}$ and $Ar^{DA3}$ preferably groups represented by the formulae (ArDA-1) to (ArDA-3).

(ArDA-1)

(ArDA-2)

(ArDA-3)

[wherein, $R^{DA}$ represents the same meaning as described above.

$R^{DB}$ represents a hydrogen atom, an alkyl group, a cycloalkyl group, an aryl group or a monovalent heterocyclic group, and these groups each optionally have a substituent. When a plurality of $R^{DB}$ are present, they may be the same or different.]

$T^{DA}$ is preferably groups represented by the formulae (TDA-1) to (TDA-3).

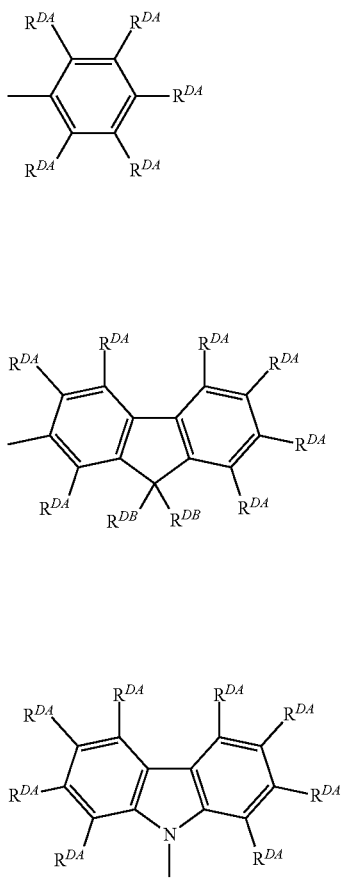

(TDA-1)

(TDA-2)

(TDA-3)

[wherein, $R^{DA}$ and $R^{DB}$ represent the same meaning described above.]

In the formula Ir-2, at least one of $R^{D11}$ to $R^{D20}$ is preferably a group represented by the formula (D-A).

In the formula Ir-3, at least one of $R^{D1}$ to $R^{D8}$ and $R^{D11}$ to $R^{D20}$ preferably a group represented by the formula (D-A).

In the formula Ir-4, at least one of $R^{D21}$ to $R^{D26}$ is preferably a group represented by the formula (D-A).

In the formula Ir-5, at least one of $R^{D31}$ to $R^{D37}$ is preferably a group represented by the formula (D-A).

The group represented by the formula (D-A) is preferably a group represented by the formula (D-A1) to (D-A3).

(D-A1)

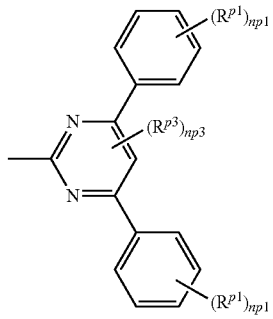

(D-A2)

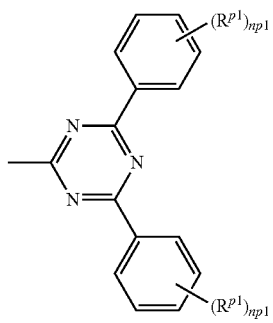

(D-A3)

[wherein, $R^{p1}$, $R^{p2}$ and $R^{p3}$ each independently represent an alkyl group, a cycloalkyl group, an alkoxy group, a cycloalkoxy group or a halogen atom. When a plurality of $R^{p1}$ and $R^{p2}$ are present, they may be the same or different at each occurrence.

np1 represents an integer of 0 to 5, np2 represents an integer of 0 to 3, and np3 represents 0 or 1. The plurality of np1 may be the same or different.]

np1 is preferably 0 or 1, more preferably 1. np2 is preferably 0 or 1, more preferably 0. np3 is preferably 0.

$R^{p1}$, $R^{p2}$ and $R^{p3}$ are preferably an alkyl group or a cycloalkyl group.

The anionic bidentate ligand represented toy -$A^{D1}$-$A^{D2}$- includes, for example, ligands represented by the following formulae.

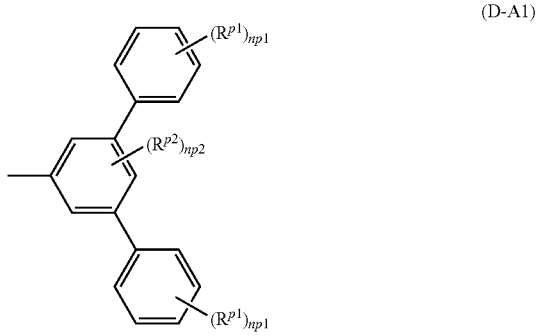

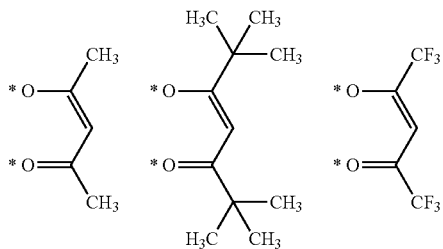

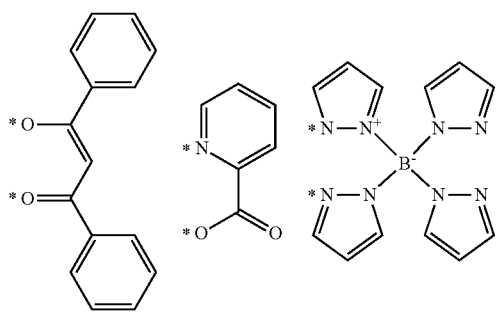
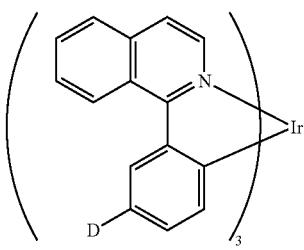

[wherein, * represents a position linking to Ir.]

The metal complex represented by the formula Ir-1 is preferably a metal complex represented by the formula Ir-11 to Ir-13. The metal complex represented by the formula Ir-2 is preferably a metal complex represented by the formula Ir-21. The metal complex represented by the formula Ir-3 is preferably a metal complex represented by the formula Ir-31 to Ir-33. The metal complex represented by the formula Ir-4 is preferably a metal complex represented by the formula Ir-41 to Ir-43. The metal complex represented by the formula Ir-5 is preferably a metal complex represented by the formula Ir-51 to Ir-53.

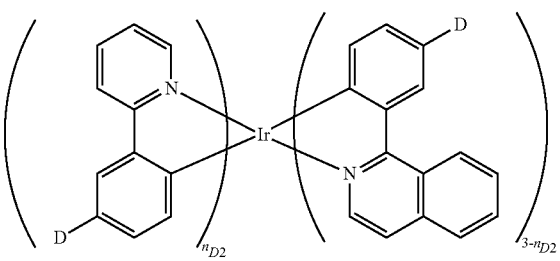

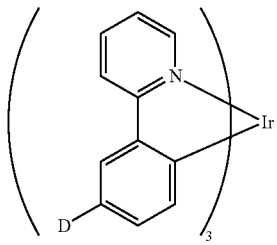

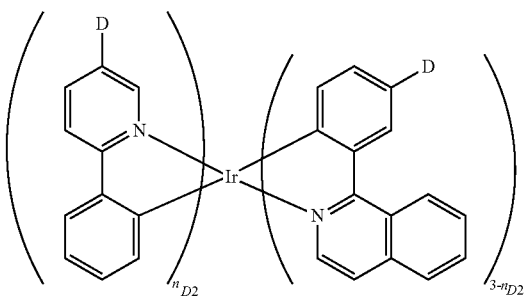

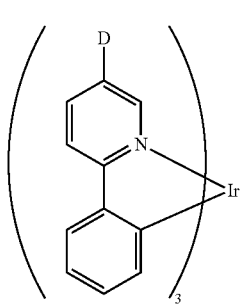

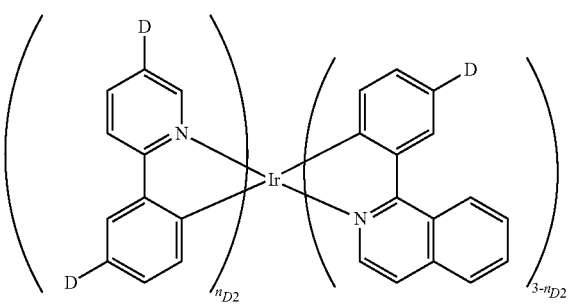

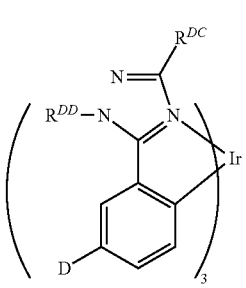

Ir-42

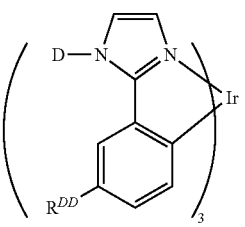

Ir-43

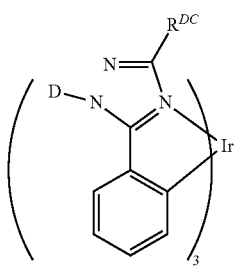

Ir-51

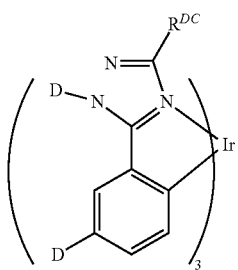

Ir-52

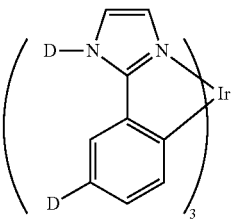

Ir-53

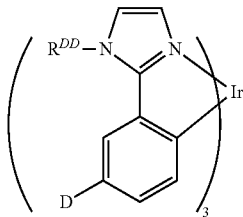

[wherein, D represents a group represented by the formula (D-A). The plurality of D are the same or different. $n_{D2}$ represents 1 or 2. $R^{DC}$ represents a hydrogen atom, an alkyl group, a cycloalkyl group, an aryl group or a monovalent heterocyclic group, and these groups each optionally have a substituent. The plurality of $R^{DC}$ are the same or different. $R^{DD}$ represents an alkyl group, a cycloalkyl group, an aryl group or a monovalent heterocyclic group, and these groups each optionally have a substituent. The plurality of $R^{DD}$ are the same or different.]

The triplet light emitting complex includes, for example, metal complexes listed below, and COM-4 is preferable.

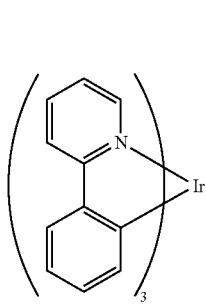
Ir(ppy)$_3$

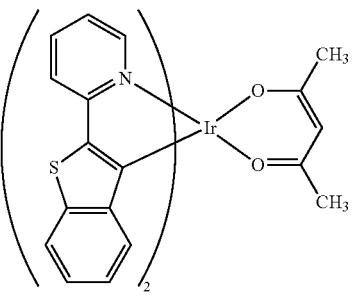
Btp$_2$Ir(acac)

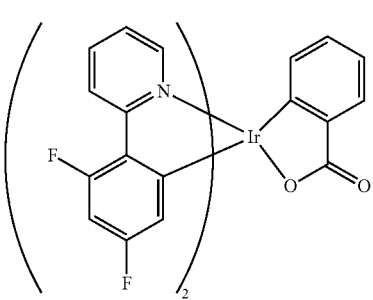
FIrpic

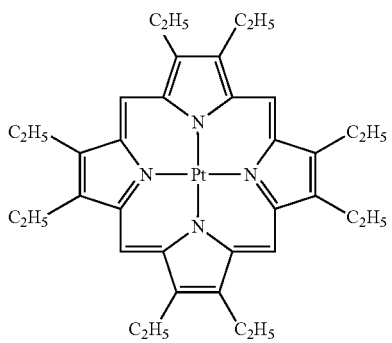
PtOEP

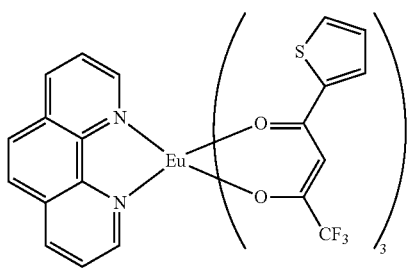
Eu(TTA)$_3$phen

-continued
COM-1
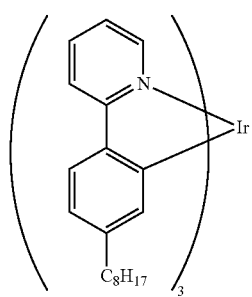
COM-2
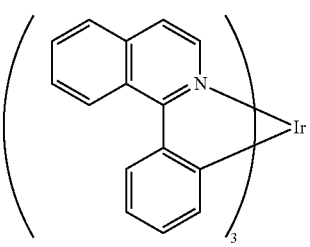
COM-3
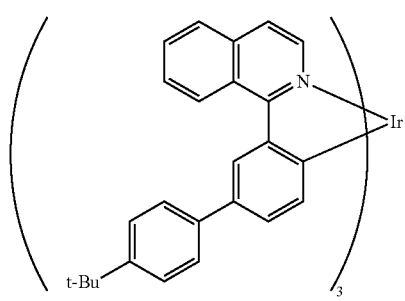
COM-4
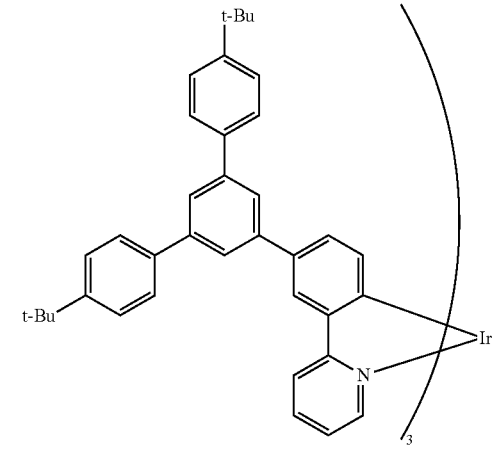
COM-5
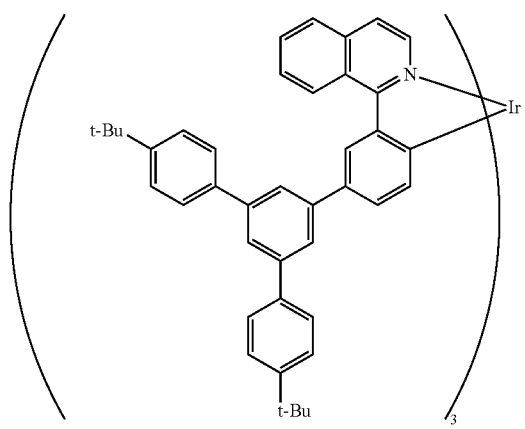
COM-6
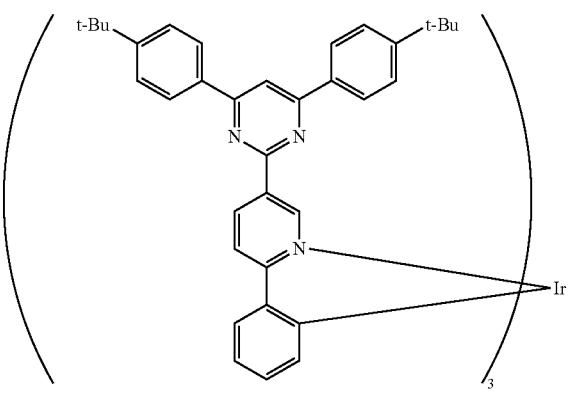
COM-7
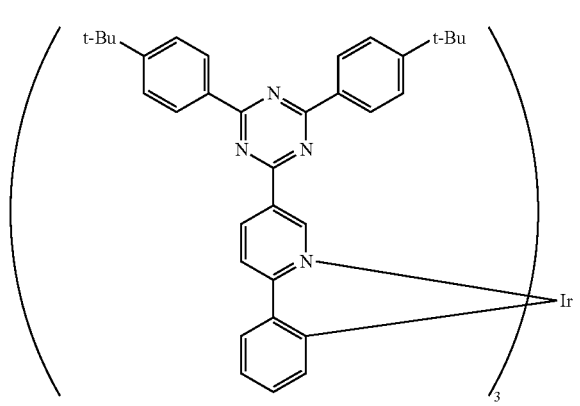

-continued
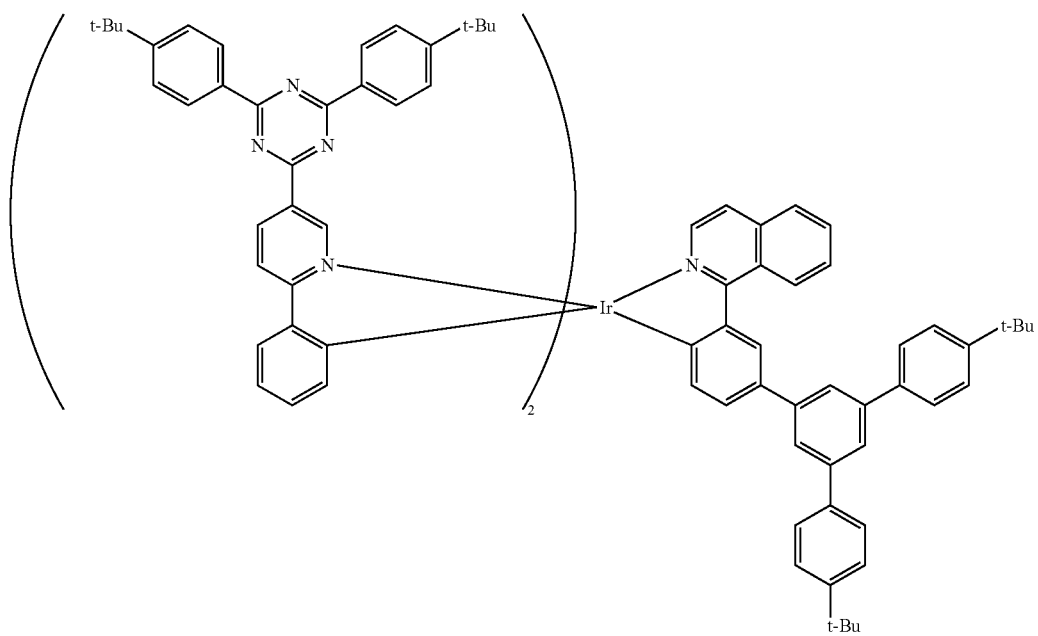
COM-8
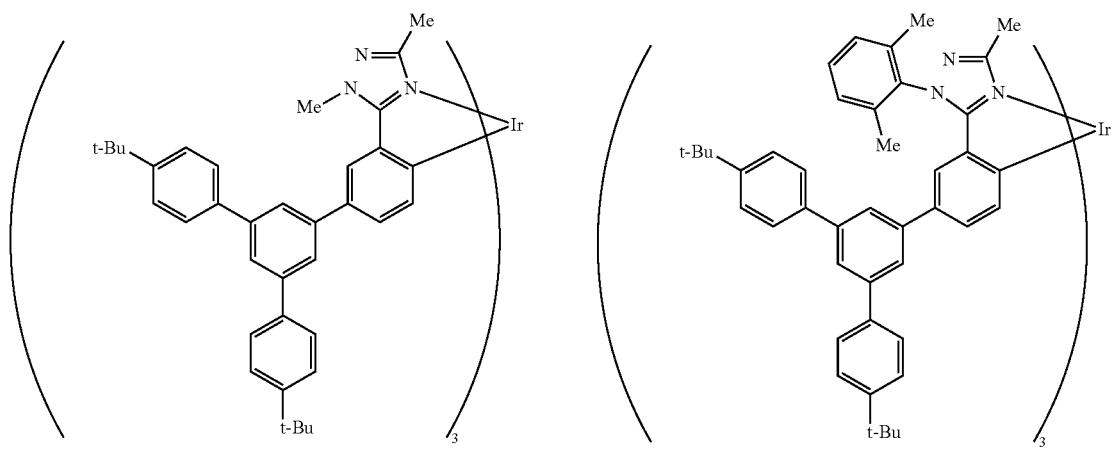
COM-10  COM-11
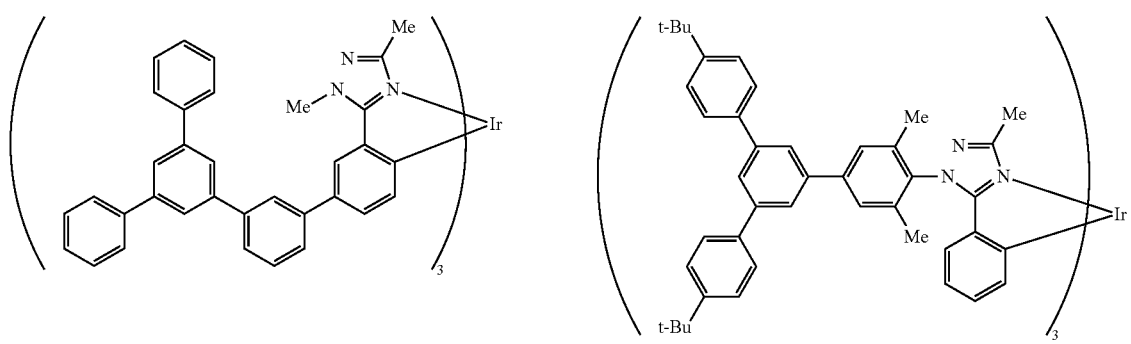
COM-12  COM-13

-continued
COM-14
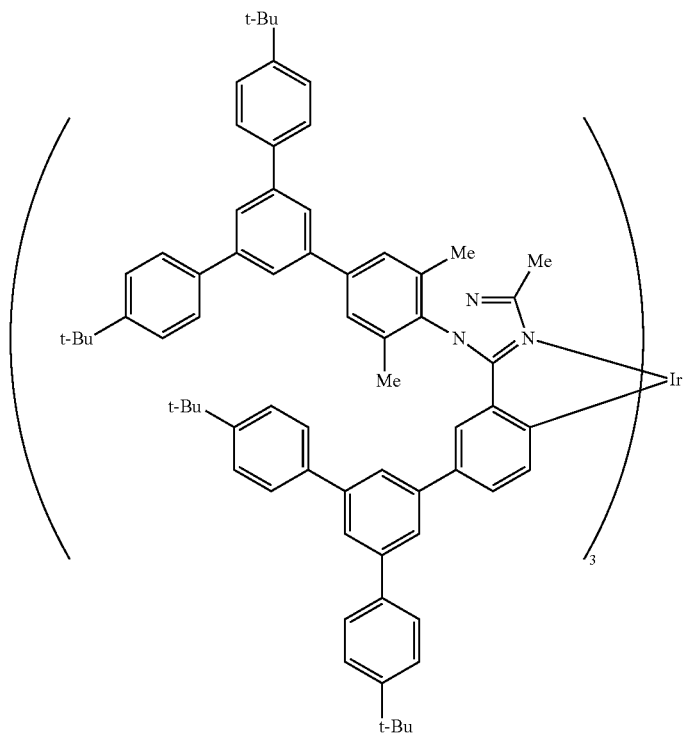
COM-15 COM-16
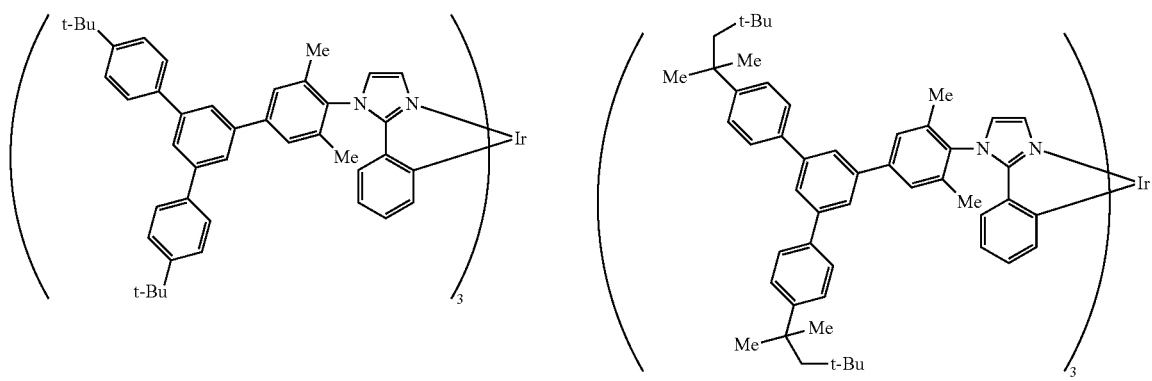
COM-17 COM-18
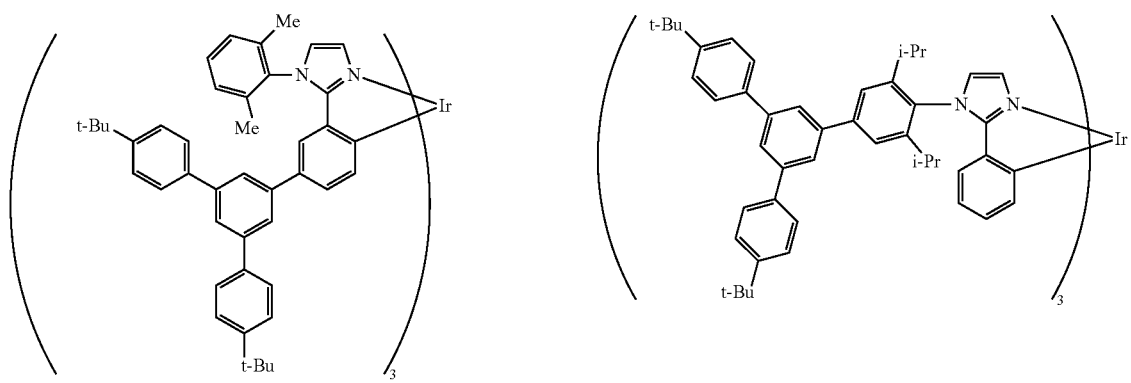

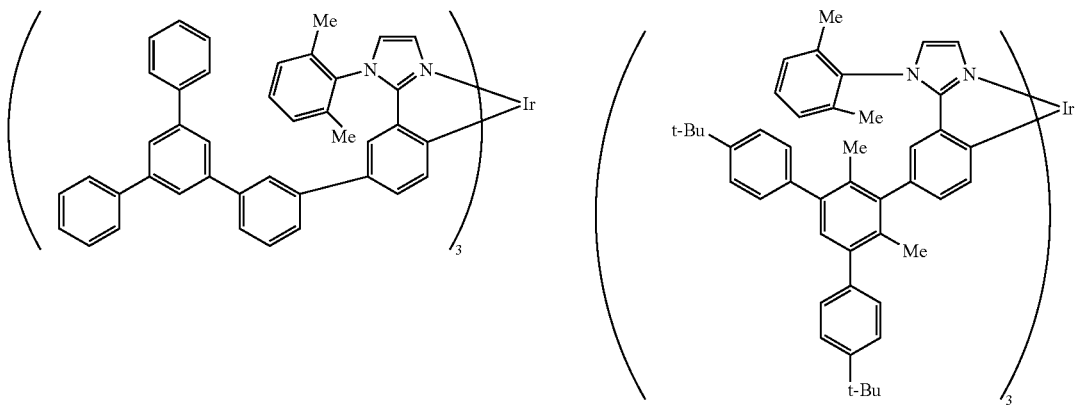

In the composition of the present invention, the compounding amount of the light emitting material is usually 0.1 to 400 parts by weight with respect to 100 parts by weight of the polymer compound of the present invention.

[Antioxidant]

The antioxidant may advantageously be one which is soluble in the same solvent as for the polymer compound of the present invention and does not disturb light emission and charge transportation, and the examples thereof include phenol antioxidants and phosphorus-based antioxidants.

In the composition of the present invention, the compounding amount of the antioxidant is usually 0.001 to 10 parts by weight with respect to 100 parts by weight of the polymer compound of the present invention.

The antioxidant may be used singly or two or more antioxidants may be used in combination.

<Film>

The film is classified into a film comprising the polymer compound of the present invention and an insolubilized film produced by insolubilizing the polymer compound of the present invention in a solvent by crosslinking. The insolubilized film is a film produced by crosslinking the polymer compound of the present invention by an external stimulus such as heating, light irradiation and the like. Since the insolubilized film is substantially insoluble in a solvent, it can be suitably used for lamination in a light emitting device.

The heating temperature for crosslinking the film is usually 25 to 300° C., and because the light emission efficiency is improved, preferably 50 to 250° C., more preferably 150 to 200° C.

The kind of light used in light irradiation for crosslinking the film includes, for example, ultraviolet light, near-ultraviolet light and visible light.

The film is suitable as a hole transporting layer or a hole injection layer in a light emitting device.

The film can be fabricated, for example, by a spin coating method, a casting method, a micro gravure coating method, a gravure coating method, a bar coating method, a roll coating method, a wire bar coating method, a dip coating method, a spray coating method, a screen printing method, a flexo printing method, an offset printing method, an inkjet printing method, a capillary coating method or a nozzle coating method, using the ink.

The thickness of the film is usually 1 nm to 10 μm.

<Light Emitting Device>

The light emitting device of the present invention is a light emitting device such as an organic electroluminescent device produced by using the polymer compound of the present invention, and the light emitting device includes, for example, light emitting devices comprising the polymer compound of the present invention, and light emitting devices produced by intramolecularly or intermolecularly crosslinking the polymer compound of the present invention or produced by crosslinking the polymer compound in both modes.

The constitution of the light emitting device of the present invention comprises, for example, electrodes consisting of an anode and a cathode, and a layer produced by using the polymer compound of the present invention disposed between the electrodes.

[Layer Constitution]

The layer produced by using the polymer compound of the present invention is usually at least one selected from a light emitting layer, a hole transporting layer, a hole injection layer, an electron transporting layer and an electron, injection layer, preferably a hole transporting layer. These layers comprise a light emitting material, a hole transporting material, a hole injection material, an electron transporting material and an electron injection material, respectively. These layers can be formed by the same method as the above-described film fabrication using inks prepared by dissolving a light emitting material, a hole transporting material, a hole injection material, an electron transporting material and an electron injection material, respectively, in the solvent described above.

The light emitting device comprises a light emitting layer between an anode and a cathode. The light emitting device of the present invention preferably comprises at least one of a hole injection layer and a hole transporting layer between an anode and a light emitting layer from the standpoint of hole injectability and hole transportability, and preferably comprises at least one of an electron injection layer and an electron transporting layer between a cathode and a light emitting layer from the standpoint of electron injectability and electron transportability.

The material of a hole transporting layer, an electron transporting layer, a light emitting layer, a hole injection layer and an electron injection layer includes the above-described hole transporting materials, electron transporting materials, light emitting materials, hole injection materials and electron injection materials, respectively, in addition to the polymer compound of the present invention.

When the material of a hole transporting layer, the material of an electron transporting layer and the material of a light emitting layer are soluble in a solvent which is used in forming a layer adjacent to the hole transporting layer, the electron transporting layer and the light emitting layer, respectively, in fabrication of a light emitting device, it is preferable that the materials have a crosslinkable group to avoid dissolution of the materials in the solvent. After forming the layers using the materials having a crosslinkable group, the layers can be insolubilized by crosslinking the crosslinkable group.

Methods of forming respective layers such as a light emitting layer, a hole transporting layer, an electron transporting layer, a hole injection layer and an electron injection layer in the light emitting device of the present invention include, for example, a method of vacuum vapor deposition from a powder and a method of film formation from solution or melted state when a low molecular weight compound is used, and, for example, a method of film formation from solution or melted state when a polymer compound is used.

The order and the number of layers to be laminated and the thickness of each layer may be controlled in view of light emission efficiency and device life.

[Substrate/Electrode]

The substrate in the light emitting device may advantageously be a substrate on which an electrode can be formed and which does not chemically change in forming an organic layer, and is a substrate made of a material such as, for example, glass, plastic and silicon. In the case of an opaque substrate, it is preferable that an electrode most remote from the substrate is transparent or semi-transparent.

The material of the anode includes, for example, electrically conductive metal oxides and semi-transparent metals, preferably, indium oxide, zinc oxide and tin oxide; electrically conductive compounds such as indium.tin.oxide (ITO) and indium.zinc.oxide; a composite of silver, palladium and copper (APC); NESA, gold, platinum, silver and copper.

The material of the cathode includes, fox example, metals such as lithium, sodium, potassium, rubidium, cesium, beryllium, magnesium, calcium, strontium, barium, aluminum, zinc and indium; alloys composed of two or more of them; alloys composed of one or more of them and at least one of silver, copper, manganese, titanium, cobalt, nickel, tungsten, and tin; and graphite and graphite intercalation compounds. The alloy includes, for example, a magnesium-silver alloy, a magnesium-indium alloy, a magnesium-aluminum alloy, an indium-silver alloy, a lithium-aluminum alloy, a lithium-magnesium alloy, a lithium-indium, alloy and a calcium-aluminum alloy.

The anode and the cathode may each take a lamination structure composed of two or more layers.

[Use]

For producing planar light emission by using a light emitting device, a planar anode and a planar cathode are disposed so as to overlap with each other. Patterned light-emission can be produced by a method of placing a mask with a patterned window on the surface of a planer light emitting device, a method of forming extremely thick a layer intended to be a non-light emitting, thereby having the layer essentially no-light emitting or a method of forming an anode, a cathode or both electrodes in a patterned shape. By forming a pattern with any of these methods and disposing certain electrodes so as to switch ON/OFF independently, a segment type display capable of displaying numbers and letters and the like is provided. For producing a dot matrix display, both an anode and a cathode are formed in a stripe shape and disposed so as to cross with each other. Partial color display and multi-color display are made possible by a method of printing separately certain polymer compounds showing different emission or a method of using a color filter or a fluorescence conversion filter. The dot matrix display can be passively driven, or actively driven combined with TFT and the like. These displays can be used in computers, television sets, portable terminals and the like. The planar light emitting device can be suitably used as a planer light source for backlight of a liquid crystal display or as a planar light source for illumination. If a flexible substrate is used, it can be used also as a curved light source and a curved display.

EXAMPLES

The present invention will be illustrated further in detail by examples below, but the present invention is not limited to these examples.

In the present examples, the polystyrene-equivalent number average molecular weight (Mn) and the polystyrene-equivalent weight average molecular weight (Mw) of a polymer compound were measured by size exclusion chromatography (SEC) (manufactured by Shimadzu Corp., trade name; LC-10Avp). SEC measurement conditions are as described below.

[Measurement Condition]

The polymer compound to be measured was dissolved in THF at a concentration of about 0.05 wt %, and 10 µL of the solution was injected into SEC. As the mobile phase of SEC, tetrahydrofuran was used and allowed to flow at a flow rate of 2.0 mL/min. As the column, PLgel MIXED-B (manufactured by Polymer Laboratories) was used. As the detector, UV-VIS detector (manufactured by Shimadzu Corp., trade name: SPD-10Avp) was used.

Measurement of liquid cbromatograph mass spectrometry (LC-MS) was carried out according to the following method.

A measurement sample was dissolved in chloroform or THF so as to give a concentration of about 2 mg/mL, and about 1 µL of the solution was injected into LC-MS (manufactured by Agilent Technologies, trade name: 1100LCMSD). As the mobile phase of LC-MS, acetonitrile and THF were used while changing the ratio thereof and allowed to flow at a flow rate of 0.2 mL/min. As the column, L-column 2 ODS (3 µm) (manufactured by Chemicals Evaluation and Research Institute, internal diameter: 2.1 mm, length: 100 mm, particle size: 3 µm) was used.

Measurement of NMR was carried out according to the following method.

5 to 10 mg of a measurement sample was dissolved in about 0.5 mL of deuterated chloroform ($CDCl_3$), deuterated tetrahydrofuran (THF-$d_8$) or deuterated methylene chloride ($CD_2Cl_2$), and measurement was performed using an NMR apparatus (manufactured by Varian, Inc., trade name: MERCURY 300).

As the index of the purity of a compound, a value of the high performance liquid chromatography (HPLC) area percentage was used. This value is a value in high performance liquid chromatography (HPLC, manufactured by Shimadzu Corp., trade name: LC-20A) at 254 nm, unless otherwise state. In this operation, the compound to be measured was dissolved in THF or chloroform so as to give a concentration of 0.01 to 0.2 wt %, and depending on the concentration, 1 to 10 µL of the solution was injected into HPLC. As the mobile phase of HPLC, acetonitrile and THF were used and allowed to flow at a flow rate of 1 mL/min as gradient analysis of acetonitrile/THF=100/0 to 0/100 (volume ratio). As the column, Kaseisorb LC ODS 2000 (manufactured by Tokyo Chemical Industry Co., Ltd.) or an ODS column having an equivalent performance was used. As the detector, a photo diode array detector (manufactured by Shimadzu Corp., trade name: SPD-M20A) was used.

Synthesis Example 1

Synthesis of Compound Ma3

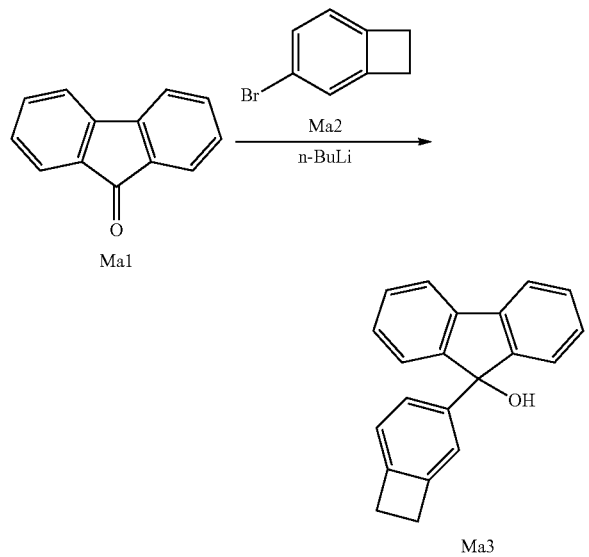

A gas in a flask equipped with a stirrer was purged with a nitrogen gas, then, a compound Ma2 (64.6 g) and tetrahydrofuran (615 mL) were added, and the mixture was cooled down to −70° C. Into this, a n-butyllithium hexane solution (1.6 M, 218 mL) was dropped over a period of 1 hour, then, the mixture was stirred at −70° C. for 2 hours. To this, a compound Ma1 (42.1 g) was added in several batches, then, the mixture was stirred at −70° C. for 2 hours. Into this, methanol (40 mL) was dropped over a period of 1 hour, then, the mixture was heated up to room temperature. Thereafter, the solvent was distilled off by concentrating under reduced pressure, and toluene and water were added. Thereafter, an aqueous layer was separated and the resultant organic layer was washed with water. The resultant organic layer was concentrated under reduced pressure, and the resultant residue was purified by using a silica gel column (developing solvent: a mixed solvent of hexane and ethyl acetate), thereby obtaining 71 g of a compound Ma3 as a colorless oil. The compound Ma3 had an HPLC area percentage value (UV: 254 nm) of 97.5%. This operation was repeated, thereby obtaining a necessary amount of the compound Ma3.

$^1$H-NMR (CDCl$_3$, 300 MHz): δ (ppm): 2.43 (1H, s), 3.07-3.13 (4H, m), 6.95 (1H, d), 7.07 (1H, s), 7.18-7.28 (3H, m), 7.28-7.40 (4H, m), 7.66 (2H, s).

Synthesis Example 2

Synthesis of Compound Ma4

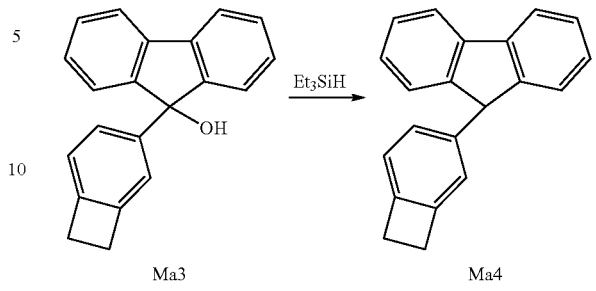

A gas in a flask equipped with a stirrer was purged with a nitrogen gas, then, the compound Ma3 (72.3 g), toluene (723 mL) and triethylsilane (118.0 g) were added, and the mixture was heated up to 70° C. Into this, methanesulfonic acid (97.7 g) was dropped over a period of 1.5 hours, then, the mixture was stirred at 70° C. for 0.5 hours. Thereafter, the mixture was cooled down to room temperature, and toluene (1 L) and water (1 L) were added, then, an aqueous layer was separated. The resultant organic layer was washed with water, a 5 wt % sodium hydrogen carbonate aqueous solution and water in this order. The resultant organic layer was concentrated under reduced pressure, and the resultant coarse product was recrystallized from a mixed solvent of toluene and ethanol, thereby obtaining 51.8 g of a compound Ma4 as a white solid. The compound Ma4 had an HPLC area percentage value (UV: 254 nm) of 99.5% or more. This operation was repeated, thereby obtaining a necessary amount of the compound Ma4.

$^1$H-NMR (CDCl$_3$, 300 MHz): δ (ppm): 3.03-3.14 (4H, m), 4.99 (1H, s), 6.68 (1H, s), 6.92-7.01 (2H, m), 7.20-7.28 (2H, m), 7.29-7.38 (4H, m), 7.78 (2H, d).

Synthesis Example 3

Synthesis of Compound Mb3

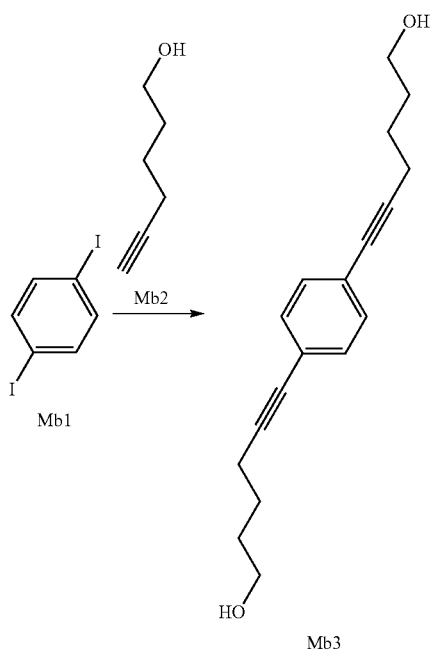

A gas in a flask equipped with a stirrer was purged with a nitrogen gas, then, a compound Mb1 (185.0 g), a compound Mb2 (121.1 g), copper(I) iodide (3.2 g), dichloromethane (185 mL) and triethylamine (2.59 L) were added, and the mixture was heated up to the reflux temperature. Thereafter, the mixture was stirred at the reflux temperature for 0.5 hours, and cooled down to room temperature. To this was added dichloromethane (1.85 L), then, the mixture was filtrated through a filter paved with celite. To the resultant filtrate was added a 10 wt % sodium hydrogen carbonate aqueous solution, then, an aqueous layer was separated. The resultant organic layer was washed with water twice, washed with a saturated sodium chloride aqueous solution, then, magnesium sulfate was added. The resultant mixture was filtrated, and the resultant filtrate was concentrated under reduced pressure. The resultant residue was purified by using a silica gel column (developing solvent: a mixed solvent of chloroform and ethyl acetate), thereby obtaining a coarse product. The resultant coarse product was dissolved in ethanol (1.4 L), then, activated carbon (5 g) was added, and the mixture was filtrated. The resultant filtrate was concentrated under reduced pressure, and the resultant residue was recrystallized from hexane, thereby obtaining 99.0 g of a compound Mb3 as a white solid. The compound Mb3 had an HPLC area percentage value (UV: 254 nm) of 99.5% or more. This operation was repeated, thereby obtaining a necessary amount of the compound Mb3.

$^1$H-NMR (DMSO-d6, 300 MHz) δ (ppm): 1.52-1.55 (8H, m), 2.42 (4H, t), 3.38-3.44 (4H, m), 4.39-4.43 (2H, m), 7.31 (4H, s).

Synthesis Example 4

Synthesis of Compound Mb4

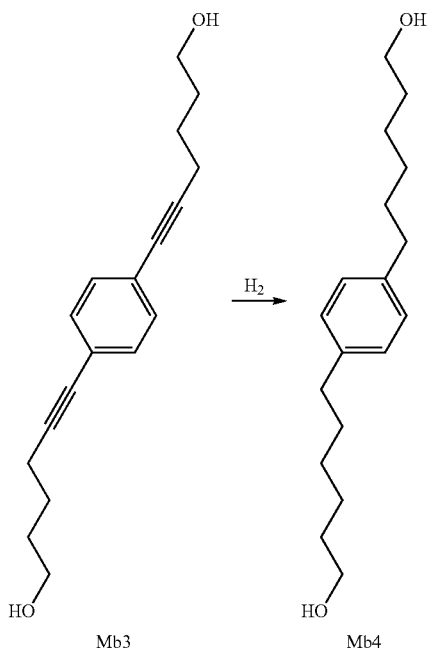 [SMILES: OCCCCC#Cc1ccc(C#CCCCCO)cc1 ; "H2" ; OCCCCCCc1ccc(CCCCCCO)cc1]

A gas in a flask equipped with a stirrer was purged with a nitrogen gas, then, the compound Mb3 (110.0 g), ethanol (1.65 L) and palladium/carbon (palladium weight: 10%) (11.0 g) were added, and the mixture was heated up to 30° C. Thereafter, a gas in the flask was purged with a hydrogen gas. Thereafter, the mixture was stirred at 30° C. for 3 hours while feeding a hydrogen gas into the flask. Thereafter, a gas in the flask was purged with a nitrogen gas. The resultant mixture was filtrated, and the resultant filtrate was concentrated under reduced pressure. The resultant residue was purified by using a silica gel column (developing solvent: a mixed solvent of chloroform and ethyl acetate), thereby obtaining a coarse product. The resultant coarse product was recrystallized from hexane, thereby obtaining 93.4 g of a compound Mb4 as a white solid. The compound Mb4 had an HPLC area percentage value (UV: 254 nm) of 98.3%.

$^1$H-NMR (CDCl$_3$, 300 MHz) δ (ppm): 1.30-1.40 (8H, m), 1.55-1.65 (8H, m), 2.58 (4H, t), 3.64 (4H, t), 7.09 (4H, s).

$^{13}$C-NMR (CDCl$_3$, 75 MHz) δ (ppm): 25.53, 28.99, 31.39, 32.62, 35.37, 62.90, 128.18, 139.85.

Synthesis Example 5

Synthesis of Compound Mb5

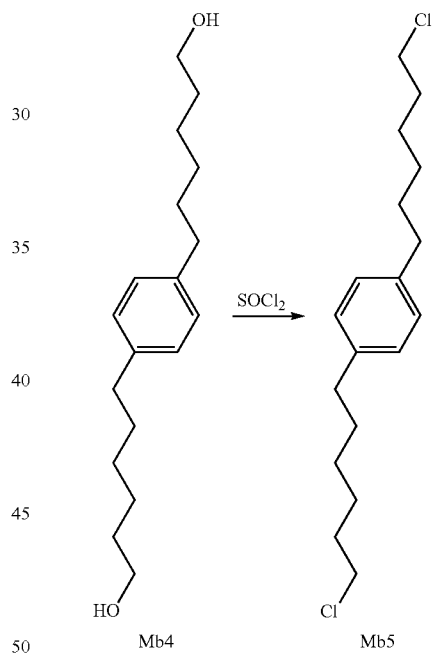

A gas in a flask equipped with a stirrer was purged with a nitrogen gas, then, the compound Mb4 (61.0 g), pyridine (0.9 g) and toluene (732 mL) were added, and the mixture was heated up to 60° C. Into this, thionyl chloride (91.4 g) was dropped over a period of 1.5 hours, then, the mixture was stirred at 60° C. for 5 hours. The resultant mixture was cooled down to room temperature, then, concentrated under reduced pressure. The resultant residue was purified by using a silica gel column (developing solvent: a mixed solvent of hexane and ethyl acetate), thereby obtaining 64.3 g of a compound Mb5 as a colorless oil. The compound Mb5 had an HPLC area percentage value (UV: 254 nm) of 97.2%.

$^1$H-NMR (CDCl$_3$, 300 MHz) δ (ppm): 1.35-1.40 (4H, m), 1.41-1.50 (4H, m), 1.60-1.68 (4H, m), 1.75-1.82 (4H, m), 2.60 (4H, t), 3.55 (4H, t), 7.11 (4H, s).

Synthesis Example 6

Synthesis of Compound Mb6

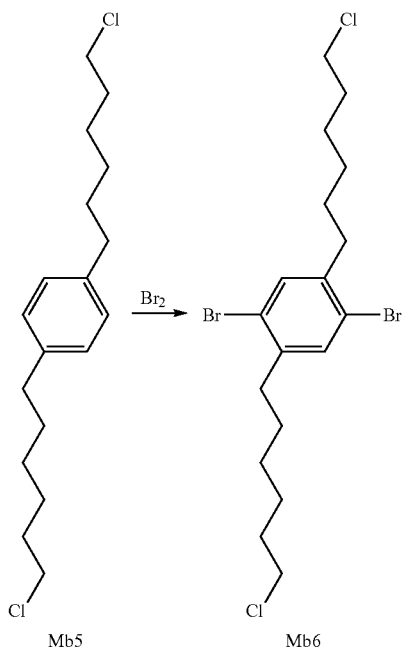

Mb5 → Mb6

A gas in a flask equipped with a stirrer was purged with a nitrogen gas, then, the compound Mb5 (42.0 g), an iron powder (1.7 g), iodine (0.3 g) and dichloromethane (800 mL) were added. Thereafter, the whole flask was light-shielded, and cooled at 0 to 5° C. Into this, a mixed liquid of bromine (44.7 g) and dichloromethane (200 mL) was dropped over a period of 1 hour, then, the mixture was stirred at 0 to 5° C. overnight. The resultant mixed liquid was added to water (1.2 L) cooled at 0 to 5° C., then, an organic layer was separated. The resultant organic layer was washed with a 10 wt % sodium thiosulfate aqueous solution, and further, washed with a saturated sodium chloride aqueous solution and water in this order. To the resultant organic layer was added sodium sulfate, then, the mixture was filtrated, and the resultant filtrate was concentrated under reduced pressure. The resultant residue was purified by using a silica gel column (developing solvent; hexane), thereby obtaining a coarse product. The resultant coarse product was recrystallized from hexane, thereby obtaining 47.0 g of a compound Mb6 as a white solid. The compound Mb6 had an HPLC area percentage value (UV: 254 nm) of 98.3%.

$^1$H-NMR (CDCl$_3$, 300 MHz) δ (ppm): 1.38-1.45 (4H, m), 1.47-1.55 (4H, m), 1.57-1.67 (4H, m), 1.77-1.84 (4H, m), 2.66 (4H, t), 3.55 (4H, t), 7.36 (2H, s).

Synthesis Example 7

Synthesis Oil Compound Mb7

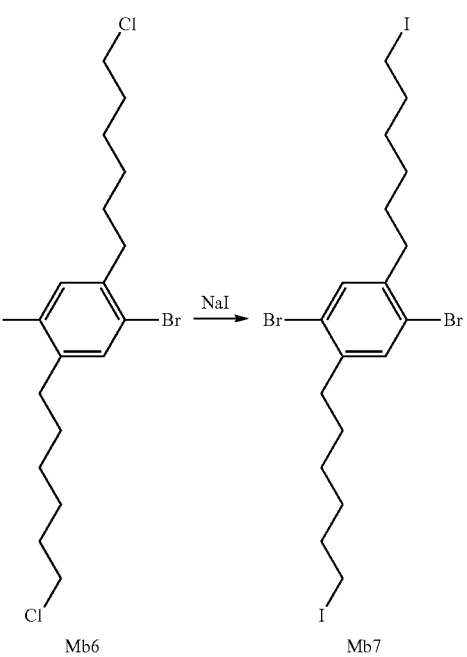

Mb6 → Mb7

A gas in a flask equipped with a stirrer was purged with a nitrogen gas, then, sodium iodide (152.1 g) and acetone (600 mL) were added, and the mixture was stirred at room temperature for 0.5 hours. To this was added the compound Mb6 (40.0 g), then, the mixture was heated up to the reflux temperature, and stirred at the reflux temperature for 24 hours. Thereafter, the mixture was cooled down to room temperature, and the resultant mixed liquid was added to water (1.2 L). The deposited solid was separated by filtration, then, washed with water, thereby obtaining a coarse product. The resultant coarse product was recrystallized from a mixed liquid of toluene and methanol, thereby obtaining 46.0 g of a compound Mb7 as a white solid. The compound Mb7 had an HPLC area percentage value (UV: 254 nm) of 99.4%. This operation was repeated, thereby obtaining a necessary amount of the compound Mb7.

$^1$H-NMR (CDCl$_3$, 300 MHz) δ (ppm): 1.35-1.50 (8H, m), 1.57-1.65 (4H, m), 1.80-1.89 (4H, m), 2.65 (4H, t), 3.20 (4H, t), 7.36 (2H, s).

Example 1

Synthesis of Compound Mb8

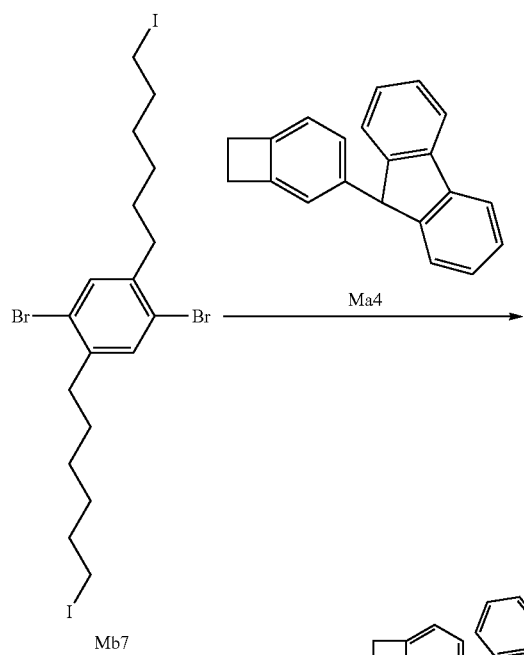

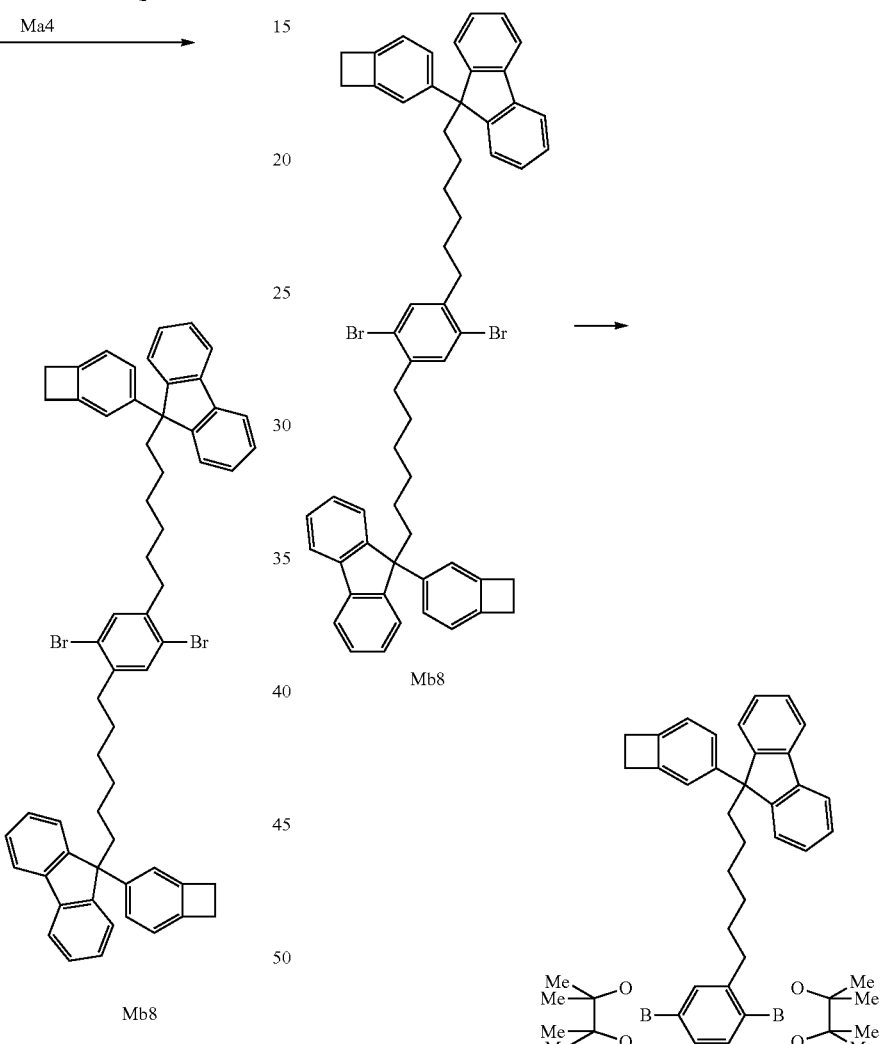

A gas in a flask equipped with a stirrer was purged with a nitrogen gas, then, sodium hydride (60 wt %, dispersed in liquid paraffin) (9.4 g), tetrahydrofuran (110 mL) and the compound Mb7 (63.2 g) were added. To this, a compound Ma4 (55.0 g) was added in several batches, then, the mixture was stirred for 12 hours. To this were added toluene (440 mL) and water (220 mL), then, an aqueous layer was separated. The resultant organic layer was washed with water, then, magnesium sulfate was added. The resultant mixed liquid was filtrated, and the resultant filtrate was concentrated under reduced pressure, thereby obtaining a coarse product. The resultant coarse product was purified by using a silica gel column (developing solvent: a mixed solvent of hexane and toluene). Thereafter, the product was recrystallized from hexane, thereby obtaining 84.1 g of a compound Mb8 as a white solid. The compound Mb8 had an HPLC area percentage value (UV: 254 nm) of 99.5% or more.

$^1$H-NMR (CDCl$_3$, 300 MHz) δ (ppm): 0.70-0.76 (4H, m), 1.10-1.21 (8H, m), 1.32-1.44 (4H, m), 2.39-2.58 (8H, m), 3.00-3.12 (8H, m), 6.82-6.94 (4H, m), 7.00-7.05 (2H, m), 7.17-7.28 (10H, m), 7.30-7.38 (4H, m), 7.71-7.77 (4H, m).

Example 2

Synthesis of Compound MM1

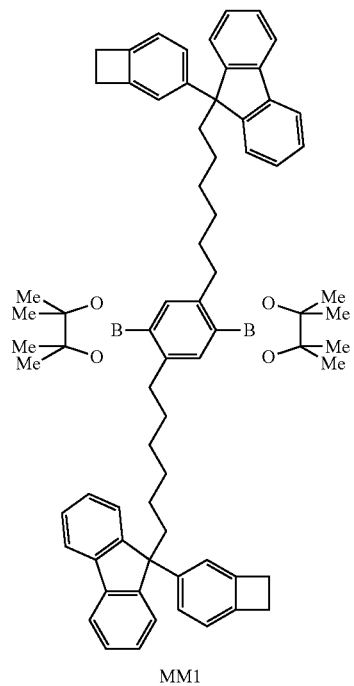

A gas in a flask equipped with a stirrer was purged with a nitrogen gas, then, the compound Mb8 (84.0 g), [1,1'-bis(diphenylphosphino)ferrocene]palladium(II) dichloride dichloromethane adduct (PdCl$_2$(dppf).CH$_2$Cl$_2$, 2.2 g), bispinacolatodiboron (68.3 g), potassium acetate (52.8 g) and cyclopentyl methyl ether (840 mL) were added, and the mixture was heated up to the reflux temperature, then, stirred at the reflux temperature for 5 hours. Thereafter, the mixture was cooled down to room temperature, and toluene (500 mL) and water (300 mL) were added, then, an aqueous layer was separated. The resultant organic layer was washed with water, then, activated carbon (18.5 g) was added. The resultant mixed liquid was filtrated, and the resultant filtrate was concentrated under reduced pressure, thereby obtaining a coarse product. The resultant coarse product was purified by using a silica gel column (developing solvent: a mixed solvent of hexane and toluene). Thereafter, an operation of recrystallizing from a mixed liquid of toluene and acetonitrile was repeated, thereby obtaining 45.8 g of a compound MM1 as a white solid. The compound MM1 had an HPLC area percentage value (UV: 254 nm) of 99.4%.

$^1$H-NMR (CDCl$_3$, 300 MHz) δ (ppm): 0.70-0.76 (4H, m), 1.24-1.40 (36H, m), 2.39-2.48 (4H, m), 2.66-2.75 (4H, m), 3.00-3.10 (8H, m), 6.76-6.90 (4H, m), 7.00-7.05 (2H, m), 7.19-7.30 (8H, m), 7.30-7.36 (4H, m), 7.43 (2H, s), 7.72 (4H, d).

Synthesis Example 8

Synthesis of Compound Mc1

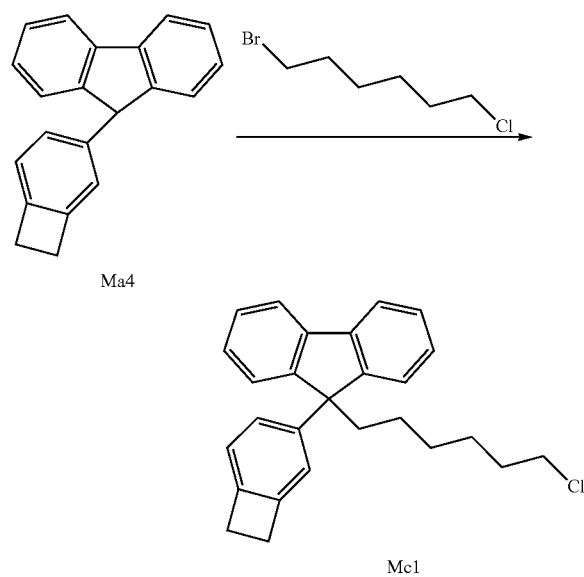

A gas in a flask equipped with a stirrer was purged with a nitrogen gas, then, sodium hydride (60 wt %, dispersed in liquid paraffin) (10.9 g), tetrahydrofuran (268 mL) and 1-bromo-6-chlorohexane (198.3 g) were added. Thereafter, the whole flask was light-shielded, and cooled at 0 to 5° C. To this, a mixed liquid of a compound Ma4 (67.0 g) and tetrahydrofuran (330 mL) was added over a period of 2.5 hours, then, the mixture was heated up to 50° C., and stirred at 50° C. for 6 hours. To this were added heptane (536 mL) and water (268 mL), and an aqueous layer was separated. The resultant organic layer was washed with water, then, magnesium sulfate was added. The resultant mixed liquid was filtrated, and the resultant filtrate was concentrated under reduced pressure, thereby obtaining a coarse product. The resultant coarse product was recrystallized from isopropanol, then, the resultant crystal was dissolved in a mixed liquid of toluene and heptane, and activated carbon (9.6 g) was added. The resultant mixed liquid was filtrated, and the resultant filtrate was concentrated under reduced pressure. The resultant residue was recrystallized from a mixed liquid of toluene and heptane, thereby obtaining 81.0 g of a compound Mc1 as a white solid. The compound Mc1 had an HPLC area percentage value (UV: 254 nm) of 99.5%. This operation was repeated, thereby obtaining a necessary amount of the compound Mc1.

$^1$H-NMR (CD$_2$Cl$_2$, 300 MHz) δ (ppm): 0.71-0.83 (2H, m), 1.27 (4H, t), 1.58-1.68 (2H, m), 2.49-2.54 (2H, m), 3.08-3.19 (4H, m), 3.49 (2H, t), 6.89 (1H, s), 6.94 (1H, d), 7.07 (1H, d), 7.25-7.44 (6H, m), 7.33 (2H, d).

Synthesis Example 3

Synthesis of Compound Mc2

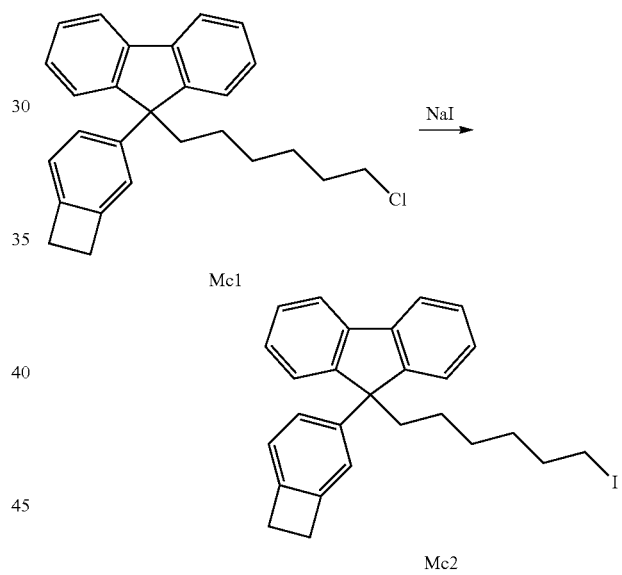

A gas in a flask equipped with a stirrer was purged with a nitrogen gas, then, the compound Mc1 (124.4 g), sodium iodide (385.5 g) and acetone (786 mL) were added, then, the mixture was heated up to the reflux temperature, and stirred at the reflux temperature for 34 hours. Thereafter, the mixture was cooled down to room temperature, and to the resultant mixed liquid were added heptane, toluene and water, then, an aqueous layer was separated. The resultant organic layer was washed with water, then, magnesium sulfate was added. The resultant mixed liquid was filtrated, and the resultant filtrate was concentrated under reduced pressure, thereby obtaining a coarse product. The resultant coarse product was recrystallized from a mixed liquid of heptane and isopropanol, thereby obtaining 143 g of a compound Mc2 as a white solid. The compound Mc2 had an HPLC area percentage value (UV: 254 nm) of 99.4%.

$^1$H-NMR (CD$_2$Cl$_2$, 300 MHz) δ (ppm): 0.71-0.83, (2H, m), 1.20-1.36 (4H, m), 1.60-1.70 (2H, m), 2.48-2.54 (2H, m), 3.13-3.18 (6H, m), 6.89 (1H, s), 6.94 (1H, d), 7.07 (1H, d), 7.25-7.43 (6H, m), 7.83 (2H, d).

Example: 3

Synthesis of Compound MM2

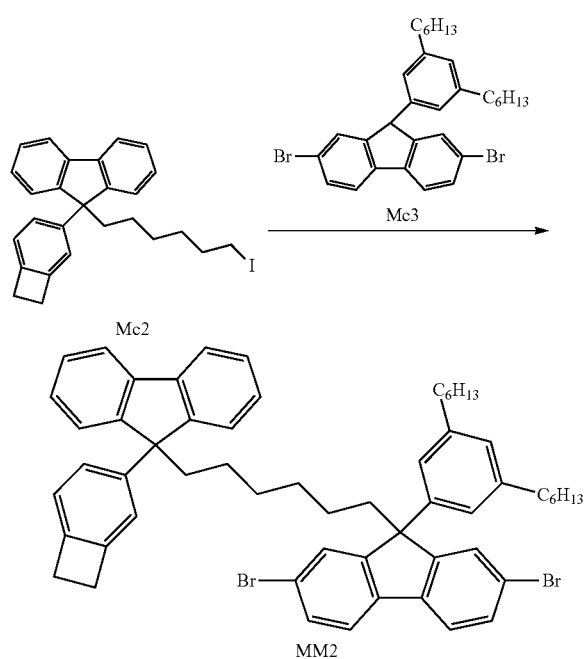

A gas in a flask equipped with a stirrer was purged with a nitrogen gas, then, sodium hydride (60 wt %, dispersed in liquid paraffin) (1.0 g), tetrahydrofuran (42.5 mL), N,N-dimethylformamide (42.5 mL) and the compound Mc2 (10.8 g) were added. Thereafter, the whole flask was light-shielded, and cooled at 0 to 5° C. To this, a mixed liquid of a compound Mc3 (10.6 g) synthesized according to a synthesis method described in Japanese Patent Application National Publication No. 2014-506609 and tetrahydrofuran (42.5 mL) was added over a period of 1 hour, then, the mixture was stirred at 0 to 5° C. for 4 hours. The resultant reaction mixture wan heated up to room temperature, then, toluene (106 mL) and water (106 mL) were added, and an aqueous layer was separated. The resultant organic layer was washed with water, then, sodium sulfate was added. The resultant mixed liquid was filtrated through a filter paved with silica gel, and the resultant filtrate was concentrated under reduced pressure, thereby obtaining a coarse product. An operation of recrystallizing the resultant coarse product from a mixed liquid of ethyl acetate and acetonitrile was repeated, thereby obtaining 14.3 g of a compound MM2 as a white solid. The compound MM2 had an HPLC area percentage value (UV: 254 nm) of 99.5% or more.

LC-MS (positive): m/z: 955 ([M+K]$^+$)

$^1$H-NMR (CD$_2$Cl$_2$, 300 MHz) δ (ppm): 0.56-0.65 (4H, m), 0.90-1.32 (22H, m), 1.54-1.58 (4H, m), 2.34-2.42 (4H, m), 2.52 (4H, t), 3.12 (4H, d), 6.74 (2H, s), 6.85 (1H, s), 6.92 (2H, d), 7.00-7.05 (1H, m), 7.19 (2H, d), 7.26-7.41 (6H, m), 7.53 (2H, d), 7.65 (2H, d), 7.80 (2H, d).

Synthesis Example 10

Synthesis of Compounds MM10 to MM17

A compound MM10 was synthesized according to a synthesis method described in International Publication WO2005/049546.

A compound MM11 was synthesized according to a synthesis method described in JP-A No. 2010-189630.

A compound MM12 was synthesized according to a synthesis method described in JP-A No. 2010-215886.

A compound MM13 was synthesized according to a synthesis method described in International Publication WO2013/191088.

A compound MM14 was synthesized according to a synthesis method described in JP-A 2010-189630.

A compound MM15 was synthesized according to a synthesis method described in International Publication WO2009/131255.

A compound MM16 was synthesized according to a synthesis method described in International Publication WO2013/146806.

A compound MM17 was synthesized according to a synthesis method described in Japanese Patent Application National Publication No. 2007-528916.

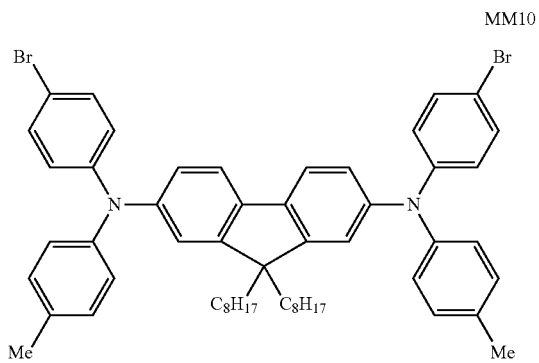

MM10

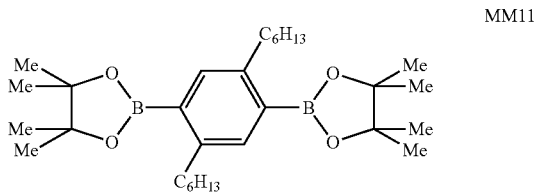

MM11

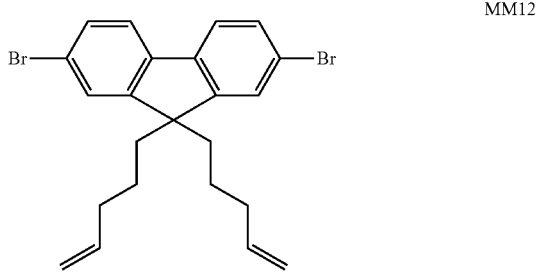

MM12

MM13
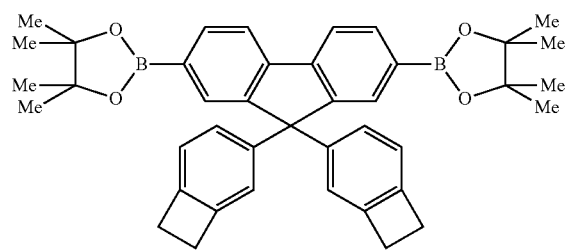
MM14
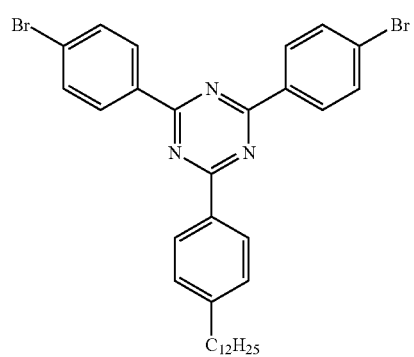
MM15
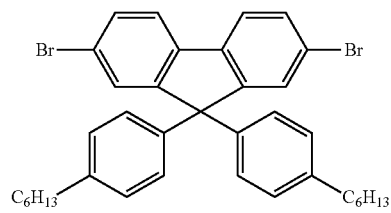
MM16
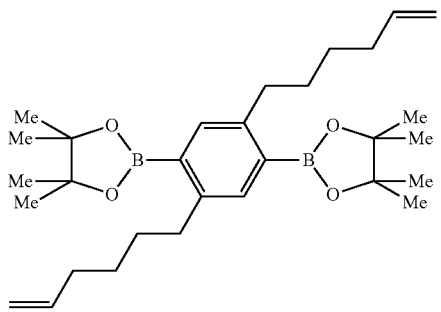
MM17
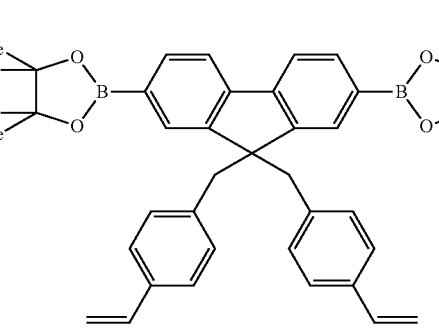
Synthesis Example 11
Synthesis of Metal Complex Ca1
A metal complex Ca1 was synthesized according to a synthesis method described in International Publication WO2009/131255.
Ca1
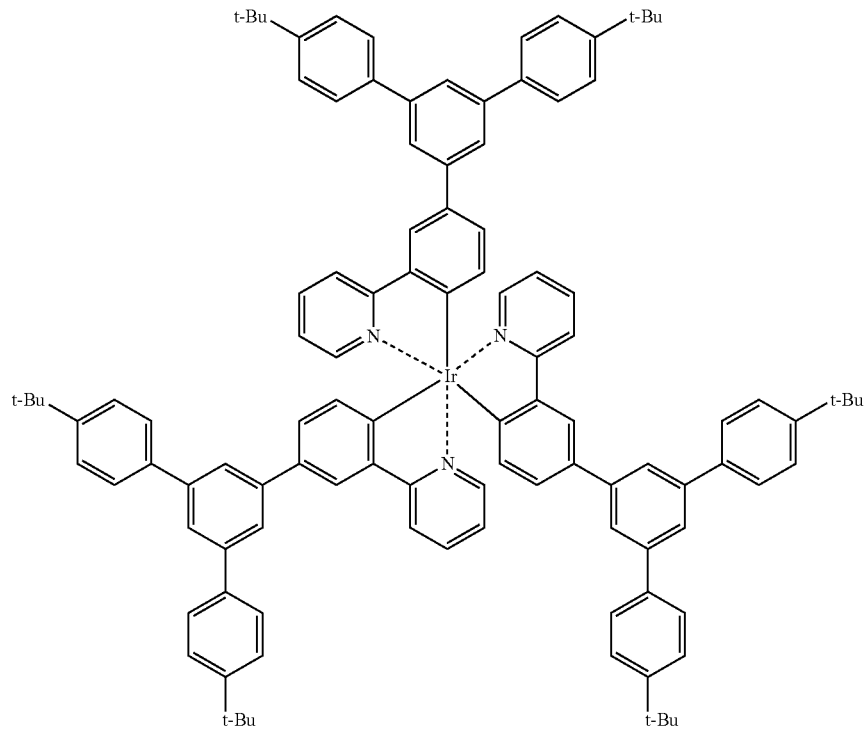

Example 4

Synthesis of Polymer Compound 1

(Step 1) An inert gas atmosphere was prepared in a reaction vessel, then, the compound MM10 (918.4 mg), the compound MM11 (493.3 mg), the compound MM12 (115.6 mg), the compound MM1 (257.8 mg), dichlorobis(tris-o-methoxyphenylphosphine)palladium (2.6 mg) and toluene (71 mL) were added, and the mixture was heated at 105° C.

(Step 2) Into the reaction liquid, a 20 wt % tetraethylammonium hydroxide aqueous solution (10 mL) was dropped, and the mixture was refluxed for 5 hours.

(Step 3) After the reaction, to this were added phenylboronic acid (36.6 mg) and dichlorobis(triso-O-methoxyphenylphosphine)palladium (2.6 mg), and the mixture was refluxed for 16.5 hours.

(Step 4) After the reaction, to this was added a sodium diethyldithiacarbamate aqueous solution, and the mixture was stirred at 80° C. for 2 hours. After cooling, the reaction liquid was washed with water twice, with a 3 wt % acetic acid aqueous solution twice, and with water twice, and the resultant solution was dropped into methanol, to observe precipitation. The precipitate was dissolved in toluene, and the solution was purified by passing through an alumina column and a silica gel column in this order. The resultant solution was dropped into methanol, the mixture was stirred, then, the resultant precipitate was isolated by filtration, and dried, thereby obtaining 1.10 g of a polymer compound 1. The polymer compound 1 had a Mn of $3.3 \times 10^4$ and a Mw of $3.2 \times 10^5$.

The polymer compound 1 is a copolymer having a constitutional unit derived from the compound MM10, a constitutional unit derived from the compound MM11, a constitutional unit derived from the compound MM12 and a constitutional unit derived from the compound MM1 at molar ratios of 40:40:10:10, according to theoretical values calculated from the amounts of charged raw materials.

Synthesis Example 12

Synthesis of Polymer Compound 2

A nitrogen atmosphere was prepared in a reaction vessel, then, the compound MM11 (822.2 mg), the compound MM15 (850.7 mg), the compound MM14 (209.7 mg) and toluene (37 mL) were added, and the mixture was heated at 80° C., Thereafter, to this were added palladium acetate (0.41 mg), tris(2-methoxyphenyl)phosphine (2.30 mg) and a 20 wt % tetraethylammonium hydroxide aqueous solution (5.8 g), and the mixture was stirred for 4 hours under reflux. Thereafter, to this was added phenylboronic acid (40.6 mg), and the mixture was stirred for 2 hours under reflux. Thereafter, to this was added a solution prepared by dissolving sodium N,N-diethyldithiocarbamate trihydrate (0.46 g) in ion-exchanged water (9 mL), and the mixture was stirred at 85° C. for 2 hours. The resultant organic layer was washed with 3.6 wt % hydrochloric acid twice, with a 2.5 wt % ammonia aqueous solution twice and with ion-exchanged water five times, in series. The resultant organic layer was dropped into methanol, to observe precipitation. The resultant precipitate was isolated by filtration, and dried. The resultant solid was dissolved in toluene, and the solution was allowed to pass through a silica gel column and an alumina column through which toluene had passed previously. The resultant solution was dropped into methanol, to observe precipitation. The resultant precipitate was isolated by filtration, and dried, thereby obtaining a polymer compound 2 (1.11 g). The polymer compound 2 had a Mn of $8.7 \times 10^4$ and a Mw of $2.3 \times 10^5$.

The polymer compound 2 is a copolymer having a constitutional unit derived from the compound MM11, a constitutional unit derived from the compound MM14 and a constitutional unit derived from the compound MM15 at molar ratios of 50:10:40, according to theoretical values calculated from the amounts of charged raw materials.

Comparative Example C1

Synthesis of Polymer Compound 3

A polymer compound 3 (0.95 g) was obtained in the same manner as for synthesis of the polymer compound 1 excepting that (Step 1) in synthesis of the polymer compound 1 was changed to "An inert gas atmosphere was prepared in a reaction vessel, then, the compound MM10 (918.4 mg), the compound MM11 (491.4 mg), the compound MM12 (115.6 mg), the compound MM13 (156.9 mg), dichlorobis(tris-o-methoxyphenylphosphine)palladium (2.6 mg) and toluene (71 mL) were mixed, and heated at 105° C.". The polymer compound 3 had a Mn of $3.5 \times 10^4$ and a Mw of $3.4 \times 10^5$.

The polymer compound 3 is a copolymer having a constitutional unit derived from the compound MM10, a constitutional unit derived from the compound MM11, a constitutional unit derived from the compound MM12 and a constitutional unit derived from the compound MM13 at molar ratios of 40:40:10:10, according to theoretical values calculated from the amounts of charged raw materials.

Example 5

Synthesis of Polymer Compound 4

A polymer compound 4 (1.05 g) was obtained in the same manner as for synthesis of the polymer compound 1 excepting that (Step 1) in synthesis of the polymer compound 1 was changed to "An inert gas atmosphere was prepared in a reaction vessel, then, the compound MM10 (917.2 mg), the compound MM11 (499.6 mg), the compound MM1 (259.2 mg), the compound MM2 (230.1 mg), dichlorobis(tris-o-methoxyphenylphosphine)palladium (2.6 mg) and toluene (71 mL) were mixed, and heated at 105° C.". The polymer compound 4 had a Mn of $4.0 \times 10^4$ and a Mw of $2.8 \times 10^5$.

The polymer compound 4 is a copolymer having a constitutional unit derived from the compound MM10, a constitutional unit derived from the compound MM11, a constitutional unit derived from the compound MM1 and a constitutional unit derived from the compound MM2 at molar ratios of 40:40:10:10, according to theoretical values calculated from the amounts of charged raw materials.

Example 6

Synthesis of Polymer Compound 5

A polymer compound 5 (1.23 g) was obtained in the same manner as for synthesis of the polymer compound 1 excepting that (Step 1) in synthesis of the polymer compound 1 was changed to "An inert gas atmosphere was prepared in a reaction vessel, then, the compound MM10 (917.2 mg), the compound MM16 (49.6 mg), the compound MM1 (923.0 mg), dichlorobis(tris-o-methoxyphenylphosphine)palladium (2.6 mg) and toluene (71 mL) were mixed, and heated at 105° C.". The polymer compound 5 had a Mn of $2.3 \times 10^4$ and a Mw of $1.2 \times 10^5$.

The polymer compound 5 is a copolymer having a constitutional unit derived from the compound MM10, a constitutional unit derived from the compound MM16 and a constitutional unit derived from the compound MM1 at molar ratios of 50:5:45, according to theoretical values calculated from the amounts of charged raw materials.

Example 7

Synthesis of Polymer Compound 6

A polymer compound 6 (1.23 g) was obtained in the same manner as for synthesis of the polymer compound 1 excepting that (Step 1) in synthesis of the polymer compound 1 was changed to "An inert gas atmosphere prepared in a reaction vessel, then, the compound MM10 (917.2 mg), the compound MM16 (49.6 mg), the compound MM11 (194.8 mg), the compound MM1 (518.5 mg), dichlorobis(tris-o-methoxyphenylphosphine)palladium (2.6 mg) and toluene (71 mL) were mixed, and heated at 105° C.". The polymer compound 6 had a Mn of $2.5 \times 10^4$ and a Mw of $3.0 \times 10^5$.

The polymer compound 6 is a copolymer having a constitutional unit derived from the compound MM10, a constitutional unit derived from the compound MM16, a constitutional unit derived from the compound MM11 and a constitutional unit derived from the compound MM1 at molar ratios of 50:5:20:25, according to theoretical values calculated from the amounts of charged raw materials.

Comparative Example C2

Synthesis of Polymer Compound 7

A polymer compound 7 (0.92 g) was obtained in the same manner as for synthesis of the polymer compound 1 excepting that (Step 1) in synthesis of the polymer compound 1 was changed to "An inert gas atmosphere was prepared in a reaction vessel, then, the compound MM10 (918.4 mg), the compound MM11 (502.3 mg), the compound MM12 (116.0 mg), the compound MM17 (163.9 mg), dichlorobis(tris-o-methoxyphenylphosphine)palladium (2.6 mg) and toluene (71 mL) were mixed, and heated at 105° C.". The polymer compound 7 had a Mn of $3.3 \times 10^4$ and a Mw of $2.2 \times 10^5$.

The polymer compound 7 is a copolymer having a constitutional unit derived from the compound MM10, a constitutional unit derived from the compound MM11, a constitutional unit derived from the compound MM12 and a constitutional unit derived from the compound MM17 at molar ratios of 40:40:10:10, according to theoretical values calculated from the amounts of charged raw materials.

Example D1

Fabrication and Evaluation of Light Emitting Device D1

On a glass substrate carrying thereon an ITO film having a thickness of 45 nm formed by a sputtering method, a polythiophene.sulfonic acid type hole injecting agent AQ-1200 (manufactured by Plextronics) was spin-coated as a hole injection material to form a film with a thickness of 65 nm, and this was heated on a hot plate at 170° C. for 15 minutes in an air atmosphere.

Next, the polymer compound 1 was dissolved in xylene to prepare a 0.7 wt % xylene solution. This xylene solution was spin-coated to form a film with a thickness of 20 nm, and this was heated on a hot plate at 180° C. for 60 minutes in a nitrogen gas atmosphere.

Next, the polymer compound 2 and the metal complex Ca1 were respectively dissolved in xylene, to prepare 1.8 wt % xylene solutions. Next, the xylene solution of the polymer compound 2 and the xylene solution of the metal complex Ca1 were mixed so that the weight ratio of solid components of the polymer compound 2 and the metal complex Ca1 was 70:30. This xylene solution was spin-coated to form a film with a thickness of 80 nm, and this was heated on a hot plate at 150° C. for 10 minutes in a nitrogen gas atmosphere. Thereafter, as a cathode, sodium fluoride was vapor-deposited with a thickness of about 7 nm, then, aluminum was vapor-deposited with a thickness of about 120 nm, to fabricate a light emitting device D1. After the degree of vacuum reached $1 \times 10^{-4}$ Pa or lower, vapor-deposition of a metal was initiated.

When voltage was applied to the light emitting device D1, EL emission having a peak at 520 nm was obtained from this device, and the maximum light emission efficiency was 81.2 cd/A.

Example D2

Fabrication and Evaluation of Light Emitting Device D2

A light emitting device D2 was fabricated in the same manner as in Example D1 excepting that a 0.7 wt % xylene solution was prepared using the polymer compound 4 instead of the polymer compound 1 in Example D1.

When voltage was applied to the light emitting device D2, EL emission having a peak at 520 nm was obtained from this device, and the maximum light emission efficiency was 83.2 cd/A.

Example D3

Fabrication and Evaluation of Light Emitting Device D3

A light emitting device D3 was fabricated in the same manner as in Example D1 excepting that a 0.7 wt % xylene solution was prepared using the polymer compound 5 instead of the polymer compound 1 in Example D1.

When voltage was applied to the light emitting device D3, EL emission having a peak at 520 nm was obtained from this device, and the maximum light emission efficiency was 77.0 cd/A.

Example D4

Fabrication and Evaluation of Light Emitting Device D4

A light emitting device D4 was fabricated in the same manner as in Example D1 excepting that a 0.7 wt % xylene solution was prepared using the polymer compound 6 instead of the polymer compound 1 in Example D1.

When voltage was applied to the light emitting device D4, EL emission having a peak at 520 nm was obtained from this device, and the maximum light emission efficiency was 74.9 cd/A.

Comparative Example CD1

Fabrication and Evaluation of Light Emitting Device CD1

A light emitting device CD1 was fabricated in the same manner as in Example D1 excepting that a 0.7 wt % xylene solution was prepared using the polymer compound 3 instead of the polymer compound 1 in Example D1.

When voltage was applied to the light emitting device CD1, EL emission having a peak at 520 nm was obtained from this device, and the maximum light emission efficiency was 66.0 cd/A.

Comparative Example CD2

Fabrication and Evaluation of Light Emitting Device CD2

A light emitting device CD2 was fabricated in the same manner as in Example D1 excepting that a 0.7 wt % xylene solution was prepared using the polymer compound 7 instead of the polymer compound 1 in Example D1.

When voltage was applied to the light emitting device CD2, EL emission having a peak at 520 nm was obtained from this device, and the maximum light emission efficiency was 60.3 cd/A.

INDUSTRIAL APPLICABILITY

The light emitting device of the present invention is excellent in light emission efficiency. The polymer compound and the composition of the present invention are useful for production of the light emitting device.

The invention claimed is:

1. A polymer compound comprising a constitutional unit represented by the following formula (2):

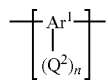
(2)

wherein
Ar$^1$ represents an aromatic hydrocarbon group or a heterocyclic ring group and these groups each optionally have a substituent,
n represents an integer of 1 to 4, and
Q$^2$ represents a group represented by the following formula and when a plurality of Q$^2$ are present, they can be the same or different:

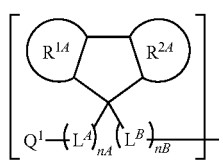
(1)

wherein
Ring R$^{1A}$ and Ring R$^{2A}$ each independently represent an aromatic hydrocarbon ring or a heterocyclic ring, nA represents an integer of 0 to 5, and nB represents an integer of 1 to 5, L$^A$ and L$^B$ each independently represent an alkylene group, a cycloalkylene group, an arylene group, a divalent heterocyclic ring group, a group represented by —NR'—, an oxygen atom or a sulfur atom and these groups each optionally have a substituent, and R' represents a hydrogen atom, an alkyl group, a cycloalkyl group, an aryl group or a monovalent heterocyclic group and these groups each optionally have a substituent, and when a plurality of L$^A$ and L$^B$ are present, they may be the same or different at each occurrence, and Q$^1$ represents a crosslinkable group selected from the following Group A', wherein Group A' is a crosslinkable group selected from the group consisting of:

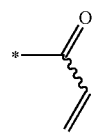
(XL-2)

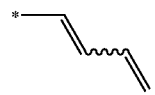
(XL-3)

(XL-4)

*———— (XL-5)

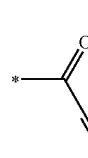
(XL-6)

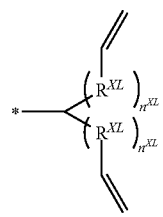
(XL-7)

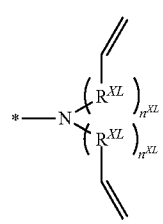
(XL-8)

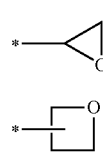
(XL-9)

(XL-10)

-continued

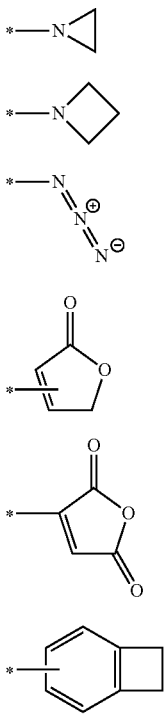

(XL-11)

(XL-12)

(XL-13)

(XL-14)

(XL-15)

and (XL-17)

wherein
R$^{XL}$ represents a methylene group, an oxygen atom or a sulfur atom, n$^{XL}$ represents an integer of 0 to 5, and when a plurality of R$^{XL}$, are present, they may be the same or different, and when a plurality of n$^{XL}$ are present, they may be the same or different,
* represents a binding position, and
these crosslinkable groups each optionally have a substituent.

2. The polymer compound according to claim 1, further comprising a constitutional unit represented by the following formula (X):

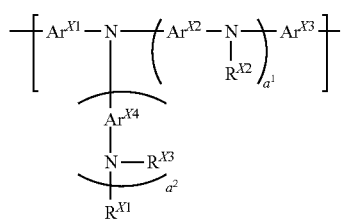

(X)

wherein
a$^1$ and a$^2$ each independently represent an integer of 0 or more,
Ar$^{X1}$ and Ar$^{X3}$ each independently represent an arylene group or a divalent heterocyclic ring group and these groups each optionally have a substituent,
Ar$^{X2}$ and Ar$^{X4}$ each independently represent an arylene group, a divalent heterocyclic ring group or a divalent group in which at least one arylene group and at least one divalent heterocyclic group are bonded directly to each other, and these groups each optionally have a substituent, and R$^{X1}$, R$^{X2}$ and R$^{X3}$ each independently represent a hydrogen atom, an alkyl group, a cycloalkyl group, an aryl group or a monovalent heterocyclic group and these groups each optionally have a substituent.

3. The polymer compound according to claim 1, further comprising a constitutional unit represented by the following formula (Y):

$$\text{―}[\text{Ar}^{Y1}]\text{―} \quad (Y)$$

wherein Ar$^{Y1}$ represents an arylene group, a divalent heterocyclic group or a divalent group in which at least one arylene group and at least one divalent heterocyclic group are bonded directly to each other, and these groups each optionally have a substituent.

4. The polymer compound according to claim 1, wherein Ring R$^{1A}$ and Ring R$^{2A}$ are a benzene ring optionally having a substituent.

5. The polymer compound according to claim 1, wherein Ar$^1$ is a group obtained by removing from a benzene ring optionally having a substituent, a fluorene ring optionally having a substituent, a naphthalene ring optionally having a substituent, a phenanthrene ring optionally having a substituent or a dihydrophenanthrene ring optionally having a substituent (2+n) hydrogen atoms linked directly to carbon atoms constituting the ring.

6. The polymer compound according to claim 3, wherein the constitutional unit represented by the formula (Y) is a constitutional unit represented by the following formula (Y-1) or a constitutional unit represented by the following formula (Y-2):

(Y-1)

wherein R$^{Y1}$ represents a hydrogen atom, an alkyl group, a cycloalkyl group, an alkoxyl group, a cycloalkoxy group, an aryl group or a monovalent heterocyclic group and these groups each optionally have a substituent, and the plurality of R$^{Y1}$ may be the same or different, and adjacent R$^{Y1}$s may be combined together to form a ring together with the carbon atoms to which they are attached:

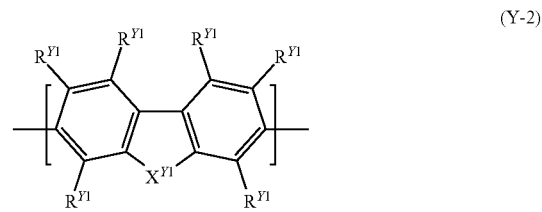

(Y-2)

wherein R$^{Y1}$ represents the same meaning as described above, X$^{Y1}$ represents a group represented by —C(R$^{Y2}$)$_2$—, —C(R$^{Y2}$)=C(R$^{Y2}$)— or —C(R$^{Y2}$)$_2$—C(R$^{Y2}$)$_2$—, and R$^{Y2}$ represents a hydrogen atom, an alkyl group, a cycloalkyl group, an alkoxyl group, a cycloalkoxy group, an aryl group or a monovalent heterocyclic group and these groups each optionally have a substituent, and the plurality of $R^{Y2}$ may be the same or different, and $R^{Y2}$ s may be combined together to form a ring together with the carbon atoms to which they are attached.

7. The polymer compound according to claim 1, wherein the content of the constitutional unit represented by the formula (2) is 3 to 90 mol % with respect to the total content of constitutional units contained in the polymer compound.

8. A compound represented by the following formula (2M):

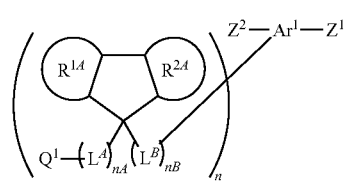
(2M)

wherein

Ring $R^{1A}$ and Ring $R^{2A}$ each independently represent an aromatic hydrocarbon ring or a heterocyclic ring and these rings each optionally have a substituent, nA represents an integer of 0 to 5, and nB represents an integer of 1 to 5, $L^A$ and $L^B$ each independently represent an alkylene group, a cycloalkylene group, an arylene group, a divalent heterocyclic ring group, a group represented by —NR'—, an oxygen atom or a sulfur atom and these groups each optionally have a substituent, and R' represents a hydrogen atom, an alkyl group, a cycloalkyl group, an aryl group or a monovalent heterocyclic group and these groups each optionally have a substituent, and when a plurality of $L^A$ and $L^B$ are present, they may be the same or different at each occurrence, $Q^1$ represents a crosslinkable group selected from the following Group A' of crosslinkable group, $Ar^1$ represents an aromatic hydrocarbon group or a heterocyclic ring group and these groups each optionally have a substituent, n represents an integer of 1 to 4, and $Z^1$ and $Z^2$ each independently represent a group selected from the following Group A of substituent or Group B of substituent:

wherein Group A' is a crosslinkable group selected from the group consisting of:

(XL-2)

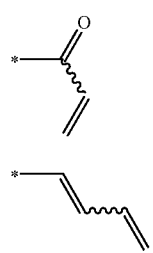
(XL-3)

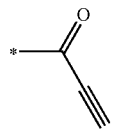
(XL-4)

(XL-5)
*≡

(XL-6)
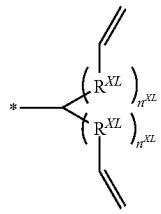

(XL-7)
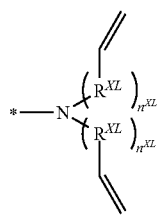

(XL-8)

(XL-9)

(XL-10)

(XL-11)
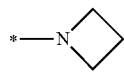

(XL-12)
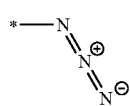

(XL-13)
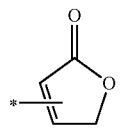

(XL-14)
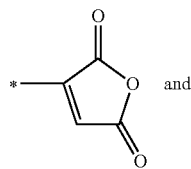

(XL-15)
and

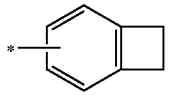

(XL-17)

wherein
$R^{X1}$ represents a methylene group, an oxygen atom or a sulfur atom, $n^{XL}$ represents an integer of 0 to 5, and when a plurality of $R^{XL}$ are present, they may be the same or different, and when a plurality of $n^{X1}$ are present, they may be the same or different, \* represents a binding position, and these crosslinkable groups each optionally have a substituent:

wherein Group A is a substituent selected from the group consisting of:
 a chlorine atom, a bromine atom, an iodine atom, and a group represented by —O—S(=O)$_2$R$^{C1}$, wherein R$^{C1}$ represents an alkyl group, a cycloalkyl group or an aryl group and these groups each optionally have a substituent, wherein Group B is a substituent selected from the group consisting of:
 a group represented by —B(OR$^{C2}$)$_2$, wherein R$^{C2}$ represents a hydrogen atom, an alkyl group, a cycloalkyl group or an aryl group and these groups each optionally have a substituent, and the plurality of R$^{C2}$ may be the same or different and may be combined together to form a cyclic structure together with the oxygen atoms to which they are attached;
 a group represented by —BF$_3$Q', wherein Q' represents a lithium atom, a sodium atom, a potassium atom, a rubidium atom or a cesium atom;
 a group represented by —MgY', wherein Y' represents a chlorine atom, a bromine atom or an iodine atom;
 a group represented by —ZnY'', wherein Y'' represents a chlorine atom, a bromine atom or an iodine atom; and
 a group represented by —Sn(R$^{C3}$)$_3$, wherein R$^{C3}$ represents a hydrogen atom, an alkyl group, a cycloalkyl group or an aryl group and these groups each optionally have a substituent, and the plurality of R$^{C3}$ may be the same or different and may be combined together to form a cyclic structure together with the tin atom to which they are attached.

9. A composition comprising
the polymer compound according to claim 1, and
at least one material selected from the group consisting of a hole transporting material, a hole injection material, an electron transporting material, an electron injection material, a light emitting material, an antioxidant and a solvent.

10. A light emitting device produced by using the polymer compound according to claim 1.

\* \* \* \* \*